(12) United States Patent
Levi et al.

(10) Patent No.: US 11,850,026 B2
(45) Date of Patent: Dec. 26, 2023

(54) REMOTE PORTABLE VITAL SIGNS MONITORING

(71) Applicant: THE GOVERNING COUNCIL OF THE UNIVERSITY OF TORONTO, Toronto (CA)

(72) Inventors: Ofer Levi, Toronto (CA); Eric Y. Zhu, Toronto (CA); Dene Alexander Adrian Ringuette, Pickering (CA); Ryan Chu, Markham (CA)

(73) Assignee: THE GOVERNING COUNCIL OF THE UNIVERSITY OF TORONTO

( * ) Notice: Subject to any disclaimer, the term of this patent is extended or adjusted under 35 U.S.C. 154(b) by 97 days.

(21) Appl. No.: 17/357,486

(22) Filed: Jun. 24, 2021

(65) Prior Publication Data
US 2021/0401298 A1     Dec. 30, 2021

Related U.S. Application Data

(60) Provisional application No. 63/043,732, filed on Jun. 24, 2020.

(51) Int. Cl.
*A61B 5/0205* (2006.01)
*A61B 5/00* (2006.01)

(52) U.S. Cl.
CPC .......... *A61B 5/0205* (2013.01); *A61B 5/0004* (2013.01); *A61B 5/6898* (2013.01); *A61B 5/725* (2013.01); *A61B 5/7225* (2013.01)

(58) Field of Classification Search
CPC .......................... A61B 5/6898; A61B 5/0205
See application file for complete search history.

(56) References Cited

U.S. PATENT DOCUMENTS

| | | | |
|---|---|---|---|
| 8,558,873 B2 | 10/2013 | Mceldowney | |
| 9,443,304 B2 | 9/2016 | Damkat | |
| 9,538,158 B1 | 1/2017 | Rush et al. | |
| 9,753,131 B2 | 9/2017 | Adib et al. | |

(Continued)

OTHER PUBLICATIONS

W. Verkruysse, "Remote plethysmographic imaging using ambient light", Opt Express. 2008; 16(26): 21434-21445 (16 pages).

(Continued)

*Primary Examiner* — Eric F Winakur
*Assistant Examiner* — Emily C Clement
(74) *Attorney, Agent, or Firm* — BERESKIN & PARR LLP/ S.E.N.C.R.L. s.r.l; Tonino Rosario Orsi

(57) ABSTRACT

Devices and methods are provided for performing remote physiological monitoring of vital signs from one or more subjects. Camera pairs including an intensity camera and a depth camera are used to obtain intensity image data and depth image data that are then processed using one or more ROIs for extracting heart rate and respiratory waveforms from which the heart rate and respiratory rate may be estimated. In other embodiments, multiple ROIs may be used to obtain several heart rate and respiratory rate values which are then fused together. In some embodiments motion compensation may be used prior to generating the heart rate and respiratory waveforms. In other embodiments, multiple camera pairs may be used to obtain intensity and depth data from multiple fields of view which may be used to obtain several heart rate and respiratory rate values which are then fused together.

20 Claims, 28 Drawing Sheets

(56) References Cited

U.S. PATENT DOCUMENTS

| | | |
|---|---|---|
| 9,770,197 B2 | 9/2017 | Bresch et al. |
| 9,967,541 B2 | 5/2018 | Piestun |
| 10,045,702 B2 | 8/2018 | Jeanne et al. |
| 10,187,626 B2 | 1/2019 | Shechtman et al. |
| 10,219,739 B2 | 3/2019 | Mestha et al. |
| 10,229,491 B1 | 3/2019 | Rush et al. |
| 10,292,623 B2 | 5/2019 | Rocque et al. |
| 10,441,173 B2 | 10/2019 | Shan et al. |
| 10,478,078 B2 | 11/2019 | De Haan |
| 10,489,661 B1 | 11/2019 | Rush et al. |
| 2014/0213863 A1 | 7/2014 | Loseu et al. |
| 2016/0120476 A1 | 5/2016 | Liu et al. |
| 2017/0071547 A1 | 3/2017 | Van Dinther et al. |
| 2017/0164847 A1 | 6/2017 | Pande et al. |
| 2017/0238842 A1* | 8/2017 | Jacquel ............... A61B 5/7221 |
| 2017/0238875 A1 | 8/2017 | Olivier et al. |
| 2017/0367657 A1 | 12/2017 | Pande et al. |
| 2018/0289270 A1 | 10/2018 | Zalevsky et al. |
| 2018/0333102 A1 | 11/2018 | De Haan et al. |
| 2018/0350081 A1* | 12/2018 | Hsieh ..................... G06T 7/248 |
| 2019/0000391 A1 | 1/2019 | De Haan et al. |
| 2019/0159701 A1 | 5/2019 | Beiderman et al. |
| 2019/0209046 A1* | 7/2019 | Addison ............. A61B 5/0077 |
| 2019/0212124 A1 | 7/2019 | Zalevsky et al. |
| 2019/0290145 A1 | 9/2019 | Zalevsky et al. |
| 2019/0374113 A1 | 12/2019 | Zalevsky et al. |
| 2020/0297227 A1* | 9/2020 | Rong ................... G06T 7/0012 |

OTHER PUBLICATIONS

M.Z. Poh, "Non-contact, automated cardiac pulse measurements using video imaging and blind source separation", Opt Express. 2010 (13 pages).

D. Da He, "A continuous, wearable, and wireless heart monitor using head ballistocardiogram (bcg) and head electrocardiogram (ecg)", Annual International Conference of the IEEE Engineering in Medicine and Biology Society 2011 pp. 4729-4732 (4 pages).

M.Z. Poh, "Advancements in Noncontact, Multiparameter Physiological Measurements Using a Webcam", IEEE Transactions on Biomedical Engineering 2011 (5 pages).

M.C. Yu, "Noncontact respiratory measurement of volume change using depth camera", Conf Proc IEEE Eng Med Biol Soc 2012 pp. 2371-2374 (4 pages).

G. Balakrishnan, "Detecting pulse from head motions in video", IEEE Conference on Computer Vision and Pattern Recognition 2013 pp. 3430-3437 (7 pages).

G. De Haan, "Robust Pulse Rate from Chrominance-Based rPPG", IEEE Transactions on Biomedical Engineering 2013 pp. 1-9 (9 pages).

M. Bartula, "Camera-based System for Contactless Monitoring of Respiration", 35th Annual International Conference of the IEEE EMBS 2013 pp. 2672-2675 (4 pages).

G. De Haan, "Improved motion robustness of remote-PPG by using the blood volume pulse signature", Physiological Measurement 2014 pp. 1913-1926 (15 pages).

X. Li, "Remote Heart Rate Measurement From Face Videos Under Realistic Situations", IEEE Conference on Computer Vision and Pattern Recognition 2014 pp. 4264-4271 (8 pages).

M. Kumar, A. Veeraraghavan, and A. Sabharwal, "DistancePPG: Robust non-contact vital signs monitoring using a camera," Biomed. Opt. Express 6, 1565-1588 2015 (24 pages).

J. Chen, Z. Chang, Q. Qiu, X. Li, G. Sapiro, A. Bronstein, and M. Pietikainen, "RealSense = real heart rate: Illumination invariant heart rate estimation from videos," in 2016 Sixth International Conference on Image Processing Theory, Tools and Applications (IPTA)(2016) (6 pages).

R. Janssen, "Video-based respiration monitoring with automatic region of interest detection", Physiol. Meas. 2016 pp. 100-114 (16 pages).

C. Yang, "Estimating heart rate and rhythm via 3d motion tracking in depth video", IEEE Transactions on Multimedia 2017 pp. 1625-1636 (12 pages).

W. Wang, A. C. D. Brinker, S. Stuijk, and G. D. Haan, "Algorithmic Principles of Remote PPG," IEEE Transactions on Biomedical Engineering 64, 1479-1491 (2017) (13 pages).

F. L. Siena, B. Byrom, P. Watts, and P. Breedon, "Utilising the Intel RealSense Camera for Measuring Health Outcomes in Clinical Research," J. Medical Systems 42, 53 (2018) (10 pages).

V. Moco, S. Stuijk, and G. De Haan, "New insights into the origin of remote PPG signals in visible light and infrared," Scientific Reports 8, 8501 (2018) (15 pages).

R. Chu, M. Downing, A. Srivastava, J. Cafazzo, A. Mihailidis and O. Levi, "Remote Acquisition of Vital Signs Using Infrared and Depth-Enabled Cameras", International Neuro-rehab. symposium (NIRS 2019), Toronto, Canada, paper INRS93 (Jun. 24, 2019) (poster) (1 page).

Moco, and W. Verkruysse, "Pulse oximetry based on photoplethysmography imaging with red and green light," Journal of Clinical Monitoring and Computing (2020) pp. 123-133 (11 pages).

R. Chu, D. Ringuette, E. Y. Zhu, A. Mihailidis and O. Levi, "Motion-Tolerant Remote Respiration Monitoring with a Multi-Camera Configuration", Imaging Systems and Applications (IS) conference, OSA Technical Digest (CD), paper 3395473, Vancouver, BC, (Jun. 24, 2020), (oral) (2 pages).

R. Chu, E. Y. Zhu, D. Ringuette, A. Mihailidis and O. Levi, "Correlation of Near-Infrared Intensity and Depth Channels for Remote Vital Signs Monitoring", submitted to the Photonics North 2020 conference, Niagara Falls, Canada, (May 26, 2020) cancelled presentation (1 page).

A. C. Den Brinker & W. Wang, Chapter 3—Model-based camera-PPG: Pulse-rate monitoring in fitness, Editor(s): Wenjin Wang, Xuyu Wang, Contactless Vital Signs Monitoring, Academic Press, 2022, pp. 51-78, ISBN 9780128222812, https://doi.org/10.1016/B978-0-12-822281-2.00011-1. (https://www.sciencedirect.com/science/article/pii/B9780128222812000111) (28 pages).

A. C. Den Brinker & W. Wang, Chapter 4—Camera-based respiration monitoring: Motion and PPG-based measurement, Editor(s): Wenjin Wang, Xuyu Wang, Contactless Vital Signs Monitoring, Academic Press, 2022, pp. 79-97, ISBN 9780128222812, https://doi.org/10.1016/B978-0-12-822281-2.00012-3. (https://www.sciencedirect.com/science/article/pii/B9780128222812000123) (19 pages).

Face Recognition with OpenCV (Open Source Computer Vision), Intel, date found Jun. 23, 2020 <https://docs.opencv.org/2.4/modules/contrib/doc/facerec/facerec_tutorial.html> (26 pages).

CubeMos, Software Development Kit (SDK), date found Jun. 23, 2020 <https://www.cubemos.com/> (6 pages).

Skeleton Tracking SDA for Intel, CubeMos, Jun. 2021 <https://web.archive.org/web/20210617045409/https://www.intelrealsense.com/skeleton-tracking/> (7 pages).

Martinez, "OpenPose: Whole-Body Pose Estimation", Robotics Institute, Carnegie Mellon University, Apr. 2019 <https://www.ri.cmu.edu/publications/openpose-whole-body-pose-estimation/> (31 pages).

Solano, "Human pose estimation using OpenPose with TensorFlow (Part 1)", AR/VR Journey: Augmented & Virtual Reality Magazine, Oct. 2, 2017 <https://arvrjourney.com/human-pose-estimation-using-openpose-with-tensorflow-part-1-7dd4ca5c8027> (18 pages).

CMU-Perpetual-Computing-Lab/openpose 2019 <https://github.com/CMU-Perceptual-Computing-Lab/openpose> (9 pages).

MPII Human Pose Dataset, Max Plank Institute Jun. 2014 <http://human-pose.mpi-inf.mpg.de/#overview> (1 page).

Chandra et al., "Accurate Human-Limb Segmentation in RGB-D images for Intelligent Mobility Assistance Robots", Proceedings of the IEEE International Conference on Computer Vision (ICCV) Workshops, 2015, pp. 44-50 <https://www.cv-foundation.org//openaccess/content_iccv_2015_workshops/w12/papers/Chandra_Accurate_Human-Limb_Segmentation_ICCV_2015_paper.pdf> (7 pages).

* cited by examiner

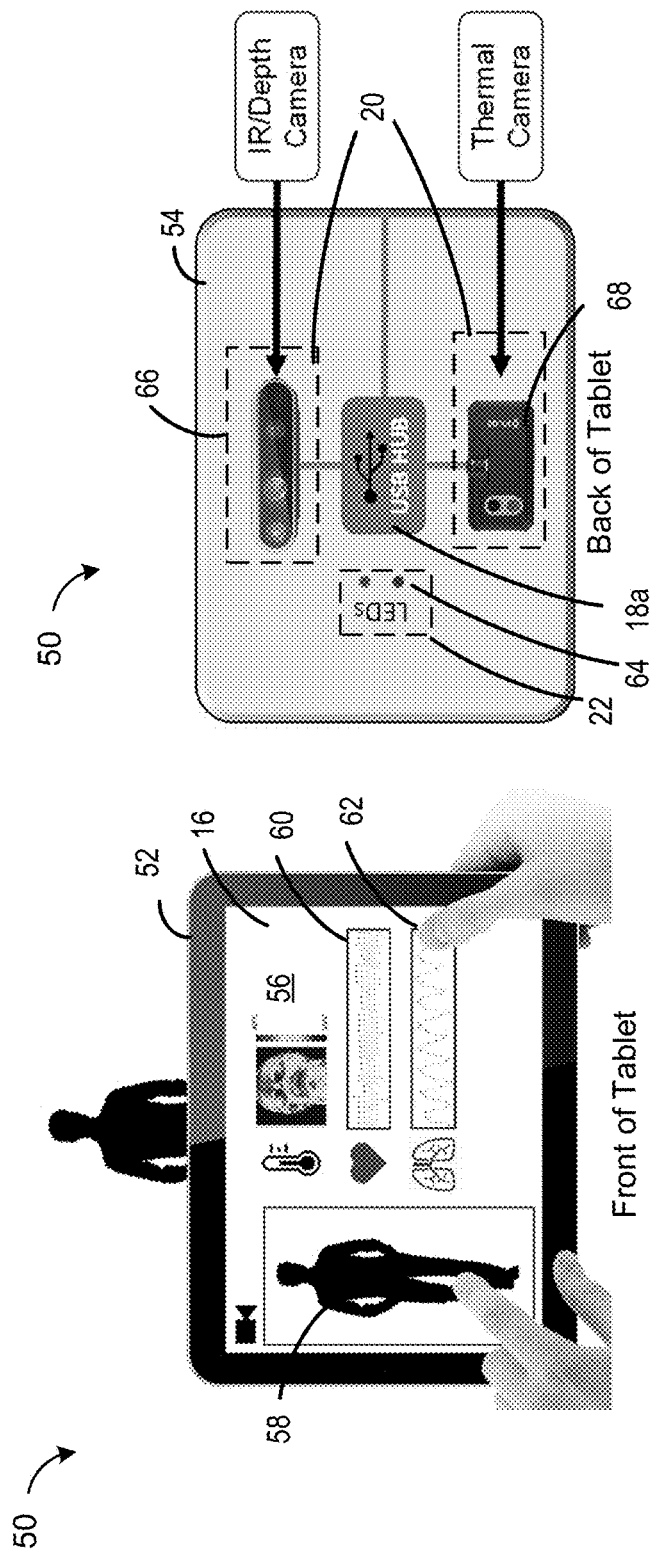

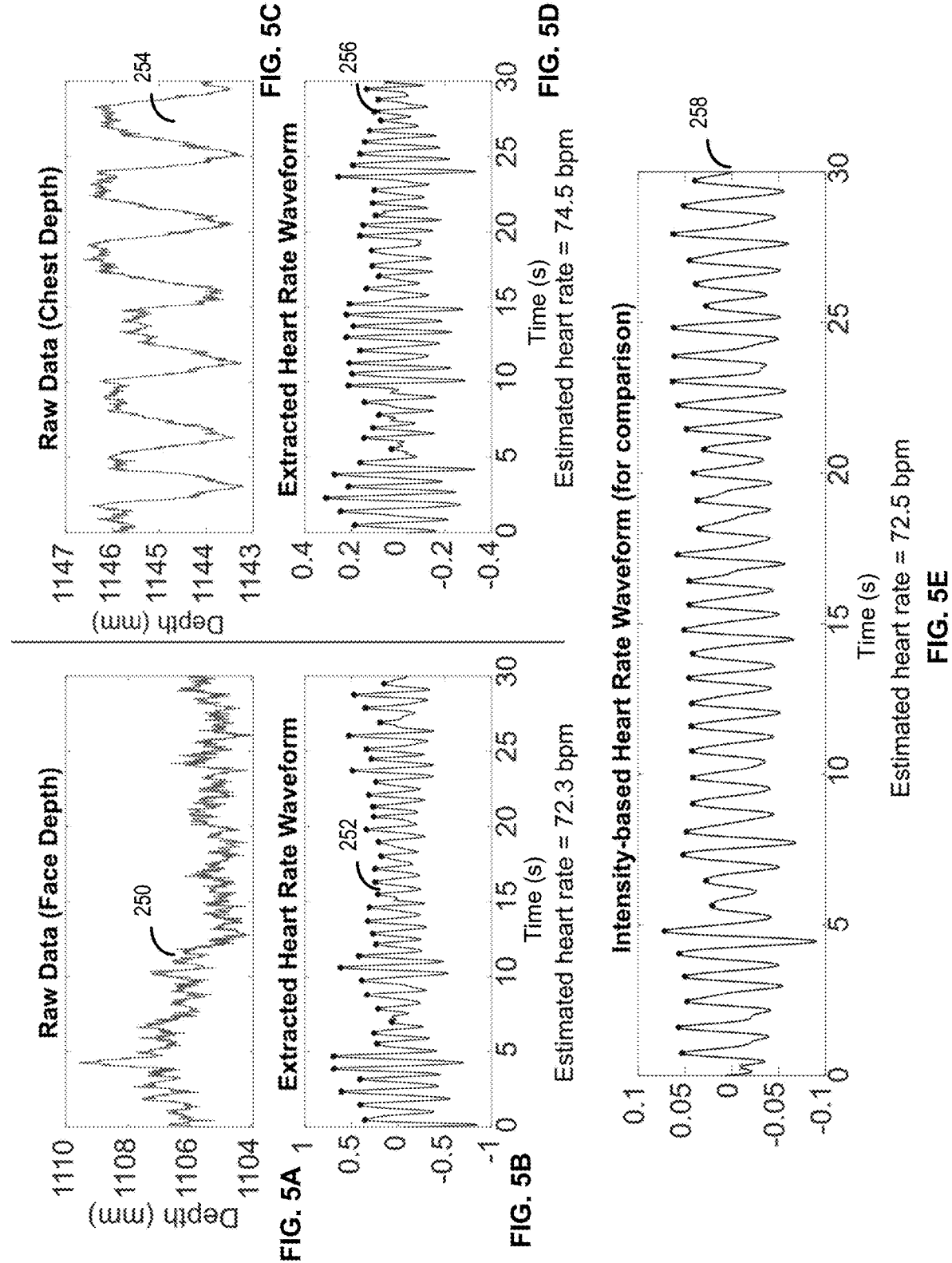

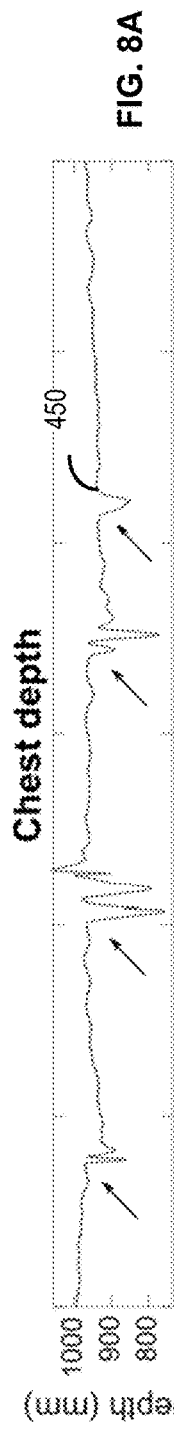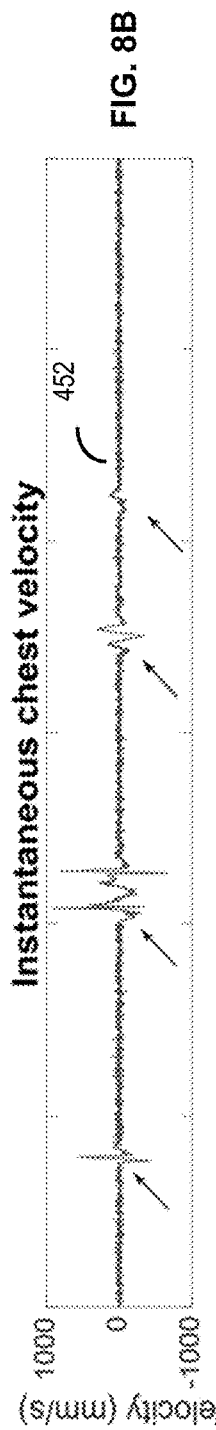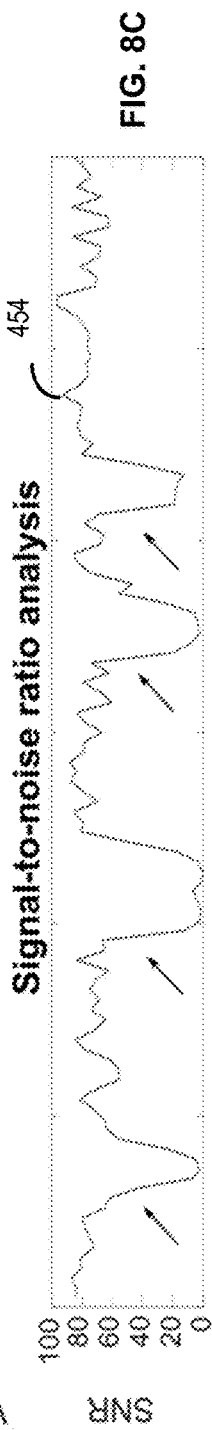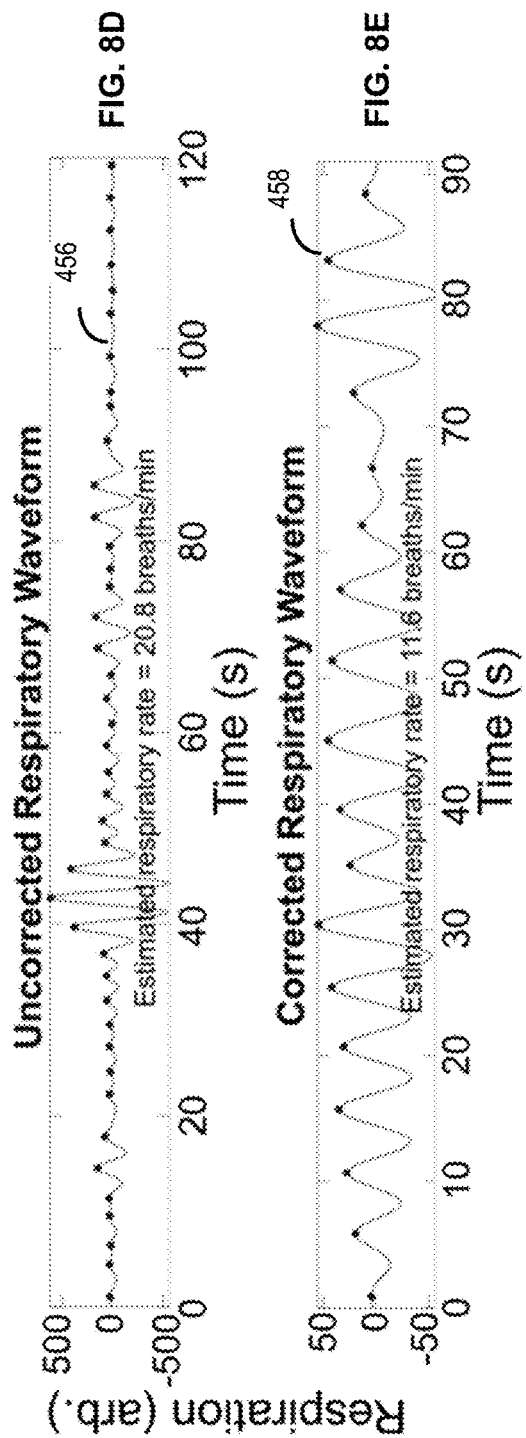

Estimated heart rate = 78.3 bpm

Estimated heart rate = 80.2 bpm

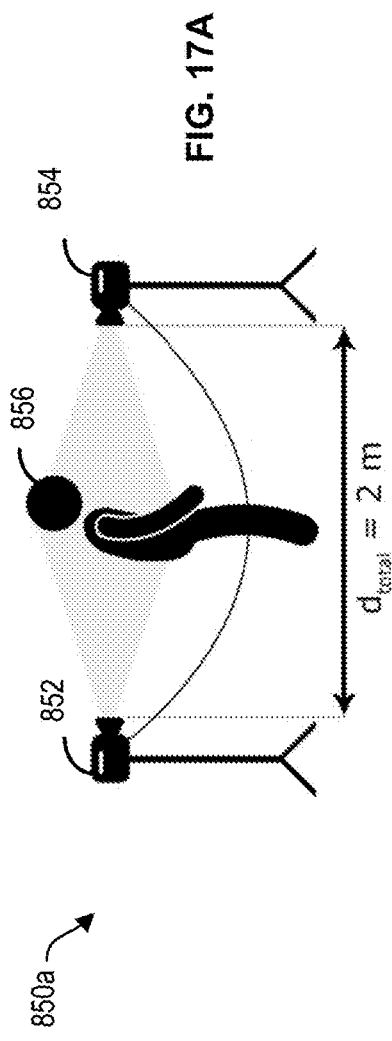
FIG. 17A
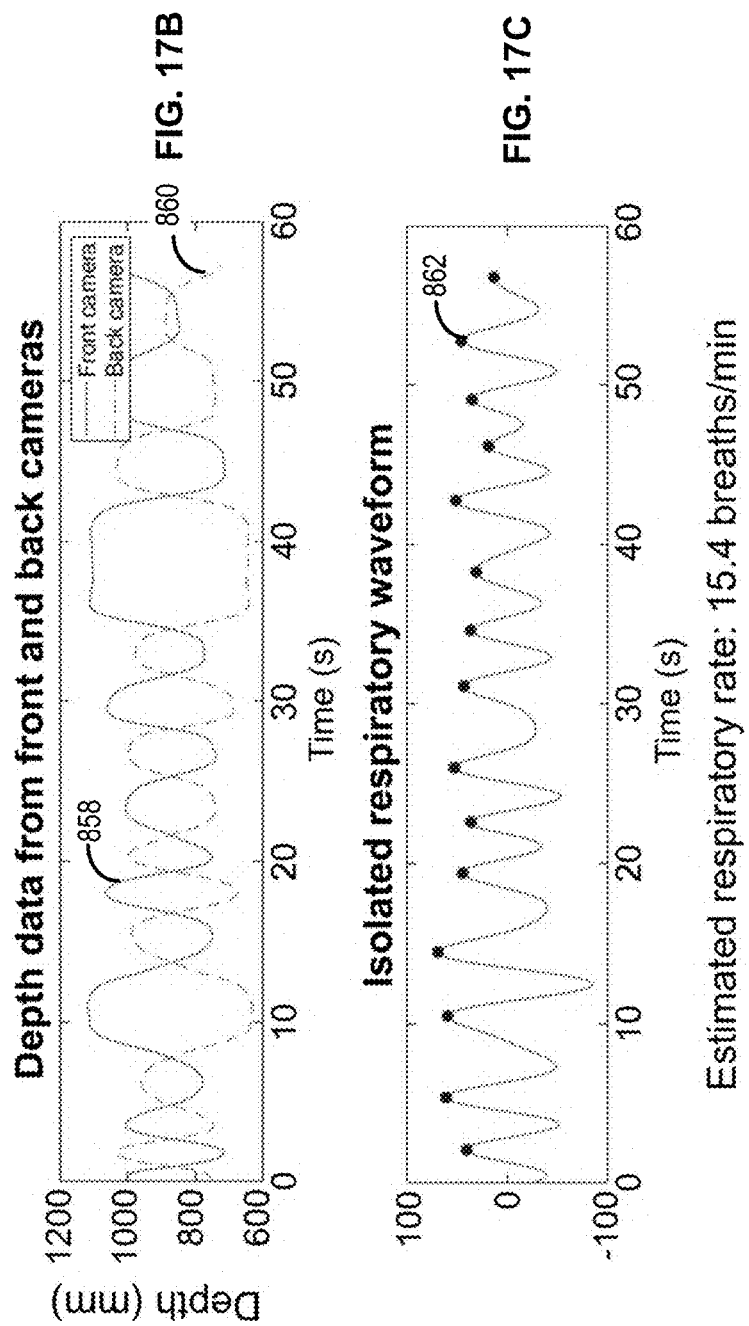
FIG. 17B
FIG. 17C

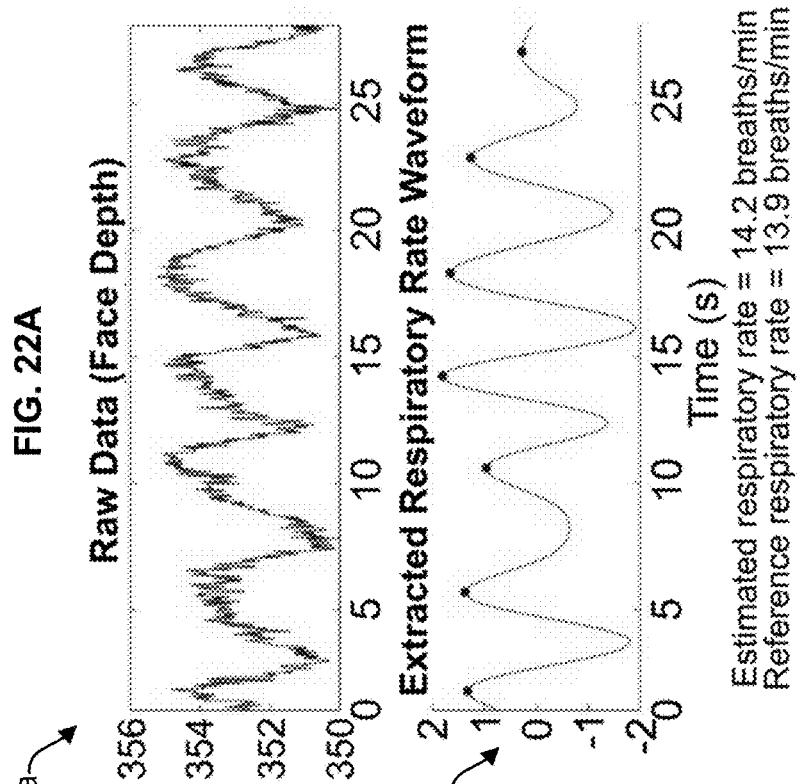
FIG. 22A
FIG. 22B
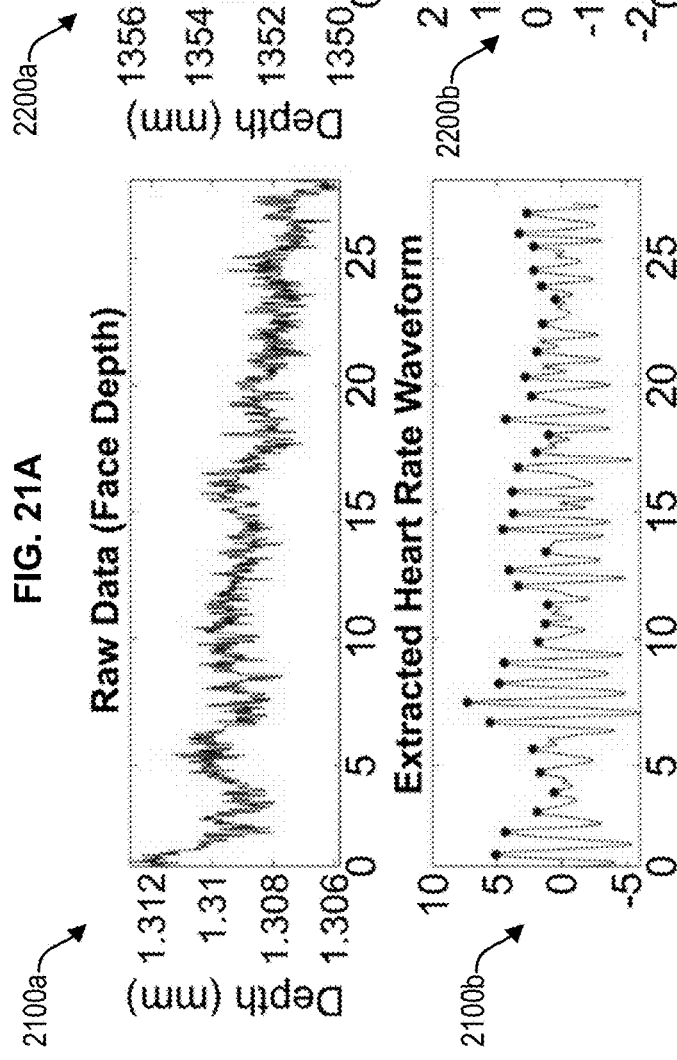
FIG. 21A
FIG. 21B

REMOTE PORTABLE VITAL SIGNS MONITORING

CROSS REFERENCE TO RELATED APPLICATIONS

This application claims priority from U.S. Provisional Patent Application No. 63/043,732, filed on Jun. 24, 2020, which is hereby incorporated by reference in its entirety.

FIELD

Various embodiments are described herein that relate to remote portable measurement of vital signs.

BACKGROUND

Vital signs are an objective measurement for the essential physiological functions of a living organism. They are "vital" as their measurement and assessment are the critical first steps for any clinical evaluation of a patient, which may be a person or an animal. Vital signs include, but are not limited to, temperature, heart rate, respiratory rate, and blood pressure, which together reflect the patient's general physiological state as well as specific disease states. Deviations from normal ranges in more than one of the vital signs usually represent some physiological disturbance.

Current technologies for measuring vital signs use either a physical connection between the patient and a bedside vital signs monitor. However, such methods of vital sign monitoring in hospitals may be uncomfortable, are generally non-portable, and may be expensive.

As an alternative, a small Holter Monitor may be worn by the patient, where electrodes are attached to the patient's skin to monitor vital signs for a few days, focusing on electrical data such as ECG, and estimating breathing rate from changes in resistance between the electrodes, due to respiration. However, challenges exist with this monitoring such as maintaining adequate contact between the electrodes and the patient's skin as well as the delay in receiving the recorded signals (i.e., after the patient has finished wearing the Holter Monitor) and then having to analyze the data at a later time. Accordingly, this type of monitoring is not real-time.

Recently, camera based-systems have been proposed to measure a patient's vital signs through small changes in reflected light intensity. However, current techniques of remotely measuring such vital signs with a conventional light camera can easily become inaccurate when the patient moves or when the ambient light intensity changes.

Furthermore, as monitoring of patient vital signs moves out of the ICU and the hospital, the monitoring is generally seen to be inconsistent and discontinuous. This may result in unexpected adverse events that contribute to "failure-to-rescue" mortality, where clinical staff, other medical professionals or caregivers are unable to detect early deterioration of the patient.

SUMMARY OF VARIOUS EMBODIMENTS

Various embodiments of devices and methods for remote monitoring of physiological are provided according to the teachings herein.

In one aspect, in accordance with the teachings herein, there is provided a device for performing remote physiological signal monitoring on a subject, wherein the device comprises: a first camera unit having a first depth camera with a first depth channel for providing depth data and an intensity camera with an intensity channel for providing intensity data obtained from capturing depth images and intensity images, respectively, of the subject; a memory for storing program instructions for performing a method of remote physiological signal monitoring on the subject; and a processor unit that includes at least one processor that is operably coupled to the first camera unit for receiving the depth data and/or the intensity data and operatively coupled to the memory for executing the program instructions for performing the method of physiological signal monitoring which configures the at least one processor to: detect at least one region of interest (ROI) for images in the intensity data and/or the depth data; generate waveforms for the intensity data and/or the depth data where a given data point in the waveforms is obtained using pixel values in the at least one detected ROI for the images in the intensity data and/or the depth data; estimate at least one heart rate (HR) value for the subject by performing high frequency bandpass filtering on the waveforms of the intensity data and/or the depth data to obtain at least one heart rate waveform for the intensity data and/or the depth data; performing peak detection on the at least one HR waveform to determine a series of peaks and estimating the at least one HR value based on temporal spacing between the series of peaks in the at least one hear rate waveform; and estimate at least one respiratory rate (RR) value for the subject by performing low frequency bandpass filtering on the waveforms of the intensity data and/or the depth data to obtain at least one respiratory waveform for the intensity data and/or the depth data; performing peak detection on the at least one respiratory waveform to determine a series of peaks and estimating the at least one RR value based on temporal spacing between the series of peaks in the at least one respiratory waveform.

In at least one embodiment, the at least one processor is further configured to analyze the waveforms for the intensity data and/or the depth data and is further configured to: identify one or more segments of the waveform for the intensity data and/or the depth data which include subject motion; determine if the motion in each of the identified segments is classifiable as a large motion; and if the motion is classifiable as a large motion, perform motion rejection by discarding the respective identified segments of the intensity data and/or the depth data, otherwise applying motion compensation to the respective identified segments.

In at least one embodiment, the at least one processor is further configured to perform motion compensation on the waveform of the depth data by identifying segments in the waveform of the depth data that have an instantaneous velocity that is larger than a predefined velocity threshold and/or have a signal to noise ratio (SNR) that is lower than a first predefined SNR threshold and removing the identified segments from the waveform of the depth data before performing the high frequency bandpass filtering.

In at least one embodiment, the at least one processor is further configured to perform motion compensation on the waveform of the intensity data by identifying segments in the waveform of the intensity data that have an instantaneous intensity change rate that is larger than a predefined intensity change rate threshold and/or have a signal to noise ratio (SNR) that is lower than a second predefined SNR threshold and removing the identified segments from the waveform of the intensity data before performing the high frequency bandpass filtering.

In at least one embodiment, the at least one processor is further configured to use skeletal tracking to dynamically localize the at least one ROI for the images in the intensity data and/or the depth data.

In at least one embodiment, the at least one processor is configured to change a size of the at least one ROI to reflect different skeletal postures of the subject determined from the skeletal tracking.

In at least one embodiment, the at least one processor is configured to use skeletal tracking to detect motion events for the subject for intensity and/or depth data, determine a severity of a motion during a detected motion event, apply motion compensation when the severity of the motion indicates small movements and apply motion rejection when the severity of the motion indicates large movements.

In at least one embodiment, the at least one processor is configured to perform motion compensation by: (a) resizing and/or repositioning the at least one ROI on a body of the subject based on a location and orientation of the at least one ROI in space as determined from the skeletal tracking; and/or (b) performing intensity renormalization based on the depth data.

In at least one embodiment, the at least one processor is configured to perform motion rejection by discarding sections of the intensity data and/or the depth data that are compromised by motion of the subject.

In at least one embodiment, the at least one ROI comprises one or more cheek regions, a forehead region, an upper chest region, a lower chest region, an abdominal region, a back region, a back of the head and/or a whole face of the subject.

In at least one embodiment, the camera unit includes at least one additional camera pair that has a different field of view than the first camera pair for obtaining a second set of intensity data and/or depth data and the at least one processor is configured to obtain additional estimates of HR and RR from the second set of intensity data and/or depth data.

In at least one embodiment, the device includes an additional light source or the camera unit includes an internal light source that are used for illuminating a scene for which the image data is being acquired.

In at least one embodiment, the at least one processor is configured to use the additional light source or the internal light source to estimate the physiological signals independent of ambient light.

In at least one embodiment, the at least one additional camera pair comprises a second camera unit that is positioned opposite the first camera unit, wherein the second set of intensity data and/or depth data generated by the second camera unit is used as a reference to subtract a subject's body movement as measured by the difference in distance between the first and second camera units and allow separation of the subject's body movement from vital signs related to depth changes and being optionally further used to obtain movement compensated estimates of HR and/or RR from the second set of intensity data and/or depth data.

In another aspect, in accordance with the teachings herein, there is provided a computer implemented method of performing remote physiological signal monitoring on a subject using at least one processor that is operatively coupled to a memory that stores program instructions for performing the method, wherein the method comprises: positioning the subject within a field of view of a first camera unit having a first depth camera with a first depth channel for providing depth data and an intensity camera with an intensity channel for providing intensity data obtained from capturing depth images and intensity images, respectively, of the subject; detecting at least one region of interest (ROI) for images in the intensity data and/or the depth data; generating waveforms for the intensity data and/or the depth data where a given data point in the waveforms is obtained using pixel values in the at least one detected ROI for the images in the intensity data and/or the depth data; estimating at least one heart rate (HR) value for the subject by performing high frequency bandpass filtering on the waveforms of the intensity data and/or the depth data to obtain at least one heart rate waveform for the intensity data and/or the depth data; performing peak detection on the at least one HR waveform to determine a series of peaks and estimating the at least one HR value based on temporal spacing between the series of peaks in the at least one hear rate waveform; and estimating at least one respiratory rate (RR) value for the subject by performing low frequency bandpass filtering on the waveforms of the intensity data and/or the depth data to obtain at least one respiratory waveform for the intensity data and/or the depth data; performing peak detection on the at least one respiratory waveform to determine a series of peaks and estimating the at least one RR value based on temporal spacing between the series of peaks in the at least one respiratory waveform.

In at least one embodiment, the method further comprises: identifying one or more segments of the waveform for the intensity data and/or the depth data which include subject motion; determining if the motion in each of the identified segments is classifiable as a large motion; and if the motion is classifiable as a large motion, performing motion rejection by discarding the respective segments of the intensity data and/or the depth data, otherwise applying motion compensation to the respective identified segments.

In at least one embodiment, the method further comprises performing motion compensation on the waveform of the depth data by identifying segments in the waveform of the depth data that have an instantaneous velocity that is larger than a predefined velocity threshold and/or have a signal to noise ratio (SNR) that is lower than a first predefined SNR threshold and removing the identified segments from the waveform of the depth data before performing the high frequency bandpass filtering.

In at least one embodiment, the method further comprises performing motion compensation on the waveform of the intensity data by identifying segments in the waveform of the intensity data that have an instantaneous intensity change rate that is larger than a predefined intensity change rate threshold and/or have a signal to noise ratio (SNR) that is lower than a second predefined SNR threshold and removing the identified segments from the waveform of the intensity data before performing the high frequency bandpass filtering.

In at least one embodiment, the method comprises using skeletal tracking to dynamically localize the at least one ROI for the images in the intensity data and/or the depth data.

In at least one embodiment, the method further comprises changing a size of the at least one ROI to reflect different skeletal postures of the subject determined from the skeletal tracking.

In at least one embodiment, the method further comprises using skeletal tracking to detect motion events for the subject for intensity and/or depth data, determining a severity of a motion during a detected motion event, apply motion compensation when the severity of the motion indicates small movements and applying motion rejection when the severity of the motion indicates large movements.

In at least one embodiment, the method further comprises performing motion compensation by: (a) resizing and/or repositioning the at least one ROI on a body of the subject based on a location and orientation of the at least one ROI in space as determined from the skeletal tracking; and/or (b) performing intensity renormalization based on the depth data.

In at least one embodiment, the method further comprises performing motion rejection by discarding sections of the intensity data and/or the depth data that are compromised by motion of the subject.

In at least one embodiment, the method comprises defining the at least one ROI to include one or more cheek regions, a forehead region, an upper chest region, a lower chest region, an abdominal region, a back region, a back of the head and/or a whole face of the subject.

In at least one embodiment, the method further comprises using at least one additional camera pair that has a different field of view than the first camera pair for obtaining a second set of intensity data and/or depth data and the obtaining additional estimates of HR and RR from the second set of intensity data and/or depth data.

In at least some embodiments, the at least one additional camera pair comprises a second camera unit that is positioned opposite the first camera unit, wherein the second set of intensity data and/or depth data generated by the second camera unit is used as a reference to subtract a subject's body movement as measured by the difference in distance between the first and second camera units and allow separation of the subject's body movement from vital signs related to depth changes and being optionally further used to obtain movement compensated estimates of HR and/or RR from the second set of intensity data and/or depth data.

In at least one embodiment, the method further comprises using an additional light source or using an internal light source of the camera unit for illuminating a scene for which the image data is being acquired.

In at least one embodiment, the method further comprises using the additional light source or the internal light source to estimate the physiological signals independent of ambient light.

In another aspect, in accordance with the teachings herein, there is provided a computer readable medium comprising a plurality of instructions that are executable on at least one processor of a device for adapting the device to implement a method for performing remote physiological monitoring, wherein the method is defined according to any of the methods described herein.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

FIGS. 1B and 1C show front and back views of another example embodiment of a remote physiological monitoring device.

FIG. 5A shows an example of a raw waveform of (spatially-averaged) depth data from the forehead Region of Interest (ROI) of a test subject.

FIG. 5B shows an example of a bandpass-filtered waveform used to determine HR.

FIG. 5C shows an example of a raw waveform measurement from an ROI on the chest of the test subject.

FIG. 5D shows the extracted HR waveform from the waveform of FIG. 5C.

FIG. 5E shows an example of an intensity-based HR waveform for comparison with the waveform of FIG. 5D.

FIG. 8A shows an example of average distance of a test subject's chest from a depth camera plotted against time.

FIG. 8B shows an example of test subject motion being detected by looking at large instantaneous velocities of the test subject's chest position (~tens of cm/s).

FIG. 8C shows an example of how the signal-to-noise ratio (SNR) of the chest depth measurements drops in correspondence with the occurrence of large instantaneous velocities of the chest depth movements in FIG. 8B.

FIG. 8D shows the RR waveform derived from the chest depth waveform of FIG. 8A without motion removal.

FIG. 8E shows the RR waveform derived from the chest depth waveform of FIG. 8A with motion removal.

FIG. 17A shows a demonstration of motion tolerance using two cameras in a front and back configuration on either side of a standing test subject where the test subject's torso is used as an ROI, in accordance with some example embodiments.

FIG. 17B shows 3-D depth data that is acquired from each camera in the setup of FIG. 17A while the subject exhibits limited back and forth motion (i.e., swaying while standing).

FIG. 17C shows a respiratory waveform that is isolated from the two depth signals to derive RR.

FIG. 21A shows an example of a raw waveform measuring depth data obtained from an ROI located on a face of a test subject and obtained in low light settings.

FIG. 21B shows an extracted HR waveform from the waveform of FIG. 21A.

FIG. 22A shows an example of a raw waveform measuring depth data obtained from an ROI located on the chest of a test subject and obtained in low light settings.

FIG. 22B shows an extracted RR waveform from the waveform of FIG. 22A.

Figure 1A:
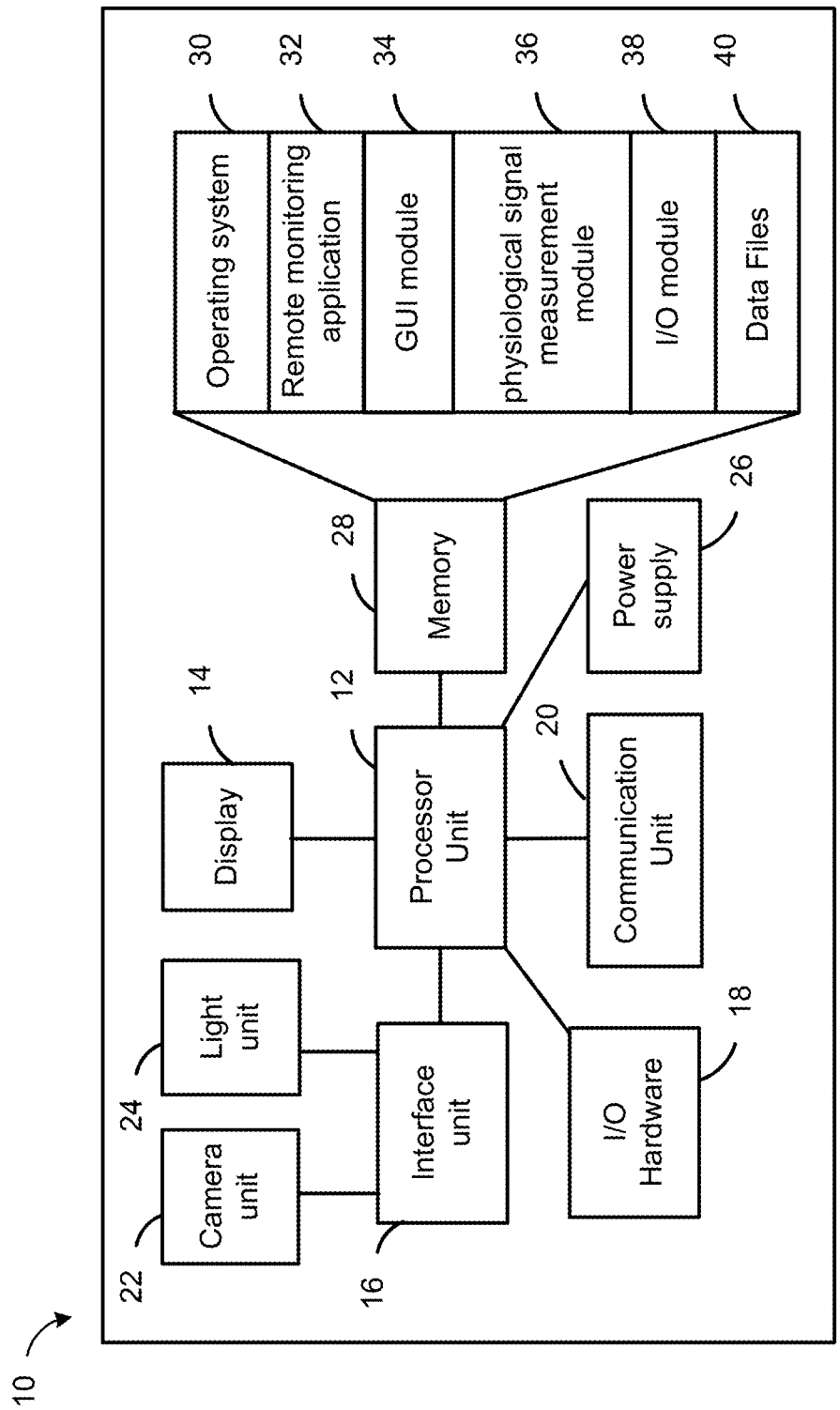
FIG. 1A shows an example embodiment of a remote physiological monitoring device that may be used for the remote monitoring of physiological signals from a patient, a subject, another individual or an animal.

Further aspects and features of the example embodiments described herein will appear from the following description taken together with the accompanying drawings.

DETAILED DESCRIPTION OF THE EMBODIMENTS

Various embodiments in accordance with the teachings herein will be described below to provide an example of at least one embodiment of the claimed subject matter. No embodiment described herein limits any claimed subject matter. The claimed subject matter is not limited to devices, systems, or methods having all of the features of any one of the devices, systems, or methods described below or to features common to multiple or all of the devices, systems, or methods described herein. It is possible that there may be a device, system, or method described herein that is not an embodiment of any claimed subject matter. Any subject matter that is described herein that is not claimed in this document may be the subject matter of another protective instrument, for example, a continuing patent application, and the applicants, inventors, or owners do not intend to abandon, disclaim, or dedicate to the public any such subject matter by its disclosure in this document.

It will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures, and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have a mechanical or electrical connotation. For example, as used herein, the terms coupled or coupling can indicate that two elements or devices can be directly connected to one another or connected to one another through one or more intermediate elements or devices via an electrical signal, electrical connection, or a mechanical element depending on the particular context.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term, such as by 1%, 2%, 5%, or 10%, for example, if this deviation does not negate the meaning of the term it modifies.

Furthermore, the recitation of numerical ranges by endpoints herein includes all numbers and fractions subsumed within that range (e.g., 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed, such as 1%, 2%, 5%, or 10%, for example.

It should also be noted that the use of the term "window" or Graphical User Interface (GUI) in conjunction with describing the operation of any device, system or method described herein is meant to be understood as describing a user interface that is generated using software and shown on a display, monitor or screen for allowing a user to provide control inputs to control one or more of the methods described herein as well as to view raw data, processed data, waveforms, images and/or estimated physiological signal values.

The example embodiments of the devices, systems, or methods described in accordance with the teachings herein are implemented as a combination of hardware and software. For example, the embodiments described herein may be implemented, at least in part, by using one or more computer programs, executing on one or more programmable devices comprising at least one processing element and at least one storage element (i.e., at least one volatile memory element and at least one non-volatile memory element). The hardware may comprise input devices including at least one of a touch screen, a keyboard, a mouse, buttons, keys, sliders, and the like, as well as one or more of a display, a printer, and the like depending on the particular hardware implementation that is used.

It should also be noted that there may be some elements that are used to implement at least part of the embodiments described herein that may be implemented via software that is written in a high-level procedural language such as object oriented programming. The program code may be written in C++, C#, JavaScript, Python, MATLAB, or any other suitable programming language and may comprise modules or classes, as is known to those skilled in object-oriented programming. Alternatively, or in addition thereto, some of these elements implemented via software may be written in assembly language, machine language, or firmware as needed. In either case, the language may be a compiled or interpreted language.

At least some of these software programs may be stored on a computer readable medium such as, but not limited to, a ROM, a magnetic disk, an optical disc, a USB key, and the like that is readable by a device having at least one processor, an operating system, and the associated hardware and software that is necessary to implement the functionality of at least one of the embodiments described herein. The software program code, when executed by the at least one processor of the device, configures the at least one processor and the device to operate in a new, specific, and predefined manner (e.g., as a specific-purpose computing device) in order to perform at least one of the methods described herein.

At least some of the programs associated with the devices, systems, and methods of the embodiments described herein may be capable of being distributed in a computer program product comprising a computer readable medium that bears computer usable instructions, such as program code, for one or more processors. The medium may be provided in various forms, including non-transitory forms such as, but not limited to, one or more diskettes, compact disks, tapes, chips, and magnetic and electronic storage. In alternative embodiments, the medium may be transitory in nature such as, but not limited to, wire-line transmissions, satellite transmissions, internet transmissions (e.g., downloads), media, digital and analog signals, and the like. The computer useable instructions may also be in various formats, including compiled and non-compiled code.

Glossary of Terms and Acronyms:

Throughout this specification and the appended claims various words and phrases are defined. Once defined, the use of these terms herein shall bear the defined following meanings.

The term BPM means beats per minute, which are units for heart rate.

The term BrPM means breaths per minute, which are units for respiratory rate.

The term Depth Channel is synonymous with a 3-dimensional (3D) channel, producing a time series for depth image data.

The term FoV means field of view.

The term FPS means frames per second.

The term Intensity Channel is synonymous with a video channel, producing a time series for image data for images that are captured by an optical camera with a sensor sensitivity in the infrared and visible light spectrums.

The term PPG means photoplethysmography.

The term ROI means Region Of Interest.

The term RR means respiratory rate, which is measured in BrPM.

The term HR means Heart rate, which is measured in BPM.

The term subject is meant to cover a person, such as a patient, a senior or other individuals for whom remote physiological monitoring is to be performed in accordance with the teachings herein. The term subject may also cover animals that will receive remote physiological monitoring in accordance with the teachings herein.

Description of Various Embodiments

In one aspect, the teachings herein relate to the extraction from a subject, such as a patient or other individual, of vital signs data such as, but not limited to, heart rate, breathing rate, and body temperature, from using remote physiological monitoring which involves acquiring image data of the subject such as real-time video from at least one camera including a 3D camera, a depth camera and/or a thermal camera.

In another aspect, the teachings herein relate to the extraction of vital signs data from a subject using video image data, as mentioned previously, where the video image data is obtained from distances, such as about 1-3 meters, for example, and while the subject is stationary and/or moving. This is in contrast to conventional techniques which obtain data from close range (e.g., 30-50 cm) on a non-moving subject.

For example, the inventors have found that remote intensity measurements along with remote depth-based measurements of HR and RR, performed according to the teachings herein, can be obtained at a distance of more than about 2 meters that are found to be in agreement with the clinical gold standard to within about +/−3%.

In another aspect, in accordance with the teachings herein, the remote physiological devices and systems described herein can be implemented using low-cost hardware and software that allows for accurate remote diagnosis of patients at home and in isolation wards while minimizing contact with healthcare workers. For example, using a combination of cameras and associated methods described herein enables remote monitoring of vital signs in real-time including measurements of HR and RR through a combination of intensity-based and depth-based data from a subject or patient.

The inventors have found that the proposed combination of depth and intensity-based measurements provide a superior solution to remote measurement of physiological vital signs that is more robust to changes in ambient light and in some embodiments can also incorporate motion compensation and/or motion rejection as described herein.

The remote physiological monitoring technology described herein may be used in various situations. For example, the remote physiological monitoring method and hardware may be used to monitor patients who are at home who may develop symptoms or conditions that require immediate care at a clinic or a hospital, and the onset of these symptoms or conditions can be determined through the remote monitoring so that an alarm or message can be generated that the patient needs to go to a hospital or clinic.

In another example, the remote physiological monitoring technology described herein may be used in one or more patient rooms in a hospital or one more seniors rooms in an long-term care center to remotely monitor the vital signs of patients or seniors. The remotely monitored physiological signals can be sent to a central station such as a nurses station or a remote computer, for example, so that the physiological signals for these patients or seniors can be simultaneously monitored.

In another example, the remote physiological monitoring technology described herein, and in particular the data from the depth cameras and the intensity camera may be helpful for identifying symptoms related to a specific disease. For example, evaluating chest distension using 3D cameras during inhalation and exhalation can be used not only to estimate severity of a disease such as Chronic Obstructive Pulmonary Disease (COPD), but also indicate a rapid deterioration in lung functioning leading to Acute Respiratory Distress Syndrome (ARDS), which is a common complication in viral pneumonia.

In another example, the remote physiological monitoring technology may be helpful in identifying symptoms related to balance, and changes in the body center of mass or center of pressure (i.e., by monitoring the movement of the human skeleton, and in particular, the legs), during clinic and home rehabilitation sessions.

In another example, the remote physiological monitoring technology may be helpful for identifying suspected people with a health condition during travel, in an airport, a train station, or a bus station or during transit, or in a large sporting event, or before entering a large social gathering.

In another example, the remote portable vital signs monitoring hardware and methods described herein may be used in other environments such as, but not limited to, companies, airports, factories, sports facilities, sports arenas and outdoor events, where people are being monitored for certain physiological conditions.

Referring now to FIG. 1A, shown therein is an example embodiment of a remote physiological monitoring device 10 that may be used for the remote monitoring of physiological signals from a patient, a subject, another individual or an animal. The device 10 may be implemented using a single computing device that may be a tablet or a hand held device with integrated cameras, or it may be a desktop, laptop or notepad computer in which the camera hardware may be remotely located at the subject monitoring location. The device 10 generally includes a processor unit 12, a display 14, an interface unit 16, input/output (I/O) hardware 18, a communication unit 20, a camera unit 22, a light unit 24 (which might be optional in some cases), a power supply 26, and memory 28 that stores software programs and data files 30 to 42. In other embodiments, the device 10 may have more or less components but generally functions in a similar manner.

The processor unit 12 may include one processor. Alternatively, there may be a plurality of processors that are used by the processor unit 12, and these processors may function in parallel and perform certain functions. This can be useful for parallel processing of image data from multiple cameras to extract vital signs measurements independently from each camera and/or tracking the field of view on a subject in motion dynamically, using different computing threads, and storing the data into data files. The processor unit 12 controls the operation of the device 10. The processor unit 12 can be any suitable processor, controller or digital signal processor that can provide sufficient processing power depending on the configuration, purposes and requirements of the device 10 as is known by those skilled in the art. For example, the processor unit 12 may be a high performance general processor. In alternative embodiments, specialized hardware can be used to provide at least some of the functions provided by the processor unit 12.

The display 14 can be any suitable display that provides visual information depending on the configuration of the device 10. For instance, the display 14 may be, but is not limited to, a computer monitor, an LCD display, or a touch screen depending on the particular implementation of the device 10. The display 14 generally shows GUIs that a user can interact with to control the device 10 to perform the remote physiological monitoring.

The interface unit 16 includes hardware that allows the processor unit 12 to send and receive data to and from other devices or computers. In some cases, the interface unit 16 can include at least one of a serial port, a parallel port or a USB port that provides USB connectivity. The interface unit 16 can also include hardware for converting received data for later analysis by the processor unit 12. For example, for communicating with the camera unit 22 and the light unit 24, the interface unit 16 may include analog to digital converters (ADCs), digital to analog converters (DACs) and one or more image capture cards. The processor unit 16 may send a control signal to the camera unit 22 to begin recording depth data and/or intensity data and the recorded data may be received by the interface unit 16 and stored at the memory 28 for access by the processor unit 16 for processing the recorded data to measure one or more physiological signal values status.

The input/output (I/O) hardware 18 includes at least one input device and one output device. For example, the I/O hardware 18 can include, but is not limited to, a mouse, a keyboard, a touch screen, a thumbwheel, a track-pad, a track-ball, a card-reader, a microphone, a speaker and/or a printer depending on the particular implementation of the device 10.

The communication unit 20 includes various communication hardware for providing the processor unit 12 with an alternative way to communicate with other devices. For example, the communication hardware may include a network adapter, such as an Ethernet or 802.11x adapter, a modem or digital subscriber line, a BlueTooth radio or other short range communication device, and/or a long-range wireless transceiver for wireless communication. For example, the long-range wireless transceiver may be a radio that communicates utilizing CDMA, GSM, or GPRS protocol according to standards such as IEEE 802.11a, 802.11b, 802.11g, 802.11n or some other suitable standard.

The camera unit 22 includes at least one pair of cameras including an intensity camera and a depth camera. Depending on the implementation of the device 10, the camera unit 22 may be integrated with the device 10 (an example of which is shown in FIGS. 1B and 10) or it may be remote from the device 10. For example, the camera unit 22 may include several pairs of cameras in a multi-FoV arrangement, some examples of which are shown in FIGS. 15A to 17A.

The intensity camera that is used may be near-infrared (NIR) and/or visible light intensity cameras that obtains intensity data that captures continuous reflection changes from the subject and is sent in an intensity channel to the interface unit 16. The reflection intensity changes are due to absorption changes of the blood in the ROIs and may be used to detect Blood Volume Pulse (BVP) through regions of the subject/patient face, such as the forehead and cheeks.

In a depth camera implementation of a stereo camera pair, there are two image sensors with different viewpoint angles that are used to obtain depth data that may be used to obtain depth maps from the subject and may include 3-D depth information that may be used to compensate for subject motion in some embodiments. The depth data is sent in 3-D depth channels to the interface unit 16. The depth channels may be used to record periodic movement of the chest region of the subject/patient due to respiration. Alternatively, or in addition thereto, the depth data may be used to detect subtle head oscillations of the patient/subject due to blood pulsation. In alternative embodiments of the depth camera one may use a time of flight camera (or sensor) with one camera (it has a laser and a sensor), or another configuration such as one camera and one projected pattern to extract depth data. In still other embodiments, any other depth detecting mechanism (i.e., any depth sensor) may be used (i.e., time of flight sensors such as LiDAR) to measure depth data. Accordingly, reference herein to collecting spatial depth data will be understood to refer to detecting depth in any suitable manner using any suitable depth measuring device. However, for ease of description, the remaining discussion will refer to an example case where a depth camera is used to measure spatial depth.

Figure 20:
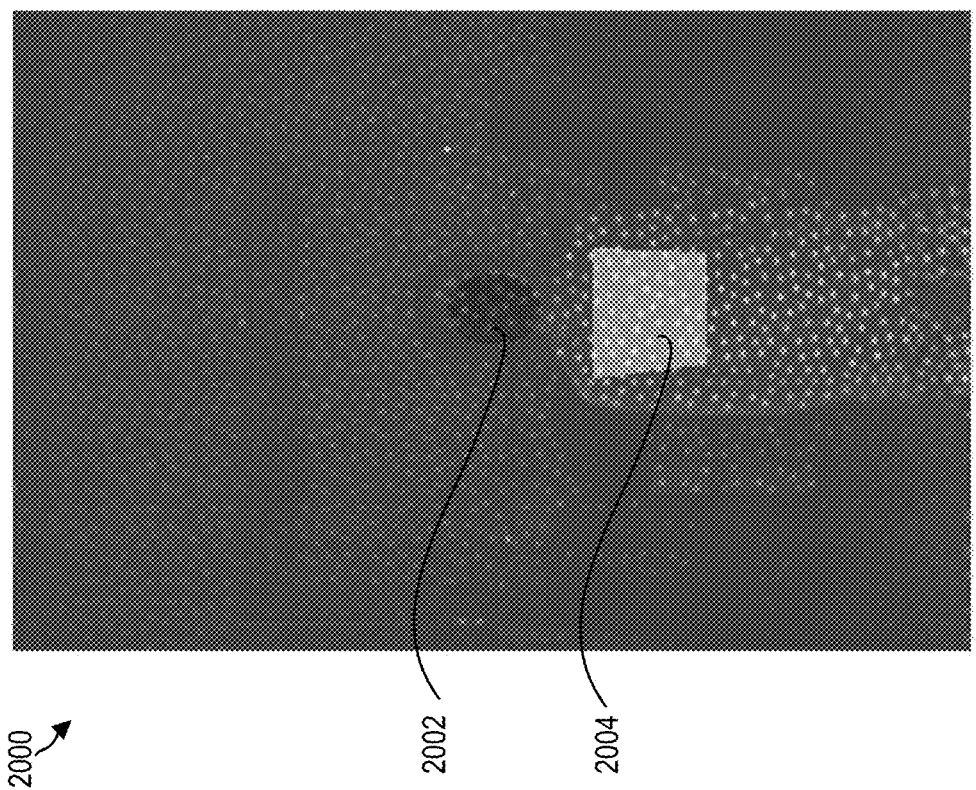
FIG. 20 shows an example image of depth data being acquired of a test subject in low light settings.

The light unit 24 may include one or more light sources, such as LEDs or diode lasers, that may be used to project additional light onto the patient/subject which aids in recording more accurate intensity and depth data. For example, this may be done in situations in which the ambient light is too low (e.g., FIG. 20). Alternatively, the light unit 24 may be used to compensate for changes in ambient light so that illumination of the patient/subject is relatively stable during recording of the intensity and depth data. The light unit 24 may be optional when the camera unit 22 includes light sources that may be projected to the patient/subject.

In at least one example embodiment, the Intel® RealSense™ camera unit (D435, D415, D435i, D455) may be used. The camera unit includes three optical video cameras, including a "right imager" camera, a spaced apart "left imager" camera, an infrared (IR) projector camera (i.e., which may be centered between the left and right imager cameras) and a color sensor. The color sensor provides a visible/NIR intensity channel (i.e., 400-865 nm), the IR projector provides an 850 nm structured light "dot projector" (used for the light source 24 in addition to an optional external light source) and may be optional in some cases, and the right and left imager cameras are used for stereo depth visualization, together with localized computer power to calculate depth maps rapidly and provide intensity and depth maps in 90 frames/sec for full field data and 300 frames/sec for a narrow ~100×800 pixel image data. The light "dot projector" takes light from a laser diode, and passes it through a glass phase element to create a projection of dots on the scene. The two cameras (i.e., left and right), which are used to obtain depth data, are physically separated in space (e.g., by about 50 mm for D415, D435, D435i cameras, and by about 95 mm for D455 camera) and each camera looks at the scene from a slightly different angle so that the recorded depth data can be used to triangulate each pixel and provide a depth estimate. The depth estimate may be provided as a map in addition to the video images from each one of these two cameras. The dot projection on the scene helps with the triangulation and reduces depth estimate errors, which mainly occur in flat objects such as walls. These Intel depth cameras provides depth readouts in ~100 micron depth increments and for averaged ROIs depth changes of that order in magnitude are seen in the processed depth data.

For ease of description, the one or more cameras and/or sensors in a camera unit which are used to generate depth data (i.e., the left and right cameras, as well as in some cases, the IR projector in the Intel® RealSense™ camera unit) may be referenced herein collectively as a "depth camera". Further, cameras and/or sensors in a camera unit which are used to generate intensity data (i.e., the color or RGB sensor in conjunction with one or both of the left and right cameras in the Intel® RealSense™ camera unit) may be referenced herein collectively as an "intensity camera". In view of the foregoing, when reference is made herein to an intensity camera and depth camera, it will be understood that this may in-fact refer to one or more overlapping cameras and/or sensors in the same camera unit, or otherwise, one or more separate cameras and/or sensors in the same camera unit.

Alternatively, in other embodiments, any other video camera can be used to obtain the intensity data, and any depth camera can be used to obtain the depth data as long as the recorded data can be used to determine changes in depth and in intensity due to HR and RR from the subject/patient.

In order to get good intensity and depth data, a camera pair (e.g. intensity and depth) may be calibrated to have the same FoV so that the intensity and depth data can be more easily matched to one another when used to derive the same physiological signal (i.e., HR or RR). There are also some guidelines, based on engineering considerations, to follow for the intensity and depth cameras to have a good signal to noise ratio in the collected data.

For example, for the intensity camera, one or more of the following guidelines may be used to obtain good data: (a) a linear scale is used in converting light to grey levels (i.e., Gamma=1); (b) no automatic gain control; (c) large enough physical pixel size (in microns) to allow enough electrons to be collected in each pixel and to minimize shot noise which is proportional to the square root of the collected electrons count per pixel; (d) high quantum efficiency in converting light to electrons in each pixel; (e) low readout noise electronics to allow for a high signal to noise ratio (SNR); (f) large enough pixel count for each image to allow for good registration and tracking of the various ROIs since with too few pixels, it is challenging to track an ROI of a moving patient/subject; and (g) cameras without color filters (either RGB or infrared cutoff filters) provide more information from the whole spectra and are better suited for quantitative imaging. Furthermore, another guideline to consider for an intensity camera is to have sufficient dynamic range in the intensity data to allow for good data collection and data processing both in low light and large intensity ambient light scenarios. For example, using intensity cameras with 10 bits of information in intensity gray levels (e.g., 1024 grey levels), and with ROI averaging (improves SNR by the square root of N, pixel count) there may be better than 1000:1 dynamic range in the collected intensity data.

As another example, for the depth camera, one should consider that different technologies provide different depth distance mapping and errors. In the short range (currently up to a few meters), a "stereo depth camera" arrangement with two video cameras looking at the scene from different angles provides sub-mm accuracy of depth changes and the ability to measure as close as 30 cm from the object. The error in depth is inversely proportional to the distance between the depth cameras (i.e., typically 50-90 mm) and proportional to the square of the distance to the object. Therefore, if there is a 50 mm distance between the two depth cameras, and if the object is at L=1 meter providing an estimated depth error of 0.2 mm then if the object moves to a distance 2 L (e.g. 2 meters away), the depth error is increased by $L^2$ and the depth error becomes 0.8 mm for an object that is a distance of 2 meters away from the depth cameras. If one wishes to improve accuracy, then the two depth cameras may be spaced apart by a distance of 4d (i.e. 200 mm), which yields a 0.2 mm depth accuracy. In some cases, a projected pattern of light (lines or dots) may be used to help the triangulation for stereo imaging and can either add to, or replace one of the cameras in the stereo camera set.

Alternatively, one may use a "time of flight" depth camera, which is better when there is a larger distance to the patient/subject, and can be much less distance dependent since the time of flight to the patient/subject and back is counted. A time of flight camera may be more feasible when the distance between the depth camera and the subject/patient is more than 3 m.

However, it should also be noted that technology for depth cameras keeps improving and therefore as the depth error gets lower, the range gets larger with short range time of flight designs that can extend from 10 to 40 meters in range. Different depth cameras (or sensors) may be used as long as it is possible to record the small depth changes that come from movement of the body and head of the subject/patient due to HR and RR, as well as depth changes due to overall body movement of a subject who may be, for example, walking or swaying while standing.

The power supply 26 can be any suitable power source that provides power to the various components of the device 10 such as a power adaptor or a rechargeable battery pack depending on the implementation of the device 10 as is known by those skilled in the art. For example, in some cases the power supply 26 may include a surge protector that is connected to a mains power line and a power converter that is connected to the surge protector (both not shown). The surge protector protects the power supply 26 from any voltage or current spikes in the main power line and the power converter converts the power to a lower level that is suitable for use by the various elements of the device 10.

The memory 28 can include RAM, ROM, one or more hard drives, one or more flash drives or some other suitable data storage elements depending on the configuration of the device 10. The memory 28 may be used to store an operating system 30, a remote monitoring application 32, a GUI module 34, a physiological signal measurement module 36, an I/O module 38 and data files 40. The operating system 30 provides various basic operational processes for the device 10. In other embodiments, the software programs may be organized differently but generally provide the same functionality. For example, there may be separate filtering and motion rejection programs that are utilized by the physiological signal measurement module 36.

The processor unit 12 may access the memory 28 to load the software instructions from any of the programs 32 to 38 for executing the software instructions in order to control the device 10 to operate in a desired fashion. The processor unit 12 may also store various operational parameters, calibration data, status data, raw data, processed data, and/or measured physiological signal values (after removing personal data for privacy reasons).

The remote monitoring application 32 comprises software instructions that, when executed, by the processor unit 12 configures at least one processor to operate in a particular manner to implement various functions for the device 10. For example, the remote monitoring application 32 can include program instructions for executing the GUI module 34 for creating a GUI that is shown on the display 16 to allow a user to control and perform remote physiological monitoring, controlling the camera unit 22 and optionally the light unit 24 for recording intensity and depth data, executing the physiological signal measurement module 36 for analyzing the recorded data to obtain one or more physiological signal values and executing the I/O module 38 for retrieving parameters and/or data from the data files as well as storing raw data, processed data and/or physiological signal values in the data files.

The GUI module 34 includes program instructions for providing different GUIs to a user of the device 10 to allow the user to perform various functions such as calibrating the camera unit 22 and the light unit 24, selecting a particular physiological measurement technique which can include using a single camera pair or multiple camera pairs that are in a multi-FoV arrangement, processing the recorded data to obtain redundant physiological values for HR and RR (as explained below), selecting a technique for combining the redundant physiological measurements to generate an overall physiological value for each vital sign that is measured as well as selecting whether motion compensation and/or motion correction is to be performed. The GUI module 34 also includes program code for showing various data to the user including an intensity image of a subject with one or more ROIs, raw recorded intensity and/or depth data, physiological signal waveforms for various vital signs such as HR and RR with or without motion compensation and/or motion rejection.

The physiological signal measurement module 36 includes program instructions that can be used for processing the raw recorded intensity and depth signal data to determine one or more physiological signals for one or more vital signals such as HR and/or RR. For example, the physiological signal measurement module 36 may include program instructions for performing certain methods described herein such as methods 200, 400, and/or 600 in FIGS. 4, 7 and 11, respectively. Such methods may include filtering operations and optionally motion reduction or motion compensate denoising techniques as described herein.

The Input/Output (I/O) module 38 receives input data that was obtained by the interface unit 16 and stores the data in the data files 40, and/or generates outputs data that are then sent to the I/O hardware 18 for output to the user or used by the GUI module 34 as explained previously.

The data files 40 may store any temporary data (e.g., data that is not needed after performing remote physiological monitoring) or permanent data (e.g., data saved for later use), such as subject data (e.g., a subject ID), camera settings, as well as raw and processed recordings. The data files 40 may also include calibration data for the camera and light units 22 and 24 that are used by the device 10.

Referring now to FIGS. 1B and 10, shown therein are front and back views of another example embodiment of a remote physiological monitoring device 50 that is implemented as a tablet having a front surface 52 and a back surface 54. The device 50 includes a GUI 56 that has an image of the patient/subject 58 for which the remote physiological monitoring is being performed. The GUI 56 includes a thermal image 58 along with a temperature reading, a HR waveform 60 and a RR waveform 62. The device 50 includes a light source 24 having two LEDs 64, an IR/depth camera unit 66, a thermal camera 68 and a USB connection 18a. The device 50 may be pointed towards the subject/patient and a start button (not shown) on the GUI 56 may be pressed by the user to being the remote physiological monitoring.

Figure 2:
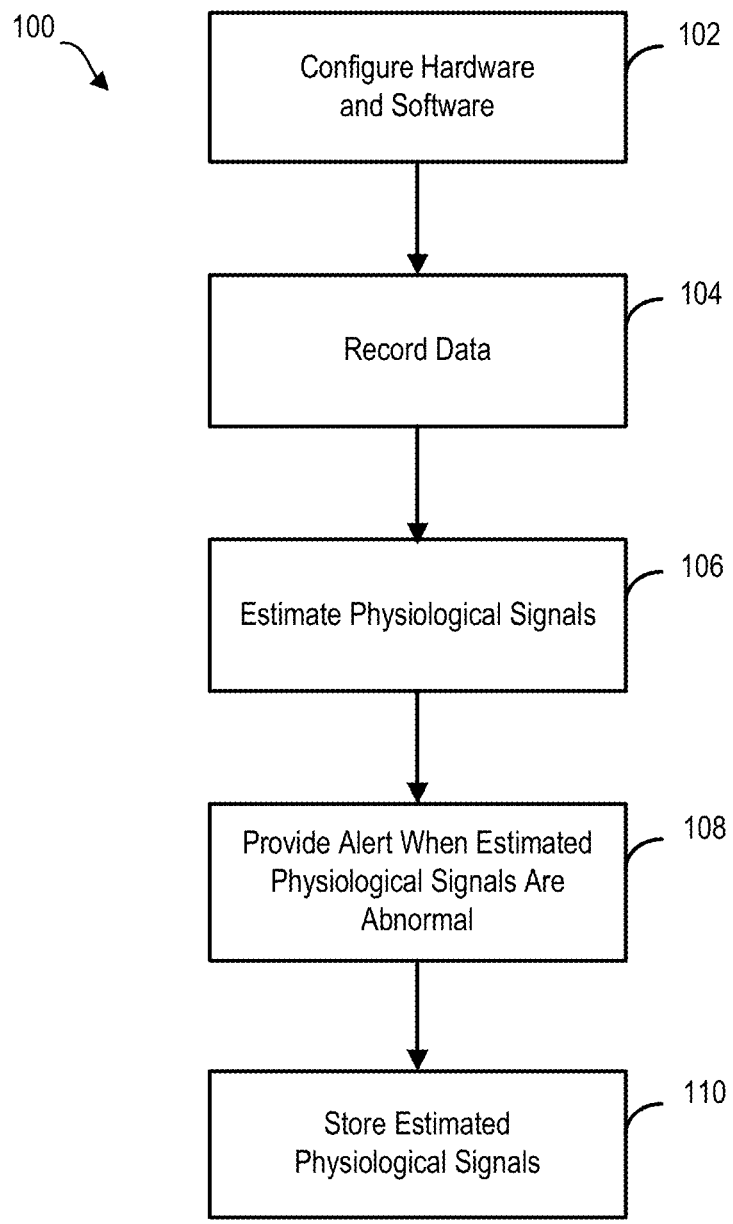
FIG. 2 shows an example embodiment of a remote physiological monitoring method for monitoring physiological signals for a patient, a subject, another individual or an animal.

Referring now to FIG. 2, shown therein is an example embodiment of a remote physiological monitoring method 100 for monitoring physiological signals for a patient, a subject, another individual or an animal. Before the method 100 is started, the patient/subject can be asked to remove any articles of clothing or other items that may cover their face and chest area. The patient/subject is also instructed to enter into the single FoV of the device that is used for performing the remote physiological monitoring or alternatively, into the center of the multi-FoVs when multiple pairs of intensity and depth cameras are used.

Once the patient/subject is ready for recording by the intensity and depth cameras, step 102 of the method 100 involves configuring the hardware and the software for performing the remote physiological monitoring. This can include picking a particular camera arrangement (e.g., single-FoV or multi-FoV arrangement as described later with respect to FIGS. 15A-17A), using intensity and/or depth data for obtaining estimated HR, using intensity and/or depth data for obtaining estimated RR and whether or not to perform motion compensation. For example, if the patient/subject is bed-ridden and may not move much then there may not be a need to perform motion compensation thereby reducing computation.

The method 100 then proceeds to step 104 where the image data is collected from the patient/subject while they stand still or are in motion within the imaging scene (i.e., within the single-FoV or overlap of the multiple FoVs). The collection of the depth and intensity data maybe done in parallel in all available cameras and all FoVs. For example, there may be 3 FoVs provided by three pairs of depth and intensity cameras, for a total of 6 recording streams.

Figure 23:
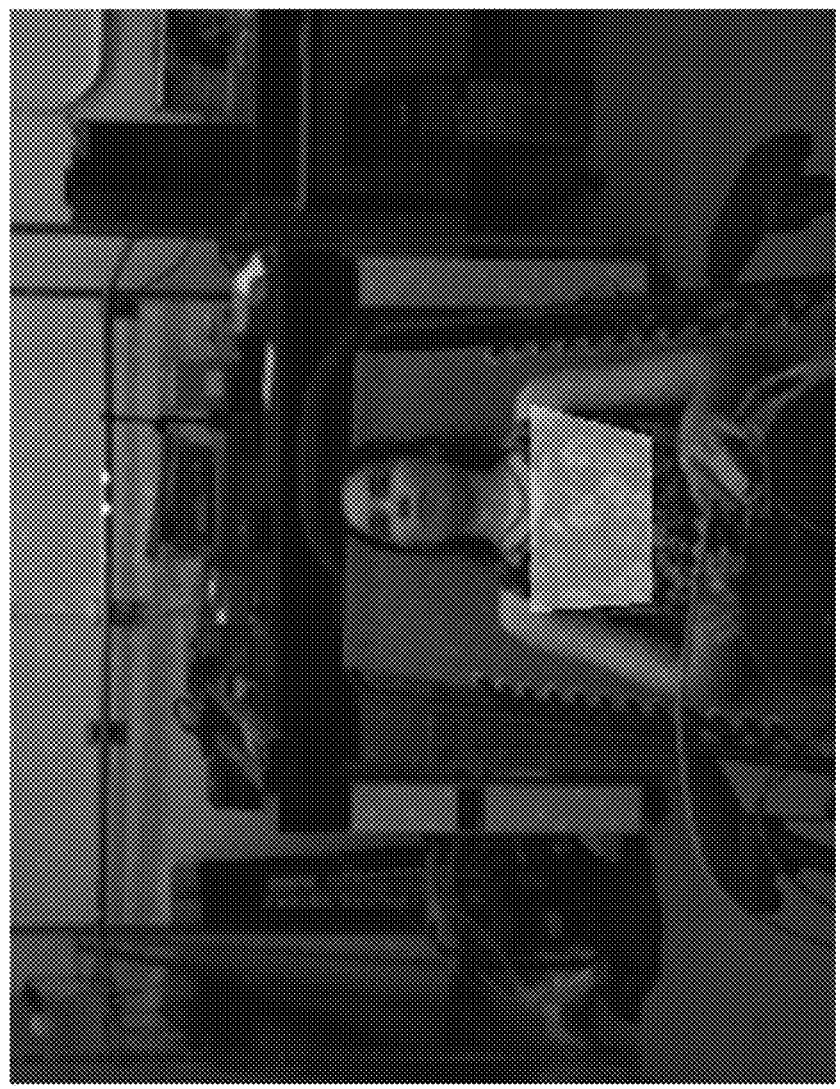
FIG. 23 shows an example image of a test subject in a reclined (or near-supine) position.
Figure 24A:
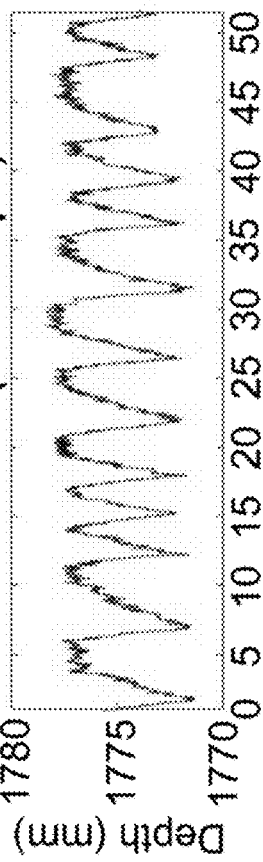
FIG. 24A shows an example of a raw waveform measuring intensity data obtained from an ROI located on the face of a test subject in a reclined position.
Figure 24B:
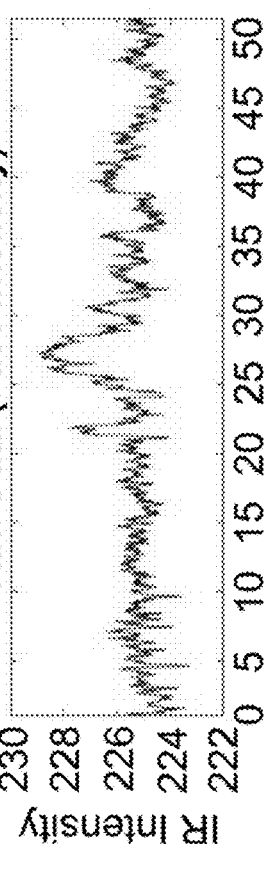
FIG. 24B shows an extracted HR waveform from the waveform of FIG. 24A.

The method 100 then proceeds to step 106 where the recorded intensity and/or depth data are processed to obtain the estimated HR and/or RR physiological measurements values. This may be done using one of several methods such as method 200 in FIG. 4, method 400 in FIG. 7 or method 11 in FIG. 11, for example. At this point there may be data fusion if both of the depth and intensity data are used to both provide estimated HR and RR measurements. This may be done by applying a first set of weights to the HR values obtained from the intensity and depth data across all FoVs and a second set of weights to the RR values obtained from the intensity and depth data across all FoVs (as is described in further detail herein). In other cases, owing to the availability of both intensity and depth data, the appropriate data may be used having regard to the surrounding circumstances. For example, in some cases it may not be possible (or useful) to use the acquired intensity data, in which case the depth data may be used to estimate one or more of RR and HR. For instance, as provided in greater detail herein, this may be the case where a subject is located in low light settings (FIG. 20), in which case the intensity data may not be as valuable as the depth data. In other example cases, it may be appropriate to rely on the intensity data, rather than the depth data, to estimate one or more of RR and HR. For instance, as also explained in greater detail herein with reference to FIG. 23, when a subject is in a "reclined" or a near-supine position—i.e., such as when the subject is lying on a hospital bed—there are may be no observable depth changes from ballistocardiographic forces. In this case, the intensity data may be relied upon for HR and/or RR measurements. In view of the foregoing, the methods provided herein are understood to be flexible to allow using the appropriate data channel (i.e., either the intensity, depth or any combination of the intensity and depth) to estimate RR and/or HR having regard to various circumstances that pertain to the monitored subject and/or the environment around the monitored subject.

The method 100 may then include step 108 which is optional. Step 108 involves generating an "alert" if any of the estimated physiological values for the vital signs are abnormal. For example, the estimated HR may be outside of a normal range and may be too high or too low some in which case the alert can be generated. Alternatively, the estimated RR may be outside of a normal range and may be too high or too low some in which case the alert can be generated. The alert may be an electronic message that is sent to a computer or smart phone of a medical professional or caregiver that is responsible for monitoring the patient. Alternatively, the alert may be a sound that is generated to alert the medical caregiver to attend to the patient. In some embodiments, the alert may be generated when the estimates physiological values are outside of the normal range for a predefined period of time such as 1, 5 or 10 minutes, for example.

The method 100 may then include step 110 which is also optional. Step 110 involves storing the estimates physiological values for the patient/subject. For example, these estimated values may be obtained on an hourly basis or daily for comparison with future and past values to identify trends that suggest the patient may be sick or having certain difficulties.

Figure 3A:
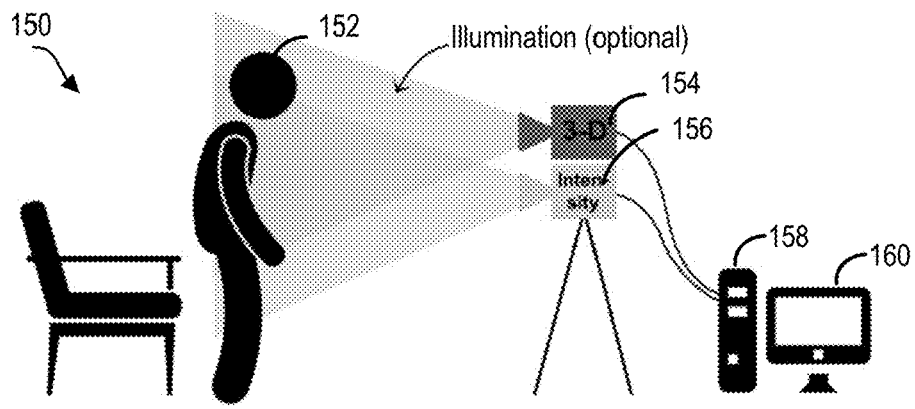
FIG. 3A shows a setup with a single pair of 3D/Intensity cameras with the same field of view (FoV), all controlled and synchronously captured by a computer in which a light source generates light to project a periodic pattern of dots onto the scene, along with other optional forms of illumination.
Figure 3B:
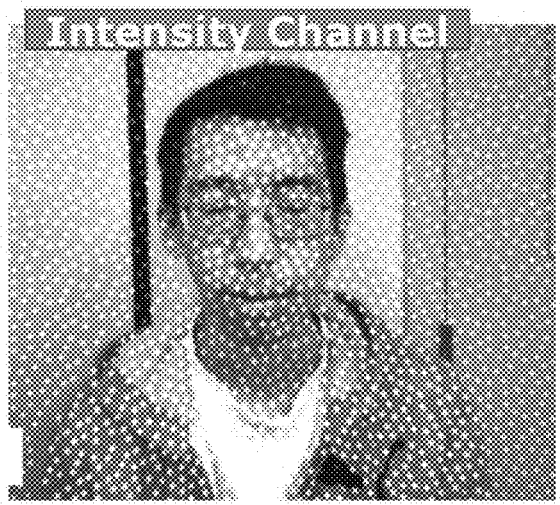
FIG. 3B shows an example of an observed pattern of dots in the video intensity channel of the camera.
Figure 3C:
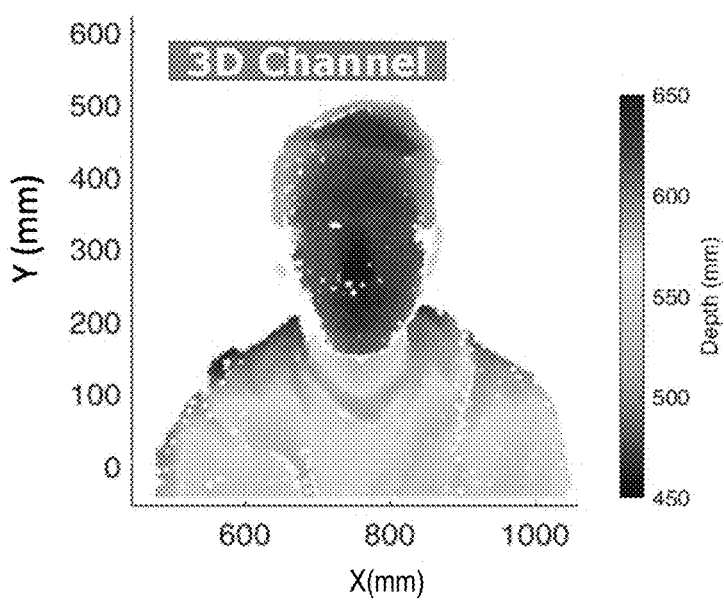
FIG. 3C shows an example of depth information of the scene of FIG. 3B that can be computed using the point cloud coordinates generated from the pattern of dots shown in FIG. 3B.

Referring now to FIGS. 3A-3C, FIG. 3A shows a test setup 150 with a single pair of 3D (e.g. depth) and intensity cameras 154 and 156 with the same FoV, which are both controlled by a computer 158 having a monitor 160 for the synchronous capture of intensity and depth data. In this example embodiment, a projective light pattern is generated which projects a periodic pattern of dots onto the scene, along with other optional forms of illumination, as explained in the description of the device 10 of FIG. 1A. FIG. 3B shows an example of the observed pattern of dots in the intensity channel captured by the intensity camera 156. The intensity camera captures light in the infrared and visible spectra of light, with each pixel in an image having a value proportional to the amount of light collected from that part of the scene. FIG. 3C shows an example of depth information of the scene of FIG. 3B that can be computed using the point cloud coordinates generated from the pattern of dots shown in FIG. 3B and the depth data provided by the 3D camera 154. Using the pattern of dots is one way to create a high accuracy depth map of a scene. Alternatively, it should be understood that depth information can be created by the depth camera, even when there is no pattern of dots, just by a triangulation of 2 views from the stereo camera pair, or by another type of depth camera such as a Time of Flight camera. In some embodiments, the depth map can also be calculated using the stereo vision afforded by two different camera sensors separated by a certain distance apart.

While the intensity and depth cameras 154 and 156 can both record image data with a frame rate as high as 300 FPS, the frame rate in the data shown in FIGS. 3B and 3C is typically set at 30 FPS, and each channel has a resolution of 1280×800 pixels. Face detection algorithms automatically track the subject's face and triangulate regions of interest (ROI) such as, for example, the forehead and cheeks (not shown). Two sets of physiological measurements can be collected from the subject using these 2 channels (i.e. intensity and depth) of data: the HR, and the RR.

Intensity-Based HR and RR Measurements

Figure 4:
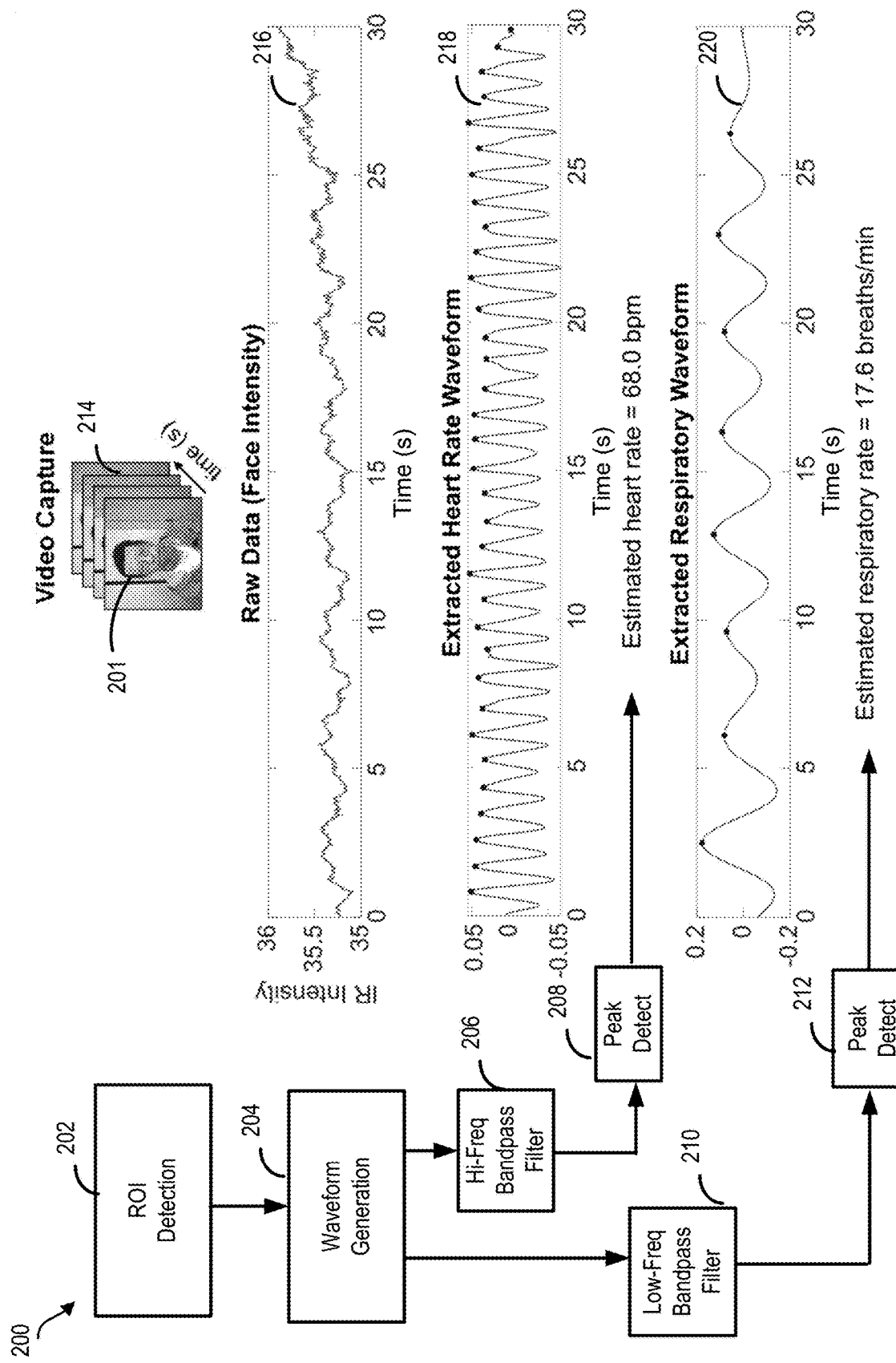
FIG. 4 shows an example embodiment of a first method for estimating Heart Rate (HR) and Respiratory Rate (RR) using intensity data during remote physiological monitoring.

Referring now to FIG. 4, shown therein is an example embodiment of a first method 200 for estimating Heart Rate (HR) and Respiratory Rate (RR) using intensity data during remote physiological monitoring. Changes in reflected light intensity from selected ROIs 201 on the face of the subject/patient face correspond to changes in blood volume and, consequently, the HR (this may be referred to as a PPG signal). At the same time, respiratory-related fluctuations from the PPG signal (i.e. intensity changes) reveals the RR of the subject/patient.

Step 202 involves analyzing the recorded intensity data to track the face of the patient/subject using a facial-recognition and tracking algorithm such as, but not limited to, the Viola-Jones method, for example. In at least one embodiment, the facial tracking may be implemented using the OpenCV (open source code) module for Face recognition. OpenCV stands for Open Source Computer Vision and it is a computer vision library started by Intel in 1999. This library provides real-time image processing algorithms that may be used on various platforms. Alternatively, OpenCV 2.3.1 may be used which has a programming interface for C, C++, Python and Android. Alternatively, OpenCV 2 which has a FaceRecognizer class for facial recognition may be used (see docs.opencv.org/2.4/modules/contrib/doc/facerec/facerec_tutorial.html which is incorporated herein by reference in its entirety).

Step 202 also involves determining the ROIs on the faces identified for each intensity image. The ROIs may include the whole face, the forehead, the cheeks or the neck of the patient/subject. Each of these ROIs is useful for estimating the HR and the RR. The techniques to find the ROI may be based on first extracting landmarks for a subject. For example, facial landmarks may be used such as eyes, nose, lips, or ears. For other ROIs, other body landmarks may be used such (hands, arms, shoulders, head, hips, knees, feet, or the spine. Once the one or more landmarks are identified them in the intensity image, the ROI size and location may be defined, based on the relative distance between the identified landmarks and their location in the intensity image. With a moving body, as described in further detail below, the location of the landmarks may be updated over time, and with it, the location of the ROIs are also updated.

For example, once the location of the eyes is found, a rectangle ROI may be created in the forehead region, above the eyes, in a distance equal to the spacing between the eyes and the nose, and in a width that is the distance between the two eyes. As another example, fora chest-based ROI, once the locations of the shoulders and the hips are found, a trapezoidal ROI may be created between the shoulders and the midway point to the hips, with a height that reaches half the distance between the height of the shoulders and the height of the hips.

Step 204 involves, for each video frame (i.e. image), determining the mean pixel value inside the ROI and then creating a mean ROI pixel waveform which is a time series of the mean ROI pixel values obtained from the various images. This may be plotted. An example of this is waveform 216.

Steps 206 and 208 are then performed for determining the HR. At step 206, the mean ROI pixel waveform 216 is filtered by applying a "higher frequency Bandpass filter" (Hi-Freq Bandpass), which is a bandpass filter with a passband typically from about 1 Hz to about 2.16 Hz (corresponding to 60 to 130 BPM), to generate a filtered waveform 218. Step 208 then applies peak detection on the filtered waveform 218.

These peaks are shown as dots on the filtered waveform 218. The instantaneous heart rate may then be estimated by determining $$\frac{1}{\Delta THR},$$

where ΔTHR is the time difference between the adjacent identified peaks in the filtered waveform 218. Physiologically, the HR is at a 'higher-frequency' compared to the RR. The estimated HR in Hz is converted to BPM by multiplying by 60 s/min. In this example, the estimated HR is 68 BPM.

Steps 210 and 212 are then performed for determining the RR. At step 210, the mean ROI pixel waveform is filtered by applying a lower frequency Bandpass filter' (Lo-Freq Bandpass), which is typically a bandpass filter with a passband from about 0.15 to 0.33 Hz (or 9-20 BrPM) to obtain a filtered waveform 220 which may be called a respiratory waveform. Step 212 then applies peak detection on the filtered waveform 220. These peaks are shown as dots on the filtered waveform 220. The instantaneous RR may then be estimated by determining $$\frac{1}{\Delta TRR},$$

where ΔTRR is the time difference between the adjacent identified peaks in the filtered waveform 220. The estimated HR in Hz is converted to BrPM by multiplying by 60 s/min. In this example, the estimated RR is 17.6 BrPM.

The estimated HR and RR derived values using the method 200 for various intensity data were compared to the clinical standard, which was implemented using an electrocardiograph from the General Electric Dash Patient Monitor. There was typically an observed a mean square error (MSE) of about 2% when the patient was stationary and under interior room lighting.

It should be noted that the peak detection methods used in steps 208 and 212 may be based on methods known to those skilled in the art. For example, using MATLAB™, the peak detection may include a few steps such as: correcting for long term drift intensity by subtracting a moving average of the filtered waveform, normalizing the waveform to have a span between (−1,1) (this might be done by applying the scaling factor (x_value(t)−mean_x_value)/standard_deviation_x_value to each value (e.g. x_value) in the filtered waveform), fitting a spline curve to the normalized data, and finding local maxima by using the Find peaks MATLAB™ function.

Depth-Based HR Measurements

The cyclical movement of blood from the heart to the head causes the head to sway back and forth (~1 mm) in a periodic way. By monitoring the motion of the head of the patient/subject with the depth camera, one can track this motion and obtain the HR from this motion. In the example that follows, the ROI was chosen to be the forehead, and the average depth value in this ROI was calculated for each depth video frame (i.e. each depth image), to produce a spatially-averaged depth waveform 250, an example of which is plotted versus time in FIG. 3A. From physiology, one can expect these values to change, due to the pulse of the patient/subject. These averaged values may be done for a given time period such as 30 seconds, for example. As described previously, other ROIs may be used for the head (e.g., neck, cheeks, or whole face) and body of the patient/subject (e.g. upper chest and lower chest) and the ROIs can be found using appropriate landmarks as previously described.

The method 200 may then be used starting with the spatially-averaged depth waveform 250 where the ROI is the forehead of the patient/subject and a spatially-averaged depth waveform 254 where the ROI is the chest of the patient/subject (see waveform 254 in FIG. 5C). The filtered HR waveforms 252 and 256 for the forehead and chest ROIs are shown in FIGS. 5B and 5D respectively along with the local peaks (indicated by dots) for each of these waveforms. In these examples, the estimated HR, from peak detection, is about 72 BPM (74.5 BPM) for the forehead (chest) ROI, and differ from each other by less than 3%.

It can be seen that the intensity-based HR waveform (FIG. 5E), taken at the same time from the subject, correlates well with the depth-based method of HR monitoring (FIGS. 5B and 5D). The application of both intensity-based and depth-based approaches, along with the observed strong correlation between them, allows for the measurement of the HR of a subject/patient that is independent of illumination conditions.

In addition, the inventors found that the face area, and in particular the forehead area, seems to move back and forth more compared to the chest. For example, see the magnitude of change in the extracted HR from the face depth changes in FIG. 5B, as compared to the extracted rate from the chest depth changes in FIG. 5D.

In an alternative embodiment, for generating the spatially averaged waveform for the ROI, rather than just applying averaging to the pixel values in the ROI another method may be to use different weights for different areas within the ROI, or to define a few ROIs, such as the forehead, cheek left, and cheek right when the ROI is determined from at least a portion of the face of the patient/subject and then calculate the spatial average for each ROI separately and then create a "combined" spatially averaged pixel value where the weight of each ROI may not be equal. For example, more weight may be given to the forehead ROI. This may be done for ROIs on intensity-based image data and depth-based image data.

Respiratory Rate (RR)—Depth

In accordance with the teachings herein, the RR may be determined by looking at temporal changes in depth values taken from 2 or more different ROIs on image data from the depth channel. For example, the temporal changes may capture subtle back-and-forth head movements that can be observed from the forehead; and/or back-and-forth movements of the chest of the patient/subject, which may be triangulated from the face ROI of the patient/subject or defined using other approaches such as skeletal tracking, which expands and contracts with each breath.

The skeletal tracking may be implemented in various ways such as, but not limited to, using a Machine Learning (ML) approach with neural networks to identify and mark skeletal landmarks. For example, CubeMos, which is a Software Development Kit (SDK) (cubemos.com) may be used, which is based on a deep learning version of a neural network in ML (e.g., intelrealsense.com/skeleton-tracking/). Alternatively, the CMU Robotics OpenPose ML-based software may be used for pose tracking (e.g., see github.com/CMU-Perceptual-Computing-Lab/openpose, ri.cmu.edu/publications/openpose-whole-body-pose-estimation/, or arvrjourney.com/human-pose-estimation-using-open pose-with-tensorflow-part-1-7dd4ca5c8027). Alternatively, a database of human poses provided by the Max Plank institute may be used for testing different algorithms that are developed for human pose estimates, and finding landmarks (e.g., see human-pose.mpi-inf.mpg.de/#overview). The documents associated with these various software applications are herein incorporated by reference in their entirety.

Figure 6A:
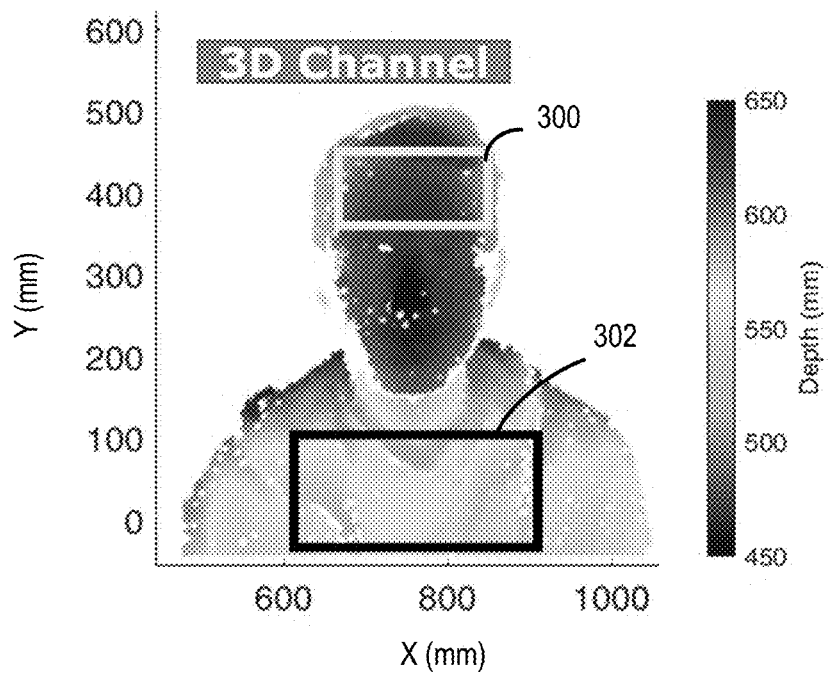
FIG. 6A shows an example of the depth channel output of the 3-D sensing camera where both the forehead and chest ROIs are selected.
Figure 6B:
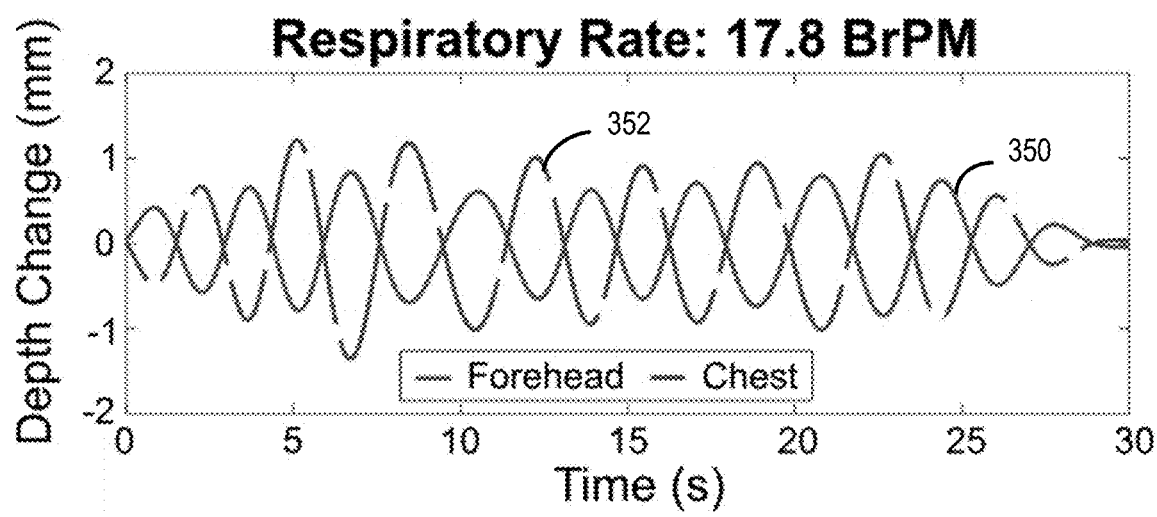
FIG. 6B shows the RR waveforms obtained from both ROIs of FIG. 6A using the method shown in FIG. 4.

In another example embodiment the process of extracting filtered HR and RR waveforms from depth map changes can be repeated for different ROIs, such as for example, a forehead ROI 300 and a chest area ROI 302, (see FIG. 6A). A correlation of these two sources of information relative to one another is shown in FIG. 6B. It can be seen that both depth-change waveforms are well correlated, and provide estimated RR values that are within 0.1 BrPM of one another. The inventors have generally found that the RR elucidated from these two different ROIs have typically been found to be within 2% of the clinical standard.

Figure 9A:
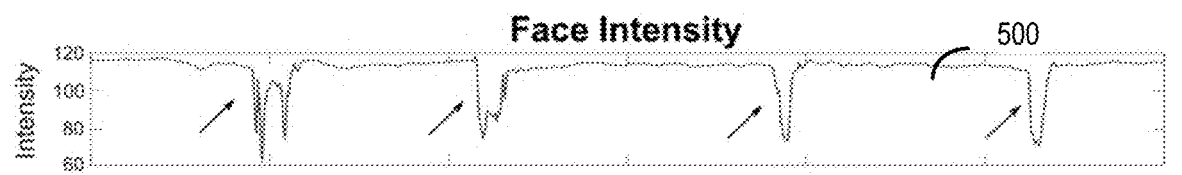
FIG. 9A shows an example of average intensity values from a test subject's forehead ROI plotted against time.
Figure 9B:
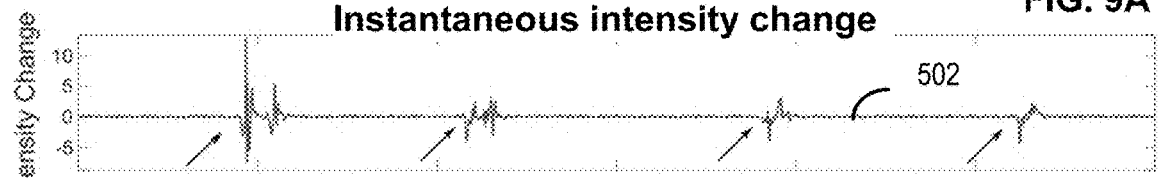
FIG. 9B shows test subject motion being detected by looking at large instantaneous velocities of the subject's ROI on their face, cheeks, forehead or chest (~tens of cm/s).
Figure 9C:
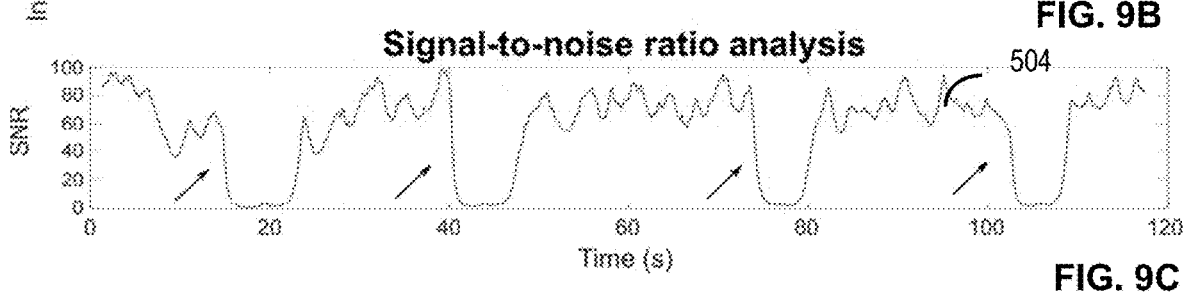
FIG. 9C shows how a drop in the signal-to-noise ratio (SNR) of the HR corresponds to the large instantaneous velocities of FIG. 9B.
Figure 9D:
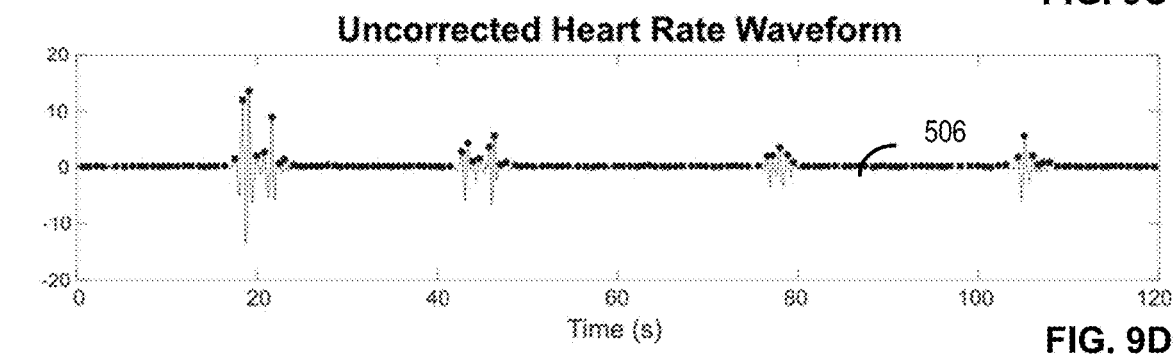
FIG. 9D shows an example of the HR waveform derived from the intensity waveform of FIG. 9A without motion removal.
Figure 9E:
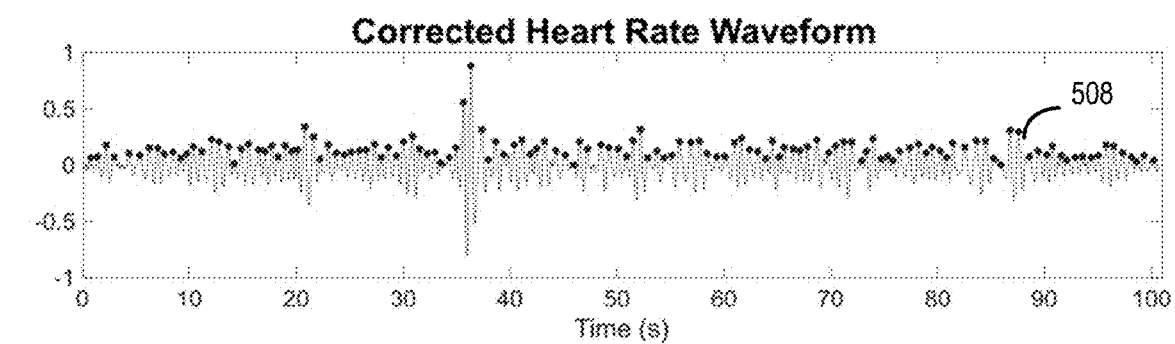
FIG. 9E shows an example of the HR waveform derived from the intensity waveform of FIG. 9A with motion removal.

In another example embodiment, depth data sets can be collected for both ROIs (chest, forehead) simultaneously and then the depth data set that has a lower SNR can be discarded with respect to the other depth data set (FIG. 9C shows examples of SNR for portions of a waveform). In addition, if the scene is too dark then the depth-based measurements may be used for estimating the vital signs.

Figure 7:
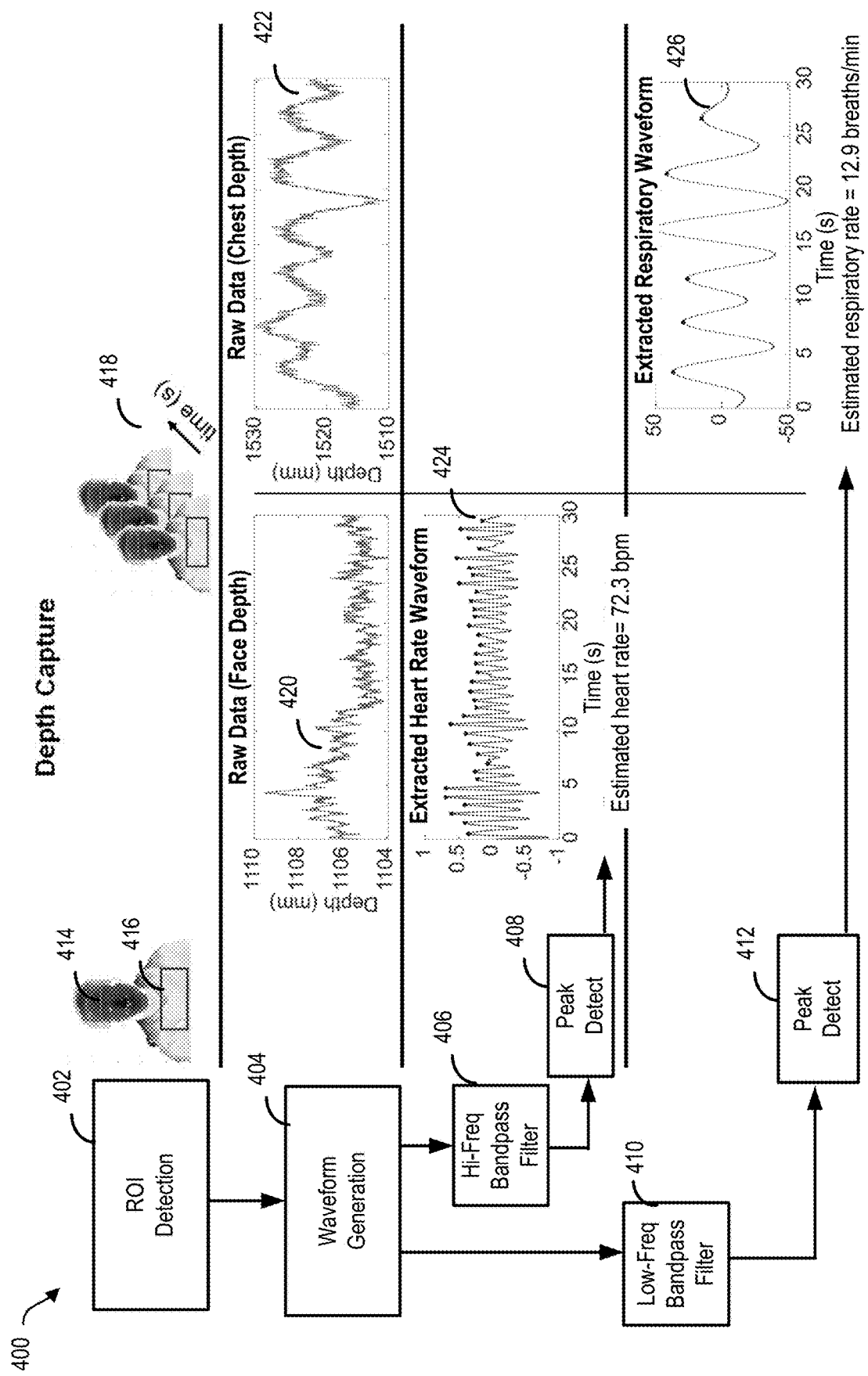
FIG. 7 shows an example embodiment of a second method for estimating Heart Rate (HR) and Respiratory Rate (RR) using depth data during remote physiological monitoring.

Referring now to FIG. 7, shown therein is an example embodiment of a second method 400 for estimating Heart Rate (HR) and Respiratory Rate (RR) using depth data during remote physiological monitoring. At step 402, the body of the subject/patient is tracked across successive depth video images 418 using a skeletal-recognition and tracking algorithm as described earlier. ROIs, such as a forehead ROI 414 and a chest ROI 416, are then determined on each of the depth video images using landmarks that are based on the tracked body in each of the depth video images. At step 404, for each depth video frame, the mean pixel value inside each ROI 414 and 416 is obtained as a time series. These mean ROI waveforms can be plotted as a function of time to generate raw data waveforms 420 and 422, corresponding to the forehead and chest ROIs 414 and 416, respectively.

Steps 406 and 408 are then performed to determine the HR waveform 424. At step 406, the mean ROI pixel waveform 420 is filtered by applying a 'higher frequency Bandpass filter (Hi-Freq Bandpass), which is a bandpass filter with a passband typically from about 1 Hz to about 2.16 Hz (corresponding to 60 to 130 BPM), to generate the filtered waveform 424. Step 408 then applies peak detection on the filtered waveform 420 to obtain the dots shown on waveform 424. The previously described peak detection methods can be used. The instantaneous HR may then be estimated by determining $$\frac{1}{\Delta THR},$$

where ΔTHR is the time difference between the adjacent identified peaks in the filtered waveform 424. Physiologically, the HR is at a 'higher-frequency' compared to the RR. The estimated HR in Hz is converted to BPM by multiplying by 60 s/min. In this example, the estimated HR is 72.3 BPM.

Steps 410 and 412 are then performed to determine the respiratory waveform 426. At step 410, the mean ROI pixel waveform 422 is filtered by applying a lower frequency Bandpass filter (Lo-Freq Bandpass), which is typically a bandpass filter with a passband from about 0.15 to 0.33 Hz (or 9-20 BrPM) to obtain a filtered waveform 426 which may be called a respiratory waveform. Step 412 then applies peak detection on the filtered waveform 426. The detected peaks are shown as dots on the filtered waveform 426. The previously described peak detection methods can be used. The instantaneous RR may then be estimated by determining $$\frac{1}{\Delta TRR},$$

where ΔTRR is the time difference between the adjacent identified peaks in the filtered waveform 426. The estimated HR in Hz is converted to BrPM by multiplying by 60 s/min. In this example, the estimated RR is 12.9 BrPM.

Motion Robustness from the Depth Channel (Single FoV)—Selective Frame Rejection

In accordance with another aspect of the teachings herein, motion compensation may be implemented using a single FoV setup and example waveforms shown in FIGS. 8A-8E illustrate this principle. FIG. 8A shows an example of average distance of a test subject's chest ROI from a depth camera plotted against time as waveform 450. Motion can then be 'sensed' by observing the test subject's instantaneous velocity as shown by waveform 452 in FIG. 8B, which may be calculated directly from temporal changes in the depth values of the waveform 450. Test subject motion may be detected by looking for large instantaneous velocities of the test subject's chest ROI position (~tens of cm/s). FIG. 8C shows an example of how the signal-to-noise ratio (SNR) of the chest depth measurements drop in correspondence with the occurrence of large instantaneous velocities of the chest depth changes in FIG. 8B. By removing the portions of the chest depth waveform 450 where there is motion (see FIG. 8D without this removal vs. FIG. 8E with this removal) once can gain a dramatic improvement in the accuracy of the estimated RR value. In this example, the test subject has timed their breathing to be 12 BrPM, while the estimated RR without using motion compensation is 20.8 BrPM and the estimated RR with using motion compensation is 11.6 BrPM. Accordingly, the amount of error experienced in estimating the RR value from the uncorrected respiratory waveform (FIG. 8D) can also be quantified in terms of the signal to noise ratio (SNR) in FIG. 8C. The SNR is the ratio of the power spectral density of the RR frequency spectrum to out-of-band frequencies. In this example, once the SNR value drops below 20, the accuracy of the estimated RR degrades.

In performing the movement compensation shown in FIG. 8E, one can decide on a criteria and threshold for removal, such as instantaneous chest velocity >100 mm/sec and/or SNR value <20, for example. Accordingly, waveform segments that have a high instantaneous velocity or a low SNR (relative to the rest of the waveform) are removed where this may be determined using a range of "normal" velocities through test cases. Alternatively the threshold for instantaneous chest velocity may be set empirically. For example, in each situation, the subject/patient may walk or move slower or faster, and this will correspond to different values for velocity thresholds so the threshold for instantaneous value may be set for each scene.

As segments of the waveform are analyzed using these criteria, if the criteria are true for any waveform segments then those waveform segments are removed. Interpolation may then be used to rejoin waveform segments that are before and after a removed waveform segment. Alternatively, the time points of waveform segments that are before and after a removed waveform segment may just be directly connected without interpolation. This may be suitable if it is assumed that motion events are infrequent enough to not have a strong effect on the final estimated RR once those segments are removed.

Motion Robustness from the Intensity Channel (Single FoV)—Selective Frame Rejection Motion compensation using a single FoV setup and recording data from the intensity channel are shown in FIGS. 9A-9E. For each video frame, the mean pixel value inside the ROI of the test subject's face is obtained and plotted as a function of time. For example, the average intensity values from the forehead ROI area (i.e., 'Face Intensity', see FIG. 9A) is recorded as waveform 500. Motion can then be 'sensed' by observing the subject's instantaneous intensity change (i.e., 'Instantaneous intensity change', see FIG. 9B), which is calculated directly from temporal changes in the intensity values of waveform 500 to generate waveform 502. Chest and forehead ROI have large instantaneous velocity changes when a person moves. In cases where the chest movement is larger, the motion detection may be done using the chest ROI, and applied to identifying when to reject frames of waveform segments for the corresponding upper ROI of the face. Accordingly, smaller changes may happen when plotting forehead ROI velocities Similar to the previous calculation of the waveform SNR for the Depth channel, the amount of error experienced in obtaining the HR from the uncorrected intensity waveform can also be quantified in terms of the SNR (see the waveform 504 in FIG. 9C). The SNR is the ratio of the power spectral density of the HR frequency spectrum to out-of-band frequencies. By removing the portions of the face intensity waveform 500 where there is motion (see FIG. 9D without motion correction vs FIG. 9E with motion correction) an improvement in the accuracy of the estimated HR is achieved. Taking the estimated HR from the waveform 508 with motion removal (about 80.2 BPM), and comparing it to the estimated HR from the waveform 506 without motion removal (about 78.3 BPM), and taking into account that the motion time was about ~16% of the total observed time, it suggests that the estimated HR during the motion segments deviated by 14%, and by removing these segments of the waveform 500, the accuracy of the intensity-based HR measurements was improved. This motion compensation is expected to also improve the accuracy of depth-based HR measurements as well by adding motion compensation to the method 400 of FIG. 7.

Figure 10B:
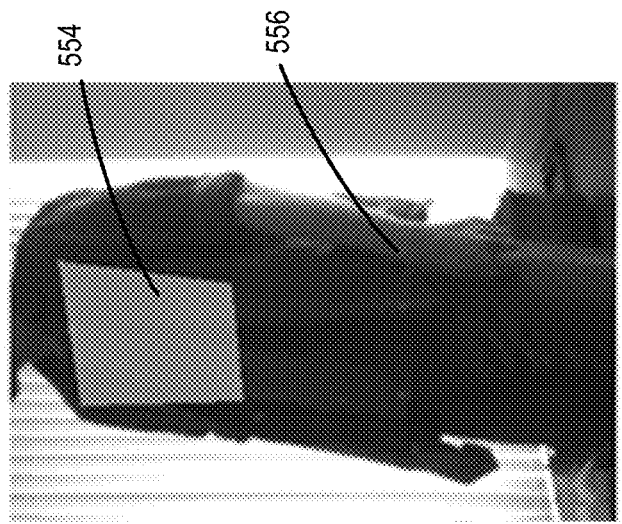
FIGS. 10A-10B show how skeletal tracking allows to change, for example, the chest ROI (indicated in the parallelogram) as the positioning and posture of the test subject within the FoV of the camera changes.
Figure 10A:
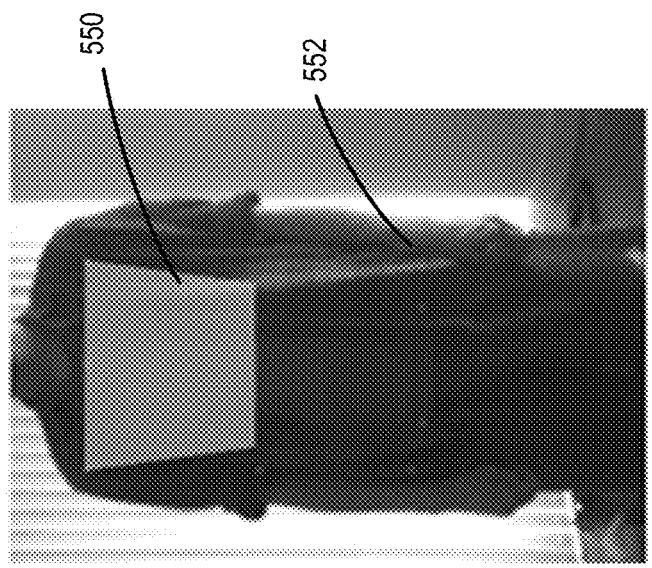

In accordance with another aspect of the teachings herein, skeletal tracking can be used in performing motion compensation for estimating remotely monitored physiological signal values. Skeletal tracking provides another way to dynamically localize the various ROIs (e.g., forehead, cheeks, chest, abdomen, etc.) in the intensity-based and depth-based images. Furthermore, the ROI size can be changed to reflect different skeletal postures such as, but not limited to, when the subject/patient does not face the cameras directly. An example of this is shown in FIGS. 10A-10B which illustrate how skeletal tracking allows the chest ROI to change (indicated by different parallelograms 550 and 554) as the positioning and posture of the test subject changes within the FoV of the camera. Skeletal tracking allows for more accurate motion compensation by continuously updating the ROI as the subject moves within the camera frame.

The skeletal tracking can be used to identify landmarks—i.e. several points of the torso (e.g. see dots 552 in FIG. 10A vs. dots 556 in FIG. 10B) in order to update the ROI over time. By lining up the dots the ROI can be created. For example, the chest ROI is determined based on four coordinate points: the two shoulders and the two hip joints. As the subject/patient moves closer to or farther away from the camera, these four points will automatically lead to an ROI that is larger or smaller, respectively. The skeleton coordinates may be generated using an appropriate tracking software package such as the Skeleton Tracking SDK by Cubemos mentioned earlier.

Figure 11:
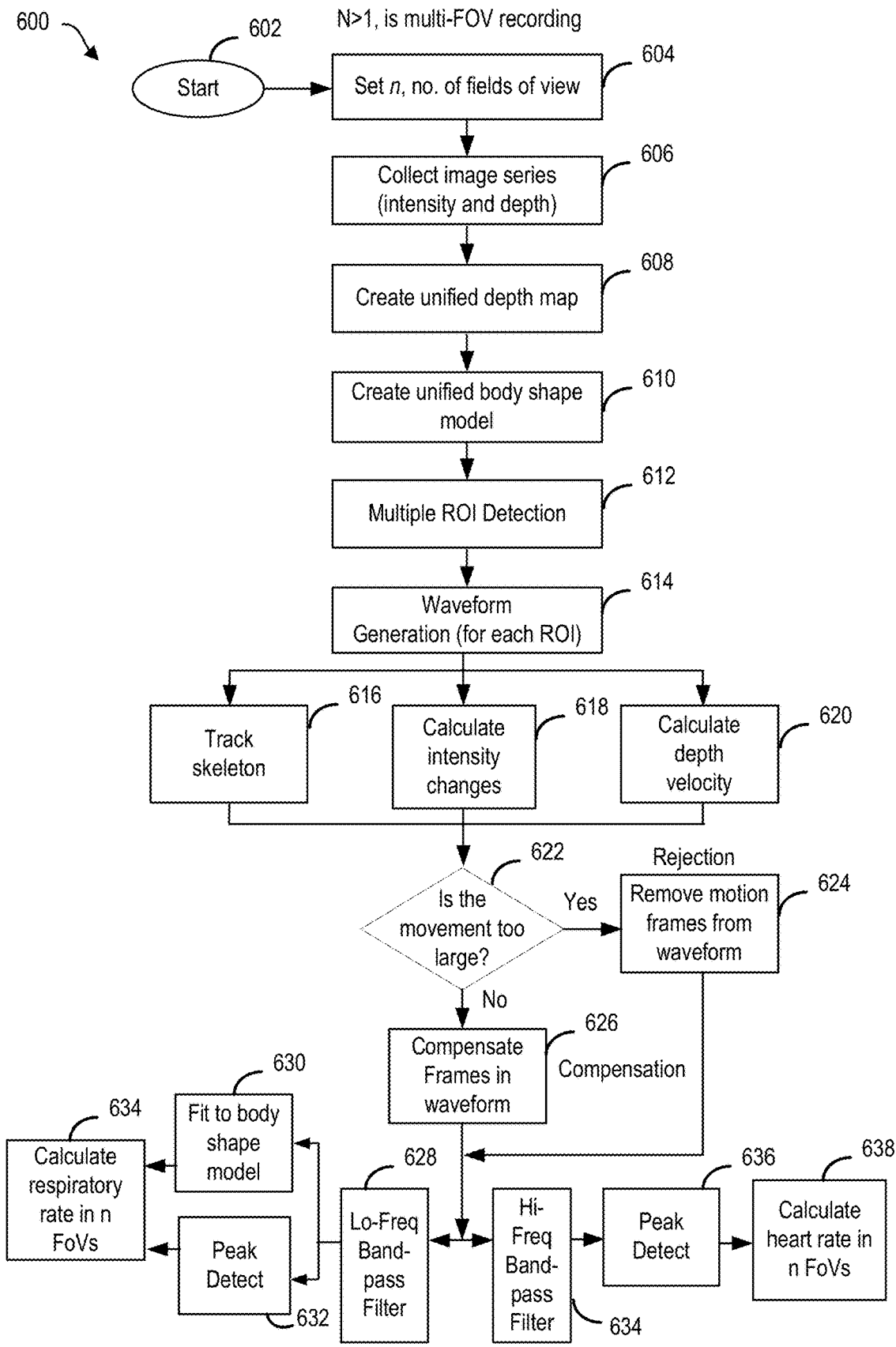
FIG. 11 shows an example embodiment of a third method for remote monitoring of physiological signals which incorporates motion compensation or motion rejection.

Referring now to FIG. 11, shown therein is an example embodiment of a third method 600 for remote monitoring of physiological signals which incorporates motion compensation or motion rejection which may be performed on single-FoV or multi-FoV camera arrangements. The method 600 may be used for both single FoV and multi-FoV arrangements. Movement of the patient/subject is tracked using a series of video frames, e.g. video images, which are taken at a certain interval, such as ~1 second intervals. In general, incoming data from instantaneous velocity calculations and skeletal tracking will be continuously processed to detect motion events. Upon detection of a motion event, the severity of the motion is used to determine the correction that is applied. If the movement is relatively minor (e.g. stretching), motion compensation techniques (discussed below) will be used to preserve the physiological information. However, larger movements necessitate the use of motion rejection, in which the sections of data that are compromised by motion are discarded (as discussed previously in FIGS. 8A-8E and 9A-9E). Compensation on both intensity and depth channels may be performed.

The method 600 begins at step 602. At step 604, the number n of FoVs is setup for the camera arrangement(s). Each of the n FoV arrangements will typically have both a depth camera and an intensity (video) camera. However, in some embodiments, it is possible that at least one of the n FoV arrangements may have just a single camera (i.e. an intensity camera or a depth camera).

At step 606, the image data is collected as a series of video frames for intensity and/or depth based on the types of cameras that are used in the multi-FoV arrangements. The depth and/or intensity image data is collected for each FoV.

Figure 18:
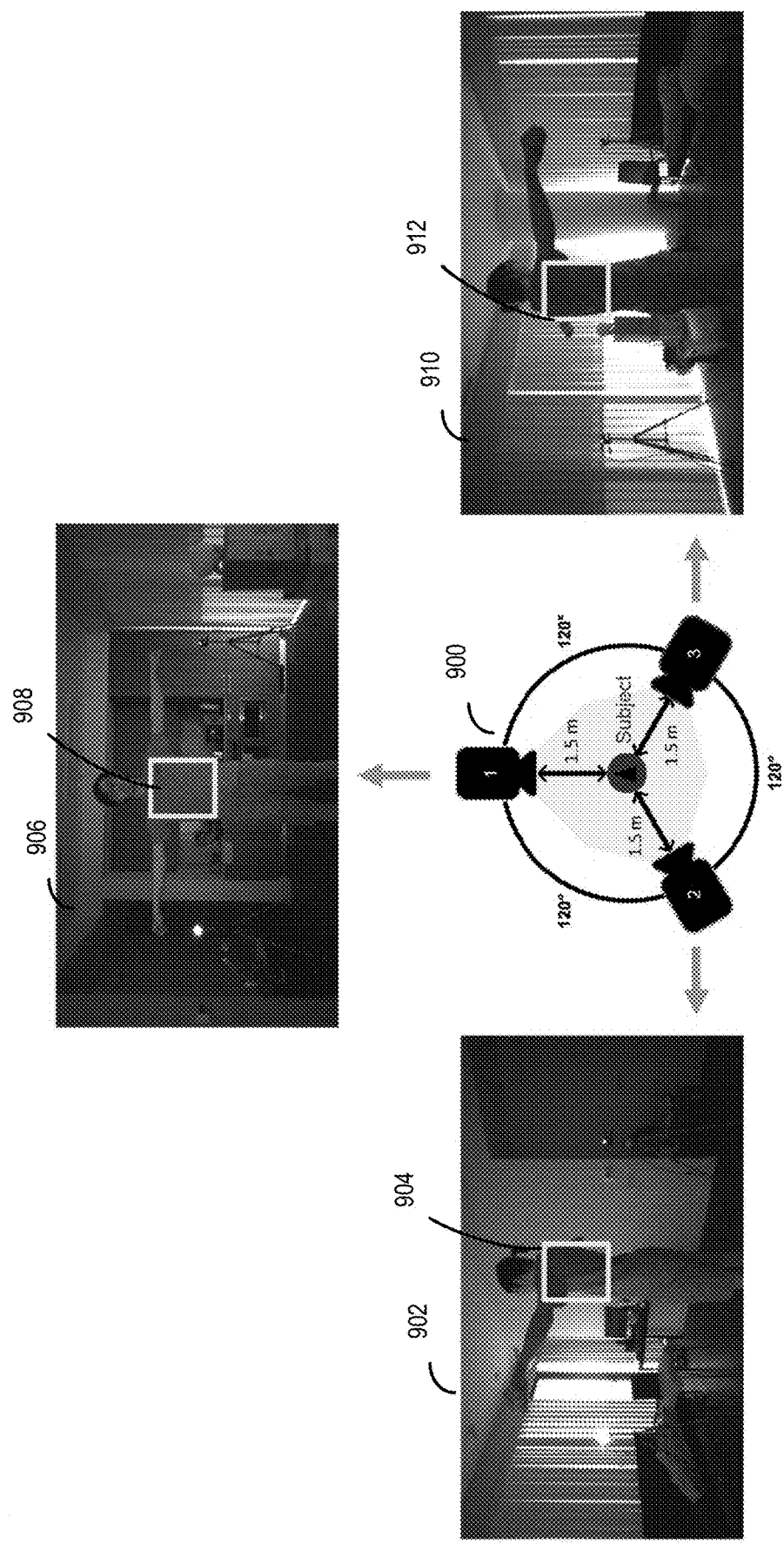
FIG. 18 shows another example of an experimental setup for performing motion compensation using a multi-FoV camera pair arrangement using three cameras as well as example scenes with ROIs.
Figure 19:
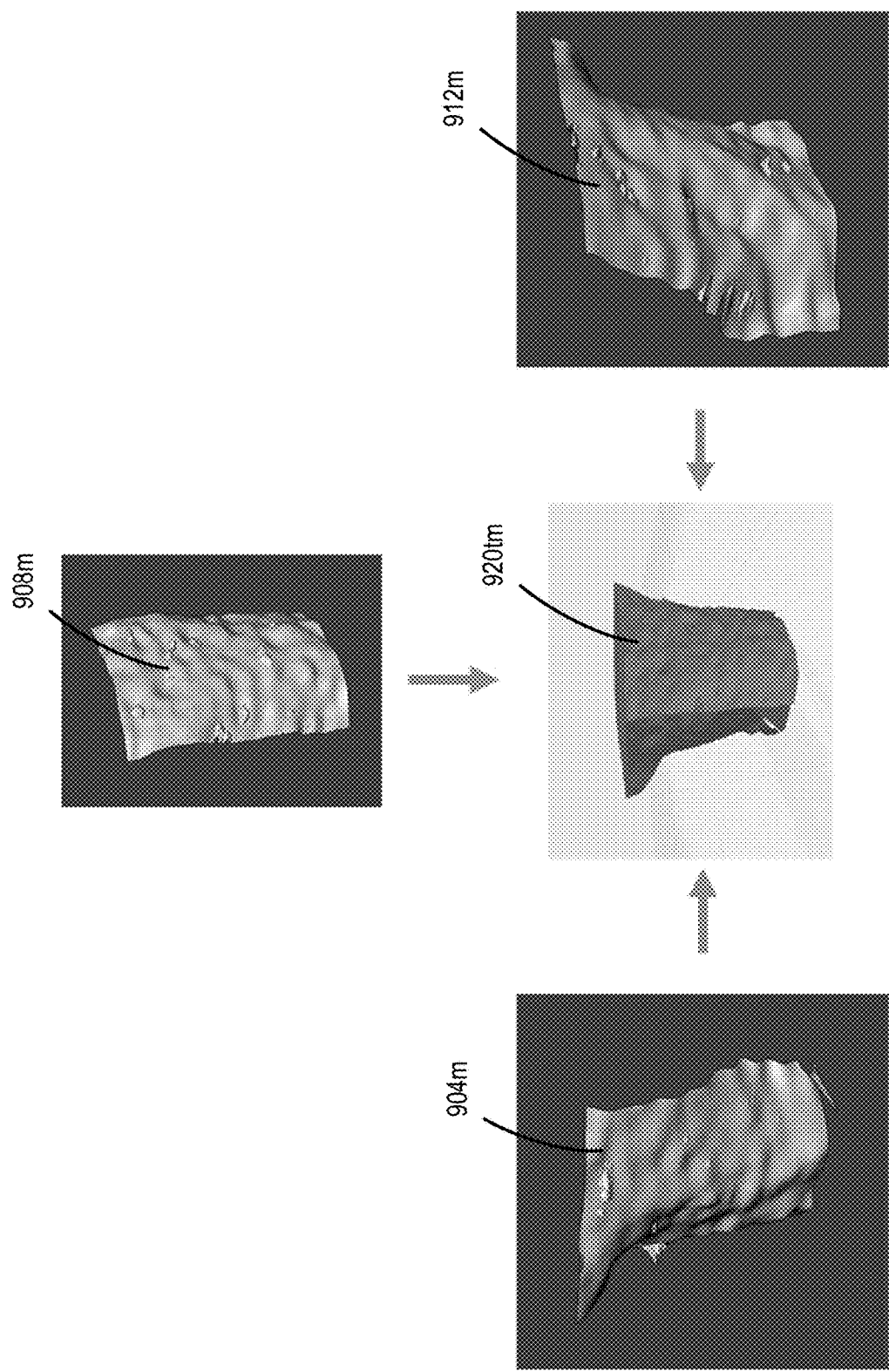
FIG. 19 shows examples of chest meshes and a 3-D torso model that may be generated using the setup of FIG. 18.

At step 608, a unified depth map is created (an example of which is shown in FIG. 19 and a method for creating the depth map is discussed with respect to FIG. 18). The unified depth map is generated such that it ignores inanimate stationary objects in the scene (e.g., furniture).

At step 610, a unified body shape model is created. This is to unify the depth coordinates from each of the depth cameras that are used into one coordinate system. This step is composed of two sub-steps. The first sub-step is to create an (x, y, z) coordinate dataset that belongs to the 3D surface of the subject/patient. The second sub-step is to map surface data to a human body model. For example, the relative positions of each of the depth cameras is known. The depth maps from each camera are then transformed into a common frame of reference. The meshes of the subject/patient that intersect are combined into a single volume. The localization of skeletal landmarks is a realization of mapping the 3D surface data from the subject/patient's body to a human body model, ending in localization of specific (tagged) landmarks such as, but not limited to, eyes, shoulders, hips, and the like as well as combinations thereof.

At step 612, multiple ROI detection is performed. This may be done by combining several methods such as, but not limited to, classical computer vision algorithms for face (such as Viola Jones, e.g.) and body segmentation, localization of skeletal landmarks, and adjusting the size and location of the various ROIs based on movement as was described for FIGS. 10A-10B. ROI may also be adjusted using triangulation. The ROIs may include, but are not limited to, areas around the cheeks, forehead, chest, abdomen, back, back of the head or combinations thereof). Once the landmarks are localized, the skeleton can then be tracked using an appropriate technique such as the Cubemos SDK as described previously. It should be noted that machine learning can also be used to get segmentation of body parts and localization of skeletal landmarks (e.g., see cv-foundation.org/openaccess/content_iccv_2015_workshops/w12/papers/Chandra_Accurate_Human-Limb_Segmentation_ICCV_2015_paper.pdf, which is incorporated herein by reference in its entirety).

At step 614, waveform generation is performed for each ROI and this may be done using the intensity and/or depth image data for each FoV. The waveform may be generated as was discussed for method 200 or method 400.

At steps 616, the skeleton of the patient/subject is tracked as explained previously. The skeletal tracking provides information on the movement of the subject/patient's body landmarks that were identified above.

At steps 618 and 620, the intensity changes and depth velocity waveforms are determined as was described previously for FIGS. 8A-9E.

At step 622 it is determined whether there are large movements indicated in the recorded depth and/or intensity data by applying criteria which may be based on using threshold values for the velocity measurements of the raw depth waveforms and/or a large drop in the SNR of the raw intensity and/or depth waveforms for each FoV. Alternatively, or in addition thereto, this step may also include checking for unwanted postures that may be determined using skeletal tracking. Examples of unwanted postures include, but are not limited to, the subject/patient's arms crossed around their torso, the hands of the subject/patient covering the torso and/or when the subject/patient is not facing a given camera properly. The portion of the waveforms that include large movement are discarded in step 624 and the remaining waveforms maybe directly joined or joined via interpolation, as previously discussed.

At step 626, motion compensation may be performed for data that includes small movements and this compensation may include resizing and repositioning the ROI on the subject's body based on its location and orientation in space as elucidated from skeletal tracking (as was explained previously for FIGS. 10A-10B). It can also include intensity renormalization based on depth (since intensity from a small light source is proportional to the distance$^2$ from the light source).

After step 626, the motion compensated or motion corrected intensity and/or depth data are used to estimate the RR for the n FoVs using low-frequency bandpass filtering at step 628 and peak detection at step 632 (the filtering and peak detection was explained previously for other methods). In an alternative embodiment, step 630 may be performed to fit a point cloud of the subject/patient onto a body shape model (e.g., a 3D model of the body and more specifically the torso area for RR), calculate the enclosed volume within this space and generate a time series that tracks body volume with time. The result is a waveform of Volume vs. time; follow with the peak detection algorithm as shown in FIG. 7. Step 634 then uses the output of steps 630 and 632 to estimate the RR for the n FoVs.

In a similar fashion for HR, after step 626 the motion compensated or motion corrected intensity and/or depth data are used to estimate the HR for the n FoVs using high-frequency bandpass filtering at step 634 and peak detection at step 636 (the filtering and peak detection was explained previously for other methods). Step 638 then uses the output of step 636 to estimate the HR for the n FoVs.

Motion Robustness from the Depth Channel (Single FoV)

Figure 12:
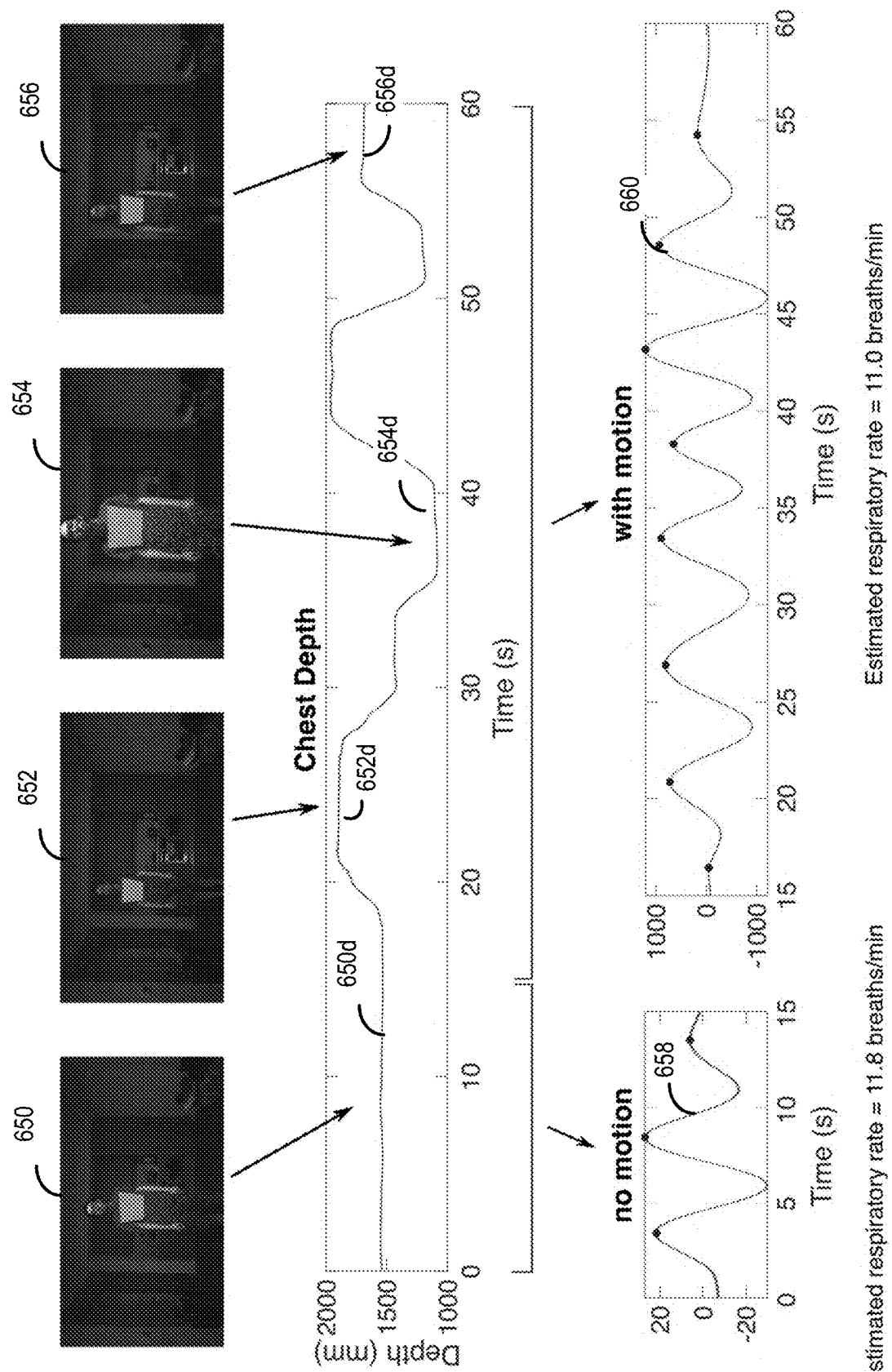
FIG. 12 shows an example of how simple non-periodic movement of a test subject can be compensated for by using skeletal tracking when preforming remote physiological signal measurement.

An example of motion compensation using a single-FoV camera arrangement is now discussed with reference to FIG. 12. In this example, simple non-periodic movement of a test subject/patient can be compensated for by using skeletal tracking when preforming remote physiological signal measurement. This allows for the creation of a dynamic chest ROI that moves along with the subject/patient movement.

The output of the skeletal tracking algorithm is used to generate ROIs, examples of which are shown in images 650 to 656. The trapezoidal perimeter for the ROIs may be determined based on labeled points on the body of the subject/patient, which may be generated using the Cubemos SDK.

Time series waveform generation then involves determining the arithmetic mean of all of the pixels in each ROI taken for all video frames (images) over the course of a given time period such as, but not limited to, 1 minute, for example. The region 650*d*, 652*d*, 654*d* and 656*d* of the spatially averaged chest depth waveform correspond to the ROIs 650, 652, 654 and 656, respectively.

Segments of the chest depth waveform where there is motion can then be removed using the technique described in step 624 of method 600 in FIG. 11, and a waveform 658 can be generated where segments with motion have been compensated. The estimated RR is 11.8 BrPM using the waveform 658. This is in contrast to the estimated RR of 11 BrPM for waveform 660 which has not been motion compensated. According, in this case analysis shows that the estimated RR for the waveform section without motion (0-15 seconds) and the waveform section with simple motion (15-60 seconds) are similar. The conclusion is that skeletal tracking allows for estimation of RR during subject motion that is close the estimated RR when there is no subject motion. What can be learnt is that sometimes the motion is not significant and therefore the correction does not seem to improve the RR a lot, in comparison to the no-motion case. It may also be the case that the motion can be filtered out using the Lo-Freq band pass filter.

Accordingly, this example shows that simple subject/patient movement can be compensated through the use of skeletal tracking. This allows continuous acquisition of respiratory data. However, this is not a universal solution, as shown in the case of FIG. 13.

Figure 13:
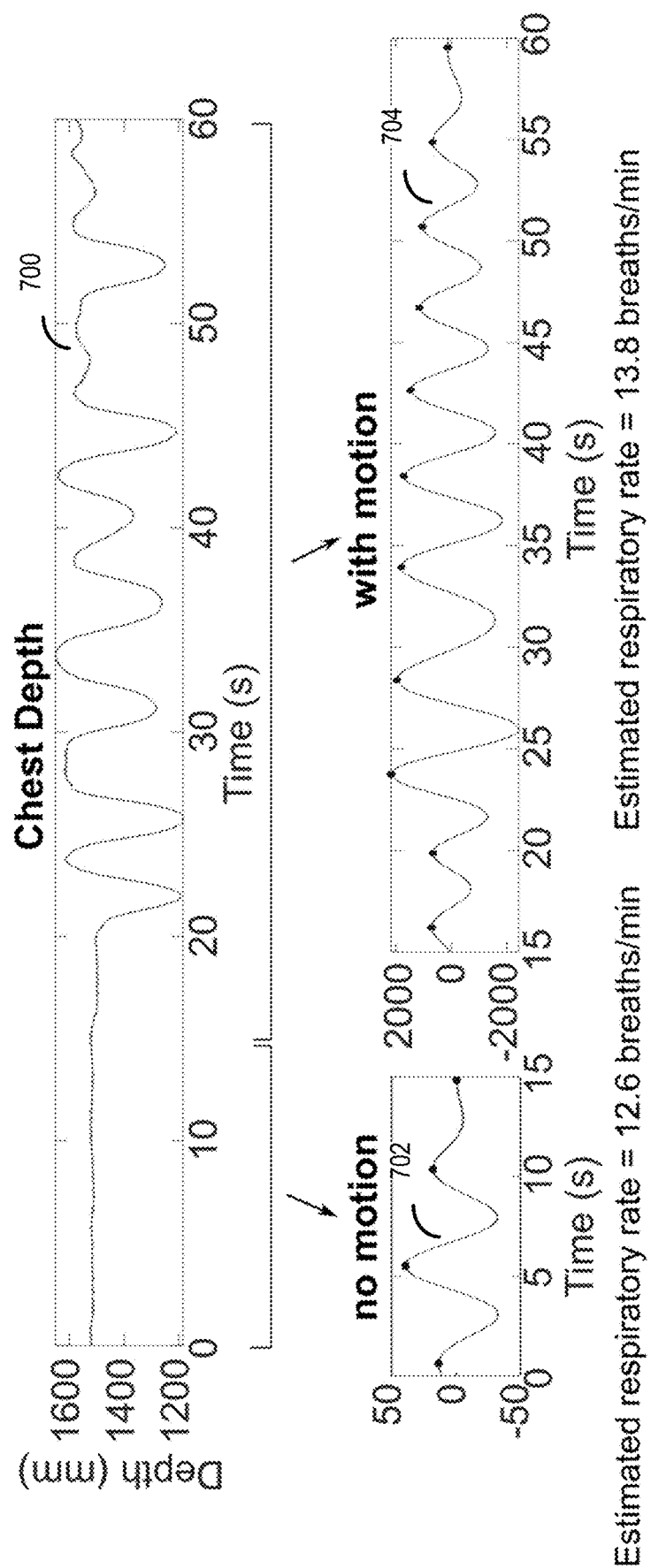
FIG. 13 shows an example of how periodic movement of a test subject results in an estimated RR that deviates significantly more from the true breathing rate.

Referring now to FIG. 13, shown therein is an example of how periodic movement of a test subject/patient in the chest depth waveform 700 results in an estimated RR from waveform 704 that deviates significantly more from the true breathing rate that may be obtained from waveform 702. For example, the estimated RR is about 13.8 BrPM for the waveform 704 with motion compared to an estimated RR of about 12.6 BrPM for the waveform 702 without motion. This is due to the algorithm's inability to differentiate the periodic chest movements from the overwhelming periodic motion when skeletal tracking is used. This is one of the drawbacks of using a single-FoV camera arrangement in this situation. However, a multi-FoV camera arrangement is capable of addressing this situation by using image data from one of the FoVs as a reference to separate gross body motion from respiratory-related motion. This is discussed below in the section "Motion robustness from the Depth Channel".

Referring now to FIGS. 26A-26D, which show another example of motion compensation using depth data obtained from multiple ROIs.

Figure 26A:
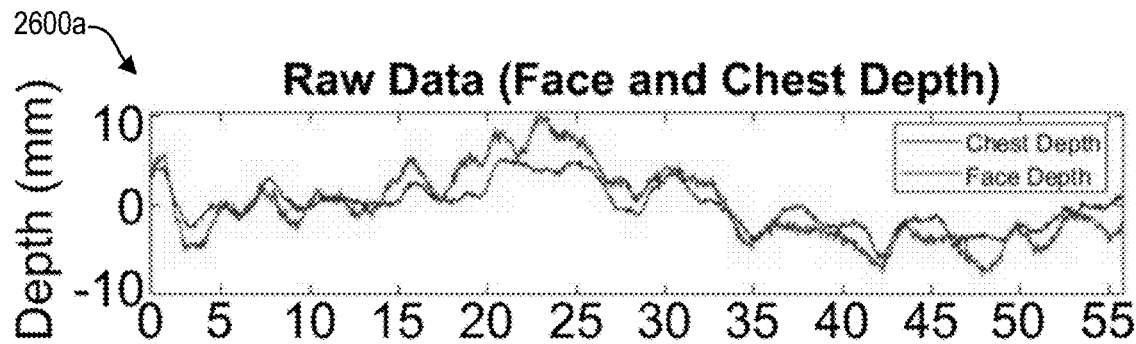
FIG. 26A shows overlayed raw waveforms of depth data obtained from ROIs located on both the chest and face of a test subject while the subject exhibits a swaying movement.
Figure 26B:
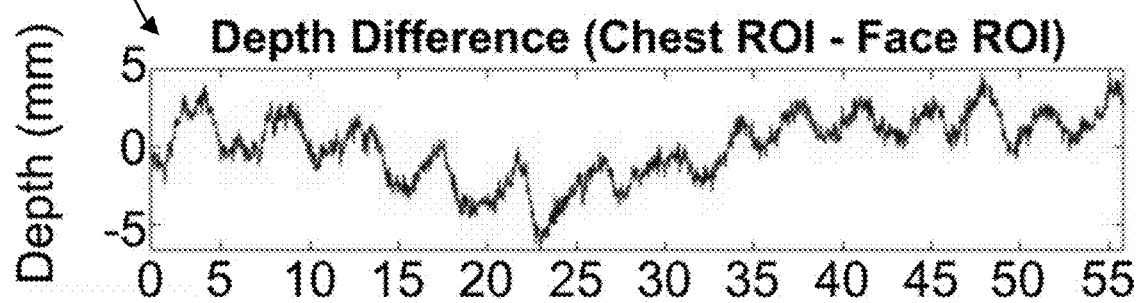
FIG. 26B shows a waveform comprising the difference between the raw depth waveforms in FIG. 26A obtained from the chest and face ROI.
Figure 26C:
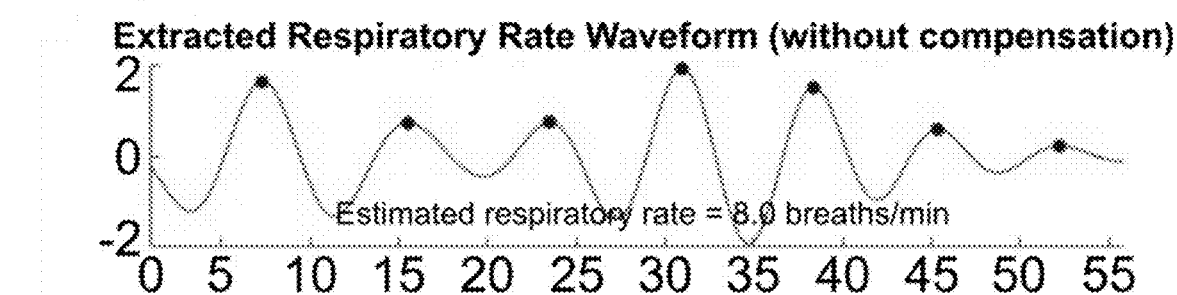
FIG. 26C shows an RR waveform extracted from the chest depth waveform in FIG. 26A, without compensation for the swaying motion.
Figure 26D:
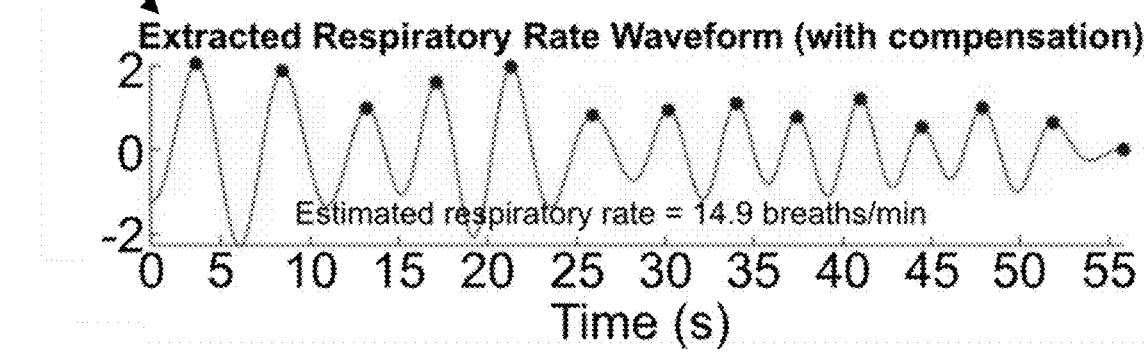
FIG. 26D shows an RR waveform extracted from the chest depth waveform in FIG. 26A, with compensation for the swaying motion based on the waveform in FIG. 26B.

FIG. 26A shows an example overlap of raw waveforms 2600*a* of depth data obtained from both a test subject's face and chest ROI. In this case, the subject is exhibiting swaying movement when instructed to stand stationary. The waveforms in FIG. 26A include: (a) a raw depth waveform obtained from the subject's chest ROI which contains respiratory information in addition to corrupting swaying motion, and (b) a raw depth waveform obtained from the test subject's face ROI which only contains the swaying motion. In this case, to compensate for the swaying movement and to reduce the corrupting effect of the swaying movement on the chest depth waveform, the depth difference is calculated between the depth data for the chest ROI and the depth data for the face ROI (i.e., chest ROI—face ROI) so as to isolate only the respiratory motion (see waveform 2600b in FIG. 26B). The respiratory waveform (2600b of FIG. 26B) may then be analyzed in accordance with any of the methods disclosed herein to extract the RR waveform. To this end, FIG. 26C shows the extracted RR waveform 2600c without motion compensation, while FIG. 26D shows the extracted RR waveform 2600d with motion compensation based on the calculated waveform 2600b in FIG. 26B. In the waveform 2600c of FIG. 26C (no motion compensation), the estimated RR is 8.0 BrPM, while in the waveform 2600d of FIG. 26D (with motion compensation) the estimated RR is 14.9 BrPM. The waveform of FIG. 26D with motion compensation is therefore closer (i.e., more accurate) with respect to the reference RR of 14.5 BrPM. Accordingly, FIGS. 26A-26D illustrate achieving swaying correction using only a single camera and multiple ROIs.

In at least one embodiment, it may be possible to dynamically switch between a single FoV and multi-FoV arrangement if the implementation physically allows for this. Since the skeletal tracking is dynamic, providing tracking for each video frame, the skeletal tracking may be analyzed to determine when there is simple non-periodic movement of the test subject/patient in which case the image data from a single-FoV arrangement can be used to estimate physiological signal values. Later, when the skeletal tracking indicates that there is periodic movement of the test subject/patient, the image data from a multi-FoV arrangement can be used to estimate physiological signal values.

Multi-FoV may have other benefits such as allowing for multiple estimates of RR and HR to be made and then combining the estimates using a different weight, to increase reliability due to this redundancy. This is useful since sometimes a body part may be covered.

Single FoV Derived Vital Sign Measurements—Some Takeaways

As described herein using a single FoV camera arrangement provides several benefits including:
- the ability to measure HR with both depth and intensity channels, by looking at multiple ROIs (e.g., forehead, cheeks, chest, etc.) of a subject/patient;
- the ability to measure RR with both depth and intensity/video channels, by looking at multiple ROIs (e.g., forehead, chest, shoulders, etc.) of a subject/patient;
- has been seen to be accurate to within 2% mean squared error (MSE) with respect to clinical gold standard, in a typical evaluation;
- can be used with motion compensation/motion rejection using the depth camera to sense instantaneous chest velocity where motion compensation of depth/intensity waveforms allows for the preservation of physiological information; and motion rejection provides removal of data from depth/intensity waveforms to gain improvements in accuracy of RR and HR estimates; and
- allows for a High-Redundancy Vital Signs Acquisition System in which both HR and RR can be measured in both depth and intensity channels, and by monitoring multiple ROIs which allows for switching over from one estimate method to another when certain ROIs or channels are not available, or to use estimates from multiple channels with weighted averaging and/or an outlier data rejection to increase the system accuracy in estimating the HR and RR values.

Figure 14:
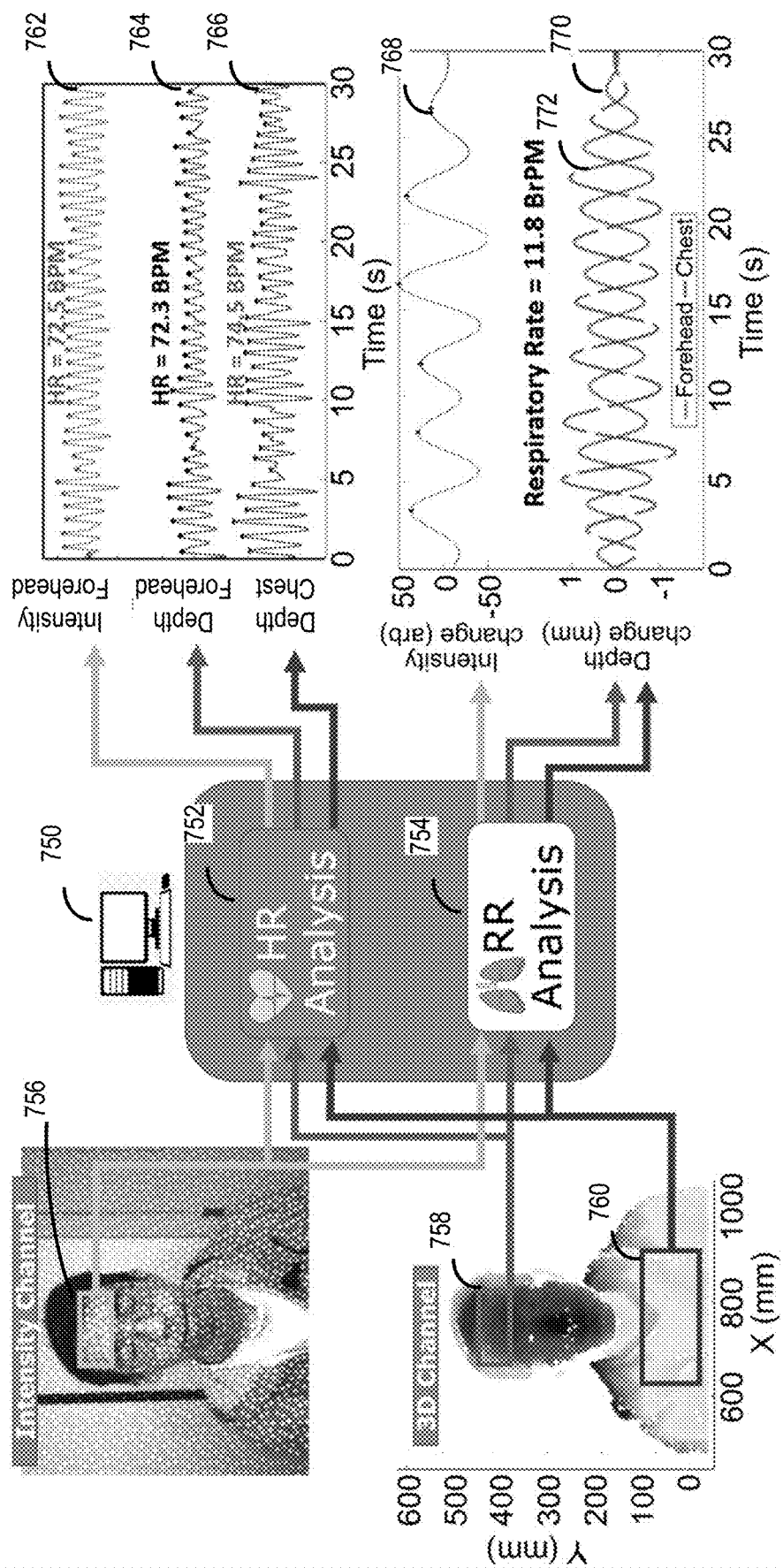
FIG. 14 shows a schematic of how a Multi-Channel High-Redundancy Vital Signs Acquisition System can be used to measure HR and RR in both depth and intensity channels, by using multiple ROIs.
Figure 15A:
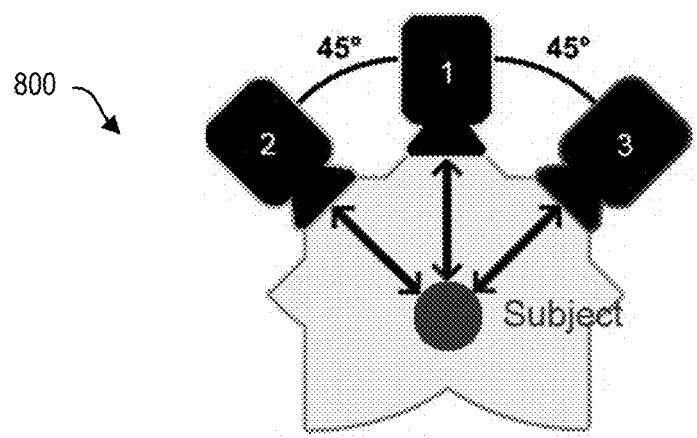
FIGS. 15A-15C show examples of different embodiments for a multi-FoV camera setup arrangement.
Figure 15B:
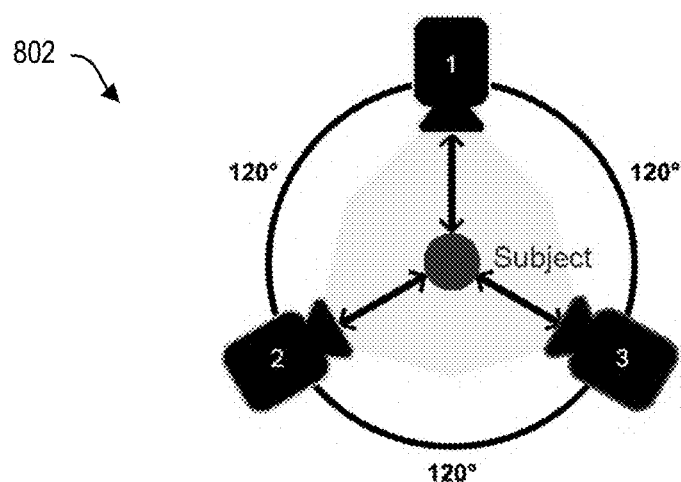
Figure 15C:
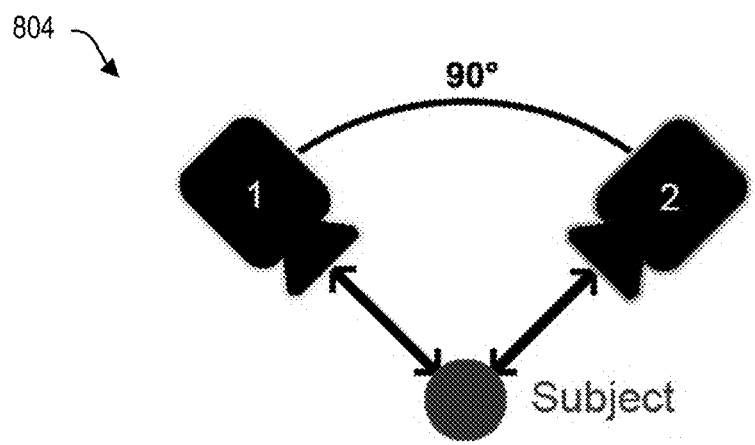

Referring now to FIG. 14, shown therein is a schematic of how a Multi-Channel High-Redundancy Vital Signs Acquisition System 750 can be used to measure HR and RR in both depth and intensity channels, by using multiple ROIs. In this example, a forehead ROI 756 for the intensity channel while a forehead ROI 758 and an upper chest ROI 760 is defined for the depth channel. HR waveforms 762, 764 and 766 may then be obtained using the appropriate methods described herein on the spatial waveforms for each of the ROIs 756, 758 and 760, respectively, in order to obtain three estimated HR values (in this example being 72.5 BPM, 72.3 BPM and 74.5 BPM). The estimated HR values can then be averaged or the median taken to provide a final estimated HR value. Likewise, estimates of respiratory waveforms 768, 770 and 772 may then be obtained using the appropriate methods described herein on the spatial waveforms for each of the ROIs 756, 758 and 760, respectively in order to obtain three estimated RR values which may then be combined using averaging or taking the median value to provide a final estimated RR value which in this example is 11.8 BrPM.

Multi-FoV Camera Arrangement

Multiple Field-of-View (multi-FoV) imaging provides information about the scene from various viewpoints. A multi-FoV camera arrangement may be implemented in a variety of ways with each of the camera pairs (i.e. intensity and depth cameras that are collocated) are positioned at different angles around the subject. For example, in FIG. 15A, the three camera pairs (1, 2, 3) are all on the same side of the subject where the outer camera pair are each angled 45 degrees with respect to the center camera pair. As another example, in FIG. 15B, the camera pairs (1, 2, 3) are on a circle around the subject and are 120 degrees apart from one another. As another example, in FIG. 15C, two camera pairs (1,2) are located on the same side of the subject and are angled a certain number of degrees apart, such as 90 degrees in this example. It is possible for there to be other multi-FoV camera arrangements. Also, while the multi-FoV camera arrangements have been described for camera pairs, the setup may only use a single depth camera at each location or a single intensity camera at each location.

The camera pairs are all set at the same height. Most times, the camera's FoV is much larger than the body of the subject/patient (e.g., see images in FIG. 18), so a moderate difference in camera height still allows to mark an ROI that represents the same region of the body from the images (intensity and depth) of the different camera pairs. The camera pairs are also synchronously triggered at a certain FPS rate such as 30 FPS.

When a pair of cameras (intensity and depth) are co-located and share the same FoV, complexity is reduced in setting up the multi-FoV camera arrangement as the vital signs estimates from both depth and intensity channels can then be compared on equal footing. When the FoV is different, it may be possible to obtain the estimated HR and RR values from each camera independently, and then assign a weight to each camera in combining the results.

The multi-FoV camera arrangement can provide multiple data channels (i.e. intensity and depth signals/maps) that can improve vital signs recording accuracy and increased motion tolerance. The use of multiple camera pairs increases the likelihood that the subject/patient is visible to at least one camera pair when other the viewpoints of other camera pairs may be obscured or have limited view of the body of the subject/patient. The multi-FoV camera arrangements may be used for remote vital signs monitoring in a home environment where multiple cameras can be placed in a room.

In the Multi-FoV camera arrangements, scene illumination can be provided in several ways, including: 1) room lights; 2) illumination sources co-located with a camera (the regions around the subject in FIGS. 15A and 15B) where the co-located light sources can be LEDs, lamps, or laser diodes with high brightness and efficiency and wavelengths that are selected to provide light that minimally disturbs the subject/patient and allows recording vital signs in a dark room; or 3) internal camera light source (i.e. no external illumination source, see FIG. 15C) such as laser diodes that are typically embedded within the 3D depth sensor and used to generate a depth map, and in many instances provide enough illumination to capture intensity waveforms.

Providing camera-mounted lighting, while recording vital signs, allows for the accurate measurement of vital signs that are stable under varying room light conditions.

Figure 16A:
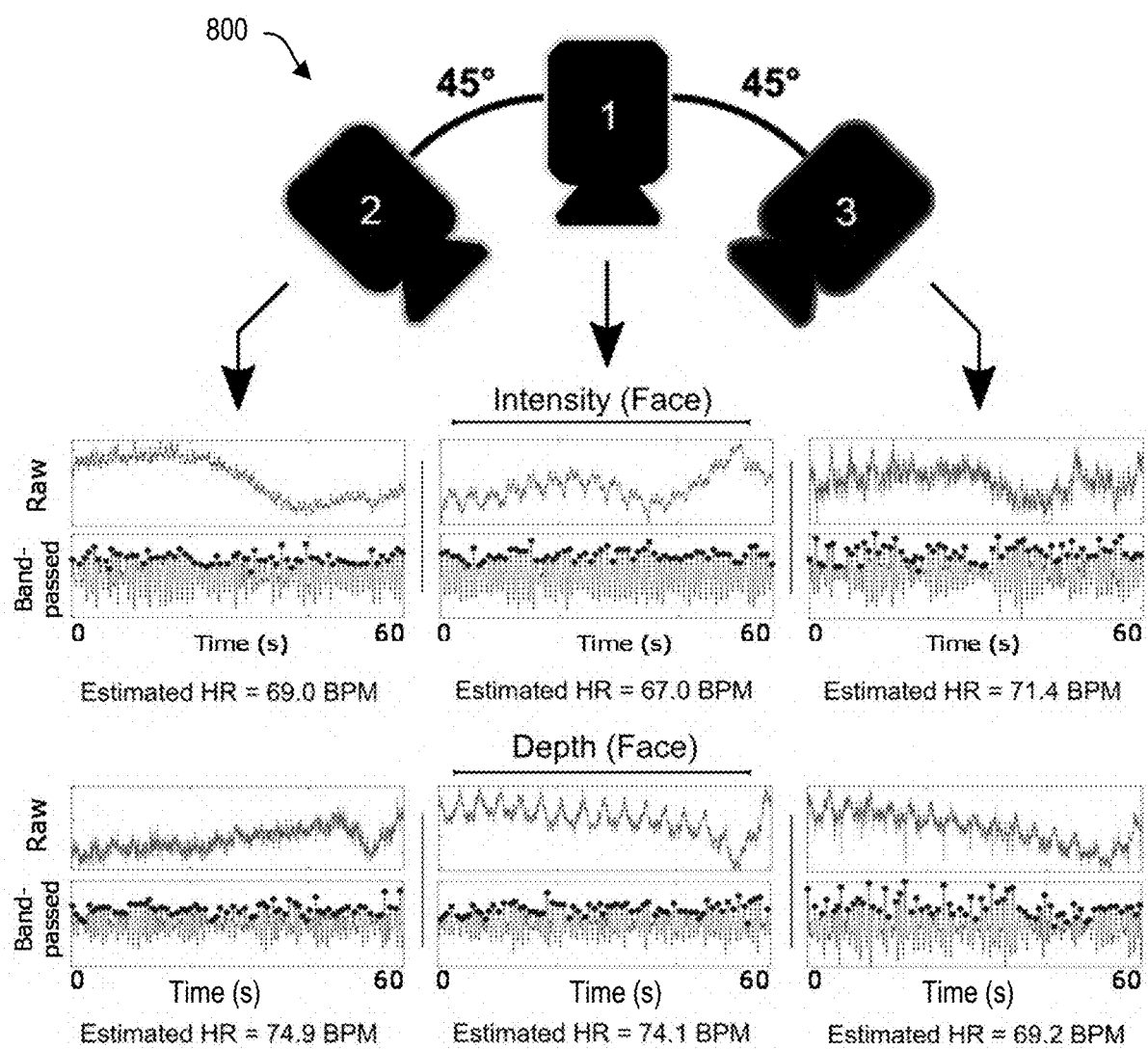
FIGS. 16A and 16B show HR and RR measurements, respectively, that were obtained with a multi-FoV setup.
Figure 16B:
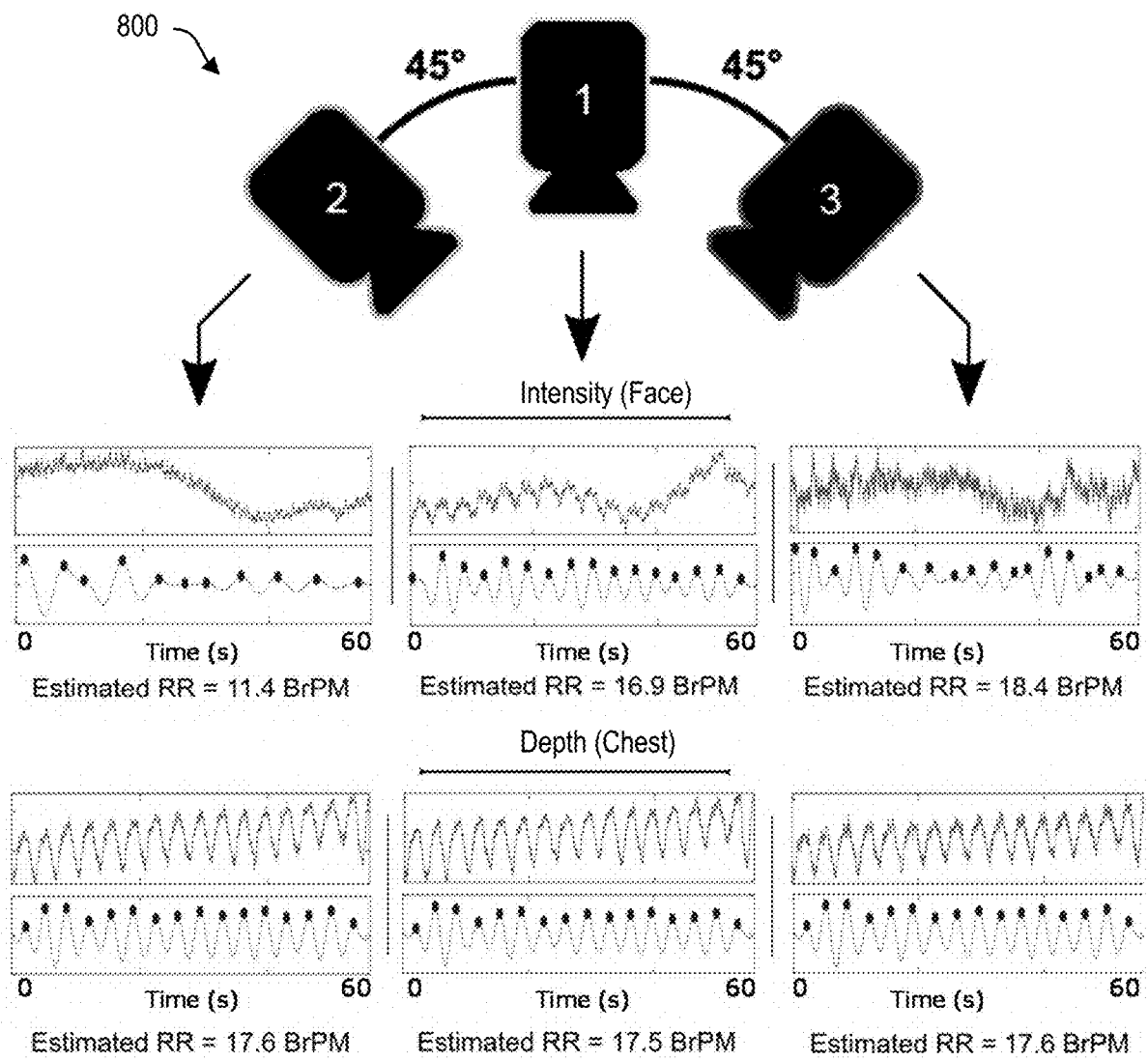

Referring now to FIGS. 16A and 16B, shown therein are HR and RR measurements, respectively, that were obtained with a multi-FoV setup. For example, using the multi-FoV setups shown in FIGS. 16A and 16B, the RR and HR were extracted from each FoV from both intensity and depth channels, providing a total of 6 data channels each for HR and RR estimates. The HR estimates were 69, 67, 71.4, 74.9, 74.1 and 69.2 BPM. The RR estimates were 11.4, 16.9, 18.4, 17.6, 17.5 and 17.6 BrPM. The discrepancies in the estimated values of both the RR and HR depend on the FoV and data channel used. This is attributed to the slight uncompensated movements of the subject/patient and uneven illumination of the scene. However, the estimated values are all within 10% of each other (except for one of the RR estimate at 11.4 BrPM). Using a weighted average algorithm, or another statistical method, values for the RR and HR can be estimated that more closely approach the true values.

Motion Robustness from the Depth Channel (Multi-Field of View)

Multiple cameras allow recording of multiple depth changes due to the subject/patient motion and to improve motion robustness. An example to motion compensation using multi-FoV is presented with respect to FIGS. 17A-170, FIGS. 17D-17G and FIGS. 27A-27D.

FIG. 17A shows a test setup 850a for a demonstration of motion tolerance using two cameras 852 and 854 in a front and back configuration on either side of a standing test subject 856 where the torso of the test subject 856 is used as an ROI. In this example, the two cameras 852 and 854 were spaced by a distance of 2 meters. The common motion of the subject 856 as the subject exhibits limited movement (i.e., swaying movement while standing) between the cameras 852 and 854 is observed by subtracting from one another the waveforms 858 and 860 (see FIG. 17B) that were derived from the two different cameras 852 and 854, which are diametrically opposed. The subtracted waveform is the respiratory waveform 862 (see FIG. 17C) from which the RR of the subject 856 may be estimated. In this example the estimated RR is 15 BrPM. The tolerance to motion provided by this setup 850a is in the axis defined by the two cameras. The three FoV camera approach described for FIG. 18 extends this tolerance to any sort of 2-D motion within the area defined by the intersection of the FoVs of the three cameras.

Figure 17E:
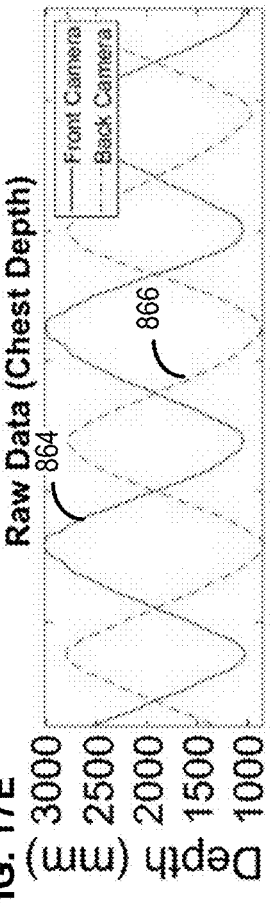
FIG. 17E shows depth data that is acquired from each camera in the setup of FIG. 17D while the subject exhibits greater motion range (i.e., the subject is walking back and forth).
Figure 17F:
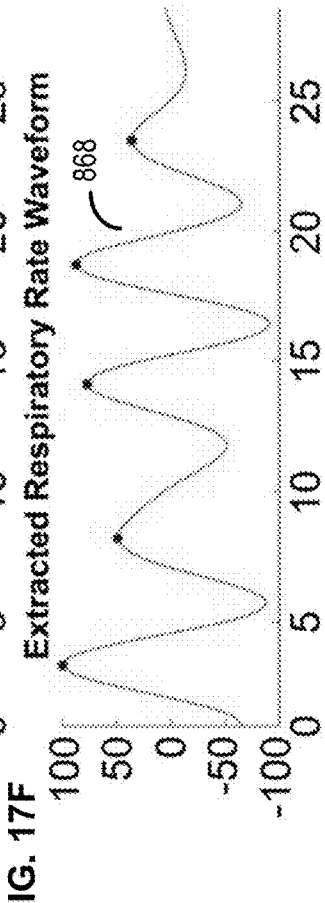
FIG. 17F shows a respiratory waveform that is isolated from the two depth signals in FIG. 17E to derive RR.
Figure 17G:
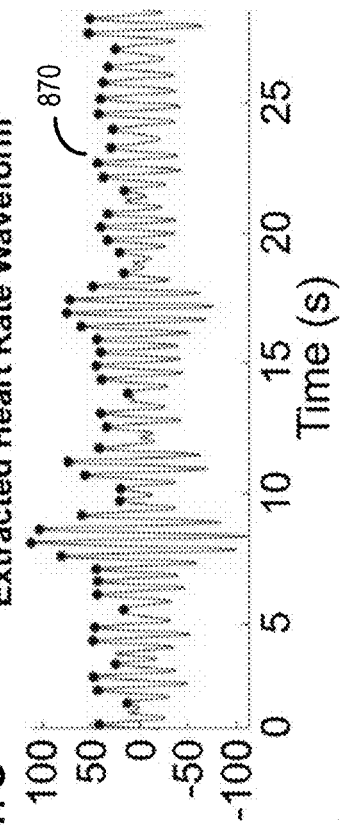
FIG. 17G shows an HR waveform that is isolated from the two depth signals in FIG. 17E.
Figure 17D:
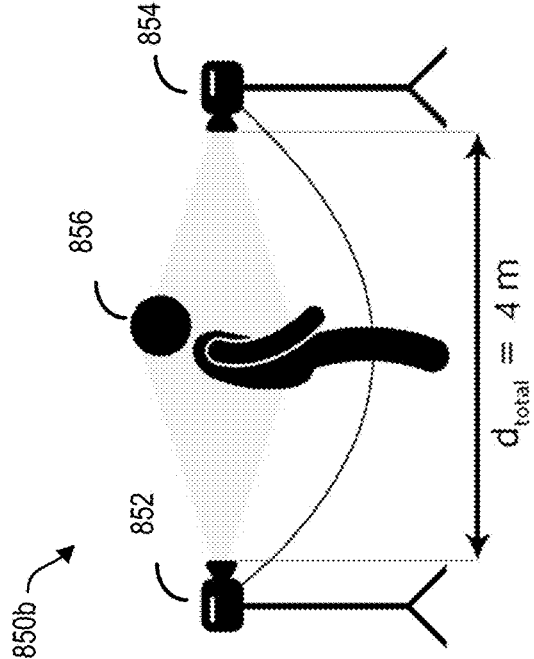
FIG. 17D shows a demonstration of motion tolerance using two cameras in a front and back configuration on either side of a standing test subject where the test subject's torso is used as an ROI, in accordance with another example embodiment.

FIG. 17D shows another test setup 850b, which also demonstrates motion tolerance using two cameras 852 and 854 in a front and back configuration on either side of a standing test subject 856 where the chest of the test subject 856 is used as an ROI. In this example, the two cameras 852 and 854 are now spaced by a distance of 4 meters. In this case, as the subject has the ability to walk back and forth between the cameras, the common motion of the subject 856 as the subject walks back and forth between the cameras 852 and 854 are again observed by subtracting from one another the waveforms 864 and 866 (see FIG. 17E) that were derived from the two different cameras 852 and 854, which are diametrically opposed. The subtracted waveform is the respiratory waveform 868 (see FIG. 17F) from which, in accordance with any of the methods described herein, the RR of the subject 856 may be estimated, as well as the HR waveform 870 (see FIG. 17G) from which the HR of the subject 856 may be estimated. In this example the estimated RR is 11.9 BrPM and the reference RR was 11.8 BrPM, while the estimated HR is 104.8 bpm and the reference HR is 105.4 bpm.

Accordingly, the use of two opposing cameras with a known reference distance demonstrates the applicability of a gradiometric approach to motion compensation and separation of several vital signs such as HR and RR for a moving subject. In particular, in subtracting the global body motion (i.e. source separation), the respiratory-related and pulse-related periodic depth changes may be revealed. The multiple camera FoVs, providing independent depth changes from different angles can therefore be expected to increase the accuracy in such motion compensation. Further, the various viewpoints can also be expected to increase the accuracy in determining the position, velocity and direction of the subject's motion and can be used for improving the localization of the various ROIs, used to record the vital signs waveforms.

Reference is also made to FIGS. 27A-27D, which show another example of motion compensation using depth data obtained from multiple camera FoVs.

Figure 27A:
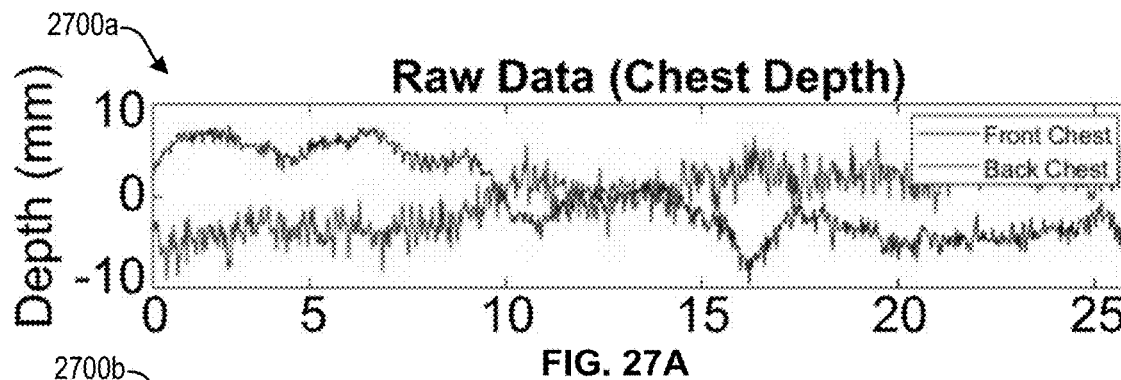
FIG. 27A shows overlayed raw waveforms of depth data obtained from a test subject's front and back chest ROI while the test subject exhibits a swaying movement.
Figure 27B:
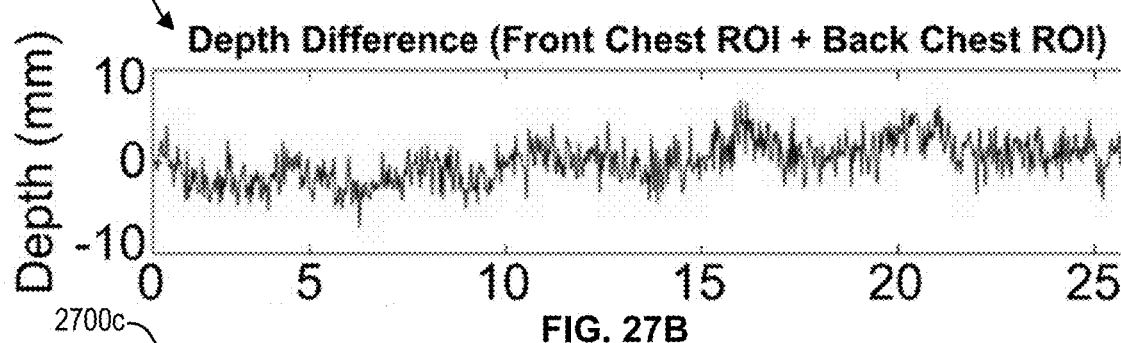
FIG. 27B shows a waveform comprising the difference between the raw front and rear chest depth waveforms in FIG. 27A.

FIG. 27A shows an example overlap of raw waveforms 2700a of depth data obtained from both a test subject's front and rear chest ROI using a front and rear camera that are setup about four (4) meters apart (i.e., FIG. 17D). In this example case, the subject is exhibiting swaying movement when instructed to stand stationary. The waveforms in FIG. 27A include: (a) a raw depth waveform obtained from the subject's front chest ROI, and (b) a raw depth waveform obtained from the test subject's rear chest ROI. To compensate for the swaying movement and to reduce the corrupting effect of the swaying movement on the chest depth waveform, the depth difference is calculated between the depth data for the front and rear chest ROI (i.e., front chest ROI+rear chest ROI) so as to isolate only the respiratory motion (see waveform 2700b in FIG. 27B).

It is noted that, in contrast to the waveforms in FIG. 26 which are recorded using a single camera, in the case of the waveforms in FIG. 27, two cameras are used. Accordingly, the depth difference is calculated as the addition (rather than subtraction) of the front and rear chest ROI because of the opposite locations of the cameras which are monitoring the front and rear chest ROI (i.e., as in FIG. 17D). Because the cameras are opposing each other, when a person is swaying towards the front camera, the measured depth value to the front camera is smaller, while the measured depth value to the rear camera is larger. Therefore, taking only the readout depth values, in order to determine the distension of the subject's chest and record the subject's RR, it would be necessary to calculate the average value of front chest ROI distance+back chest ROI distance. For opposing cameras, adding these two values corresponds to effectively removing the walking effect and maintaining only the breathing effect. To this end, in FIG. 27A, the depth values are absolute values, wherein the average distance from camera to the person is removed in order to center values at depth=0 mm, i.e., similar to FIG. 26A.

Figure 27C:
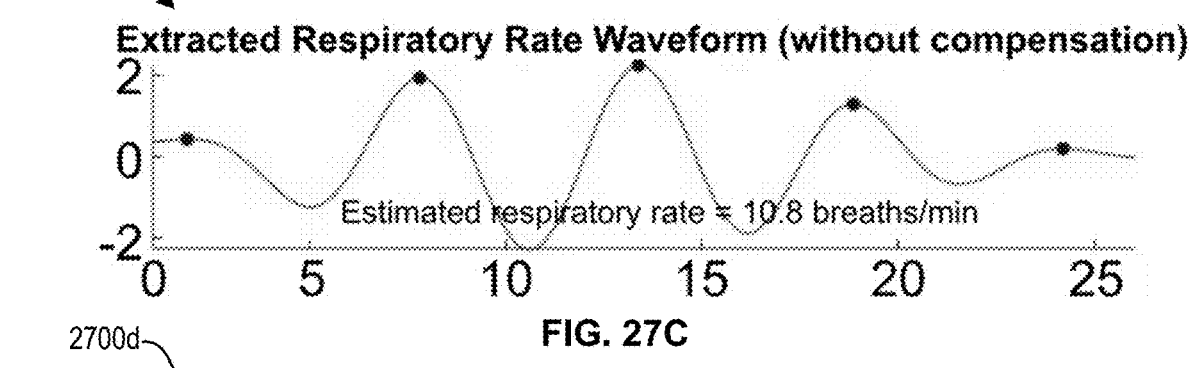
FIG. 27C shows an RR waveform extracted from the front chest depth waveform in FIG. 27A, without compensation for the swaying movement.
Figure 27D:
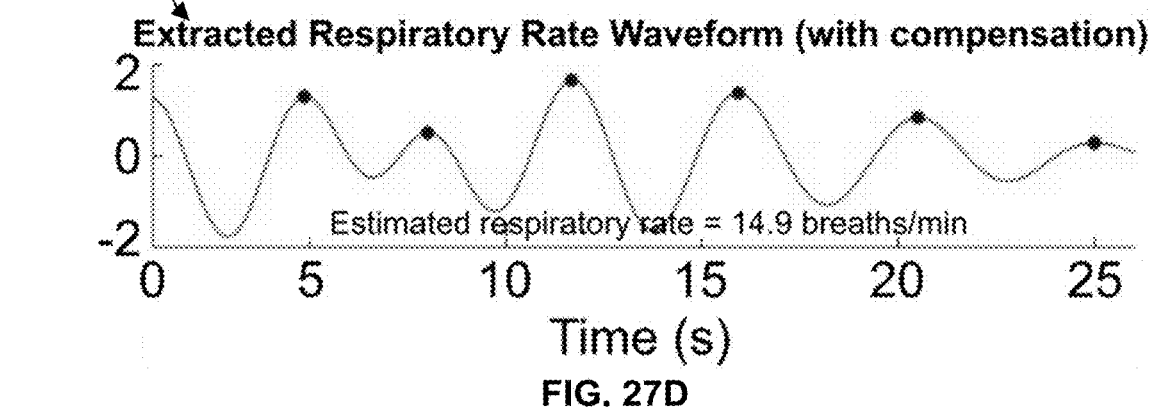
FIG. 27D shows an RR waveform extracted from the front chest depth waveform in FIG. 27A, with compensation for the swaying movement based on the waveform in FIG. 27B.

The respiratory waveform (2700b of FIG. 27B) may then be analyzed in accordance with any of the methods disclosed herein to extract the RR waveform. To this end, FIG. 27C shows the extracted RR waveform 2700c without motion compensation, while FIG. 27D shows the extracted RR waveform 2700d with motion compensation based on the calculated waveform 2700b in FIG. 27B. In the waveform 2700c of FIG. 27C (no motion compensation), the estimated RR is 10.8 BrPM, while in the waveform 2700d of FIG. 27D (with motion compensation) the estimated RR is 14.9 BrPM. The waveform of FIG. 27D with motion compensation is therefore closer (i.e., more accurate) with respect to the reference RR of 15.0 BrPM. Accordingly, FIGS. 27A-27D illustrate achieving swaying correction using a multi-camera approach to correct for subject swaying. In other embodiments, other front and rear ROI regions may be used for motion swaying compensation using multiple FoV cameras (i.e., a face ROI).

Referring now to FIG. 18, shown therein is another example of an experimental setup for performing motion compensation using a multi-FoV camera arrangement using three camera pairs as well as example scenes 902, 906 and 910 with ROIs 904, 908 and 912, respectively. The different locations labeled 1,2,3 each contain a pair of cameras (intensity and depth) sharing the same FoV. The marked ROIs 904, 908 and 912 are shown to represent the chest region as viewed from each of the three camera pairs, and selected automatically using the skeletal tracking as described previously.

Referring now to FIG. 19, shown therein are examples of chest meshes 904m, 908m and 912m and a 3-D torso model 920tm that may be generated using the setup of FIG. 18. This provides more detailed information on how the chest moves during respiration. For example, one can build a body model for the body surface and enclosed volume within it, and track how the body surface and the enclosed volume change over time. Respiration not only moves the chest wall, but also changes the lung volume and this can be used to track volume changes, as an alternative means to calculate respiration rate, and also indicate other physiological symptoms that are correlated with different breathing patterns.

Accordingly, in summary, various embodiments have been described for hardware and associated methods of extracting RR and HR waveforms from different ROIs for depth image data acquired using a depth camera and from the same or different ROIs for intensity image data acquired using an intensity camera as shown in FIG. 14.

In another aspect, after completing an independent estimates of HR and RR, a different weight can be provided to the estimated HR or RR values depending on the channel and the ROI (for example, HR values may be trusted more when obtained from an intensity channel and the ROI is the forehead, and RR values may be more trusted when obtained from a depth channel and the ROI is the chest area.

The HR and RR values can be estimated independent of external illumination since the various cameras may include their own illumination or an additional light source may be used. Accordingly, the vital signs measurements may be therefore done with or without an ambient light source such as room lights or outdoor light, and with or without the light unit 24 (see FIG. 1A).

In addition, the use of the dot pattern may be sufficient in many cases to provides a good depth map for a subject, and in some cases also a reasonable intensity map, just by the dot illumination. This may involve giving more weight to estimates using depth data from the depth channel in the redundancy scheme (e.g., of FIG. 14).

It should be noted that maps from several modalities can be fused for depth cameras to allow a multi-distance operation where for far away subjects (say 2-10 meters away from the device 10) a Time of flight camera may be used to obtain the depth data for the depth channel and as the device 10 gets closer to the subject, a stereo camera depth data channel can be used to obtain the depth data, which allows the features of motion correction and extraction of HR and RR across several distances.

It should also be noted that in at least one embodiment, the intensity camera may be a "combined" RGB and IR camera (RGB+IR). This provides the benefit of performing the intensity analysis shown in FIG. 4 on different spectral channels. Therefore, for different locations of the ROI, one may choose between the various spectral channels and it is sometimes easier to conduct facial and/or body tracking when you use the different spectral channels.

Prioritized Selection of Depth Versus Intensity Channels

Reference is now made to FIGS. 20 to 25, which further illustrate the above concepts and demonstrate how, in various cases, the HR and/or RR measurements may be determined using either the depth or intensity channels, depending on surrounding circumstances.

FIGS. 20 to 22B illustrate an example case where the depth data may be prioritized over the intensity data to determine a subject's HR and/or RR measurements. In this example case, the subject may be present in low light settings. For example, the subject may be present in a dimly lit room, or a room with no light (i.e., see FIG. 20) with the infrared projector of the camera providing the only illumination (or a separate depth sensor with an active illumination, such as a LiDAR or time of flight depth sensor). In this example case, owing to the lack of ambient light, there may be little to no intensity data to be gathered. Accordingly, to mitigate for these circumstances, the depth data may be prioritized to determine the subject's HR and/or RR. To this end, FIG. 21A shows example raw depth data 2100a acquired from a test subject's face ROI (2002 in FIG. 20) in low light settings, while FIG. 22A shows example obtained raw depth data from a subject's chest ROI (2004 in FIG. 20) also in low light settings. FIG. 21B shows an HR waveform 2100b that is extracted from the raw depth data 2100a in FIG. 21A in accordance with any of the methods provided herein, while FIG. 22B shows an RR waveform 2200b that is extracted from the raw depth data 2200a of FIG. 22A, also in accordance with any methods provided herein. Accordingly, in this example case, the depth data is generally sufficient to determine HR and/or RR measurements where, for example, the intensity data is generally not available.

Figure 25A:
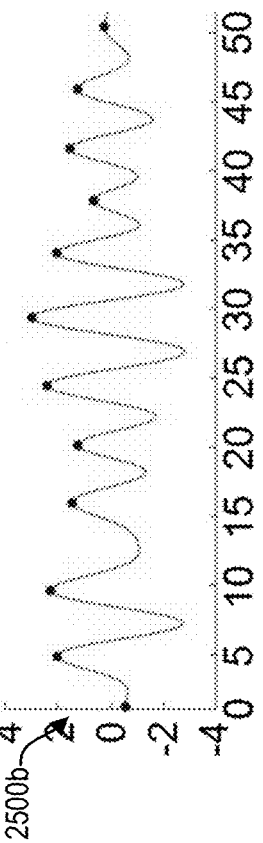
FIG. 25A shows an example of a raw waveform of depth data obtained from an ROI located on the chest of a test subject in a reclined position.
Figure 25B:
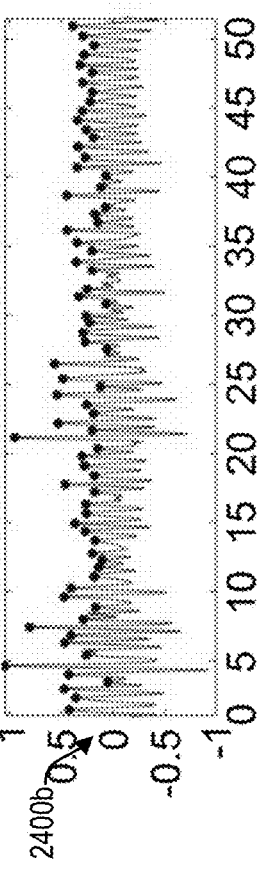
FIG. 25B shows an extracted RR waveform from the waveform of FIG. 25A.

FIGS. 23 to 25B illustrate an alternative example case where intensity data may be prioritized over depth data to determine a subject's HR and/or RR measurements. In this example case, the subject may be in a reclined position or otherwise lying down at a near-supine angle (see e.g., FIG. 23). For example, the subject may be lying on a hospital bed, or otherwise resting their head on the back of a chair. In this position, there may be no observable depth changes from ballistocardiographic forces around a chest ROI as a result of the position of the subject relative to the camera position. Accordingly, there may be no depth data available to generate RR and/or HR measurements, and therefore the intensity data may be primarily relied on to determine the subject's HR and/or RR. To this end, FIG. 24A shows example raw intensity data 2400a acquired from a face ROI of a subject in a reclined position, while FIG. 25A shows example raw depth data acquired from a subject's chest ROI while the subject is also in a reclined position. FIG. 24B shows an HR waveform 2400b that is extracted from the raw intensity data 2400a in FIG. 24A in accordance with any of the methods described herein. FIG. 25B shows an RR waveform 2500b that is extracted from the raw depth data 2500a of FIG. 25A, also in accordance with any of the methods described herein. Accordingly, these figures demonstrate an example case where intensity data is sufficient to determine HR and/or RR measurements where, for example, the depth data is generally not available or insufficient for use.

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

The invention claimed is:

1. A device for performing remote physiological signal monitoring on a subject, wherein the device comprises:
a first camera unit having a first pair of collocated cameras having a same field of view, the first pair of collocated cameras comprising a depth camera with a depth channel for providing depth data and an intensity camera with an intensity channel for providing intensity data obtained from capturing depth images and intensity images, respectively, of the subject;
a memory for storing program instructions for performing a method of remote physiological signal monitoring on the subject; and
a processor unit that includes at least one processor that is operably coupled to the first camera unit for receiving the depth data and the intensity data and operatively coupled to the memory for executing the program instructions for performing the method of physiological signal monitoring which configures the at least one processor to:
detect at least one region of interest (ROI) for images in the intensity data and/or the depth data;
generate waveforms for the intensity data and the depth data where a given data point in the waveforms is obtained using pixel values in the at least one ROI for the images in the intensity data and the depth data;
estimate at least one heart rate (HR) value for the subject by performing high frequency bandpass filtering on the waveforms of the intensity data and the depth data to obtain corresponding HR waveforms for the intensity data and the depth data; performing peak detection on the HR waveforms to determine a series of peaks and estimating the at least one HR value based on temporal spacing between the series of peaks in the HR rate waveforms; and
estimate at least one respiratory rate (RR) value for the subject by performing low frequency bandpass filtering on the waveforms of the intensity data and the depth data to obtain corresponding respiratory waveforms for the intensity data and the depth data; performing peak detection on the respiratory waveforms to determine a series of peaks and estimating the at least one RR value based on temporal spacing between the series of peaks in the respiratory waveforms.

2. The device of claim 1, wherein the at least one processor is further configured to analyze the waveforms for the intensity data and/or the depth data and is further configured to:
identify one or more segments of the waveform for the intensity data and/or the depth data which include subject motion;
determine if the motion in each of the identified segments is classifiable as a large motion; and
if the motion is classifiable as a large motion, perform motion rejection by discarding the respective identified segments of the intensity data and/or the depth data, otherwise applying motion compensation to the respective identified segments.

3. The device of claim 2, wherein the at least one processor is further configured to perform motion compensation on the waveform of the depth data by identifying segments in the waveform of the depth data that have an instantaneous velocity that is larger than a predefined velocity threshold and/or have a signal to noise ratio (SNR) that is lower than a first predefined SNR threshold and removing the identified segments from the waveform of the depth data before performing the high frequency bandpass filtering.

4. The device of claim 2, wherein the at least one processor is further configured to perform motion compensation on the waveform of the intensity data by identifying segments in the waveform of the intensity data that have an instantaneous intensity change rate that is larger than a predefined intensity change rate threshold and/or have a signal to noise ratio (SNR) that is lower than a second predefined SNR threshold and removing the identified segments from the waveform of the intensity data before performing the high frequency bandpass filtering.

5. The device of claim 2, wherein the at least one processor is further configured to use skeletal tracking to dynamically localize the at least one ROI for the images in the intensity data and/or the depth data, and optionally is further configured to change a size of the at least one ROI to reflect different skeletal postures of the subject determined from the skeletal tracking.

6. The device of claim 2, wherein the at least one processor is configured to use skeletal tracking to detect motion events for the subject for intensity and/or depth data, determine a severity of a motion during a detected motion event, apply motion compensation when the severity of the motion indicates small movements and apply motion rejection when the severity of the motion indicates large movements.

7. The device of claim 6, wherein the at least one processor is configured to perform motion compensation by: (a) resizing and/or repositioning the at least one ROI on a body of the subject based on a location and orientation of the at least one ROI in space as determined from the skeletal tracking; and/or (b) performing intensity renormalization based on the depth data.

8. The device of claim 1, wherein the at least one ROI comprises any combination of one or more cheek regions, a forehead region, an upper chest region, a lower chest region, an abdominal region, a back region, a back of the head and a whole face of the subject.

9. The device of claim 1, wherein the device comprises at least one additional pair of collocated cameras that have an additional field of view that is different than the field of view of the first pair of collocated cameras for obtaining a second set of intensity data and depth data and the at least one processor is configured to obtain additional estimates of HR and RR from the second set of intensity data and depth data.

10. The device of claim 9, wherein the at least one additional pair of collocated cameras is positioned opposite the first camera unit, wherein the second set of intensity data and depth data generated by the at least one additional pair of collocated cameras is used as a reference to subtract a subject's body movement as measured by a difference in distance between the first pair of collocated cameras and the at least one additional pair of collocated cameras and allow separation of the subject's body movement from vital signs related to depth changes and being optionally further used to obtain movement compensated estimates of HR and/or RR from the second set of intensity data and depth data.

11. A computer implemented method of performing remote physiological signal monitoring on a subject using at least one processor that is operatively coupled to a memory that stores program instructions for performing the method, wherein the method comprises:

positioning the subject within a field of view of a first camera unit having a first pair of collocated cameras having a same field of view, the first pair of collocated cameras comprising a depth camera with a depth channel for providing depth data and an intensity camera with an intensity channel for providing intensity data obtained from capturing depth images and intensity images, respectively, of the subject;

detecting at least one region of interest (ROI) for images in the intensity data and/or the depth data;

generating waveforms for the intensity data and the depth data where a given data point in the waveforms is obtained using pixel values in the at least one ROI for the images in the intensity data and the depth data;

estimating at least one heart rate (HR) value for the subject by performing high frequency bandpass filtering on the waveforms of the intensity data and the depth data to obtain corresponding HR waveforms for the intensity data and the depth data; performing peak detection on HR waveforms to determine a series of peaks and estimating the at least one HR value based on temporal spacing between the series of peaks in the HR waveforms; and estimating at least one respiratory rate (RR) value for the subject by performing low frequency bandpass filtering on the waveforms of the intensity data and the depth data to obtain corresponding respiratory waveforms for the intensity data and the depth data; performing peak detection on the respiratory waveforms to determine a series of peaks and estimating the at least one RR value based on temporal spacing between the series of peaks in the respiratory waveforms.

12. The method of claim 11, further comprising:
identifying one or more segments of the waveform for the intensity data and/or the depth data which include subject motion;
determining if the motion in each of the identified segments is classifiable as a large motion; and
if the motion is classifiable as a large motion, performing motion rejection by discarding the respective segments of the intensity data and/or the depth data, otherwise applying motion compensation to the respective identified segments.

13. The method of claim 12, wherein the method further comprises performing motion compensation on the waveform of the depth data by identifying segments in the waveform of the depth data that have an instantaneous velocity that is larger than a predefined velocity threshold and/or have a signal to noise ratio (SNR) that is lower than a first predefined SNR threshold and removing the identified segments from the waveform of the depth data before performing the high frequency bandpass filtering.

14. The method of claim 12, wherein the method further comprises performing motion compensation on the waveform of the intensity data by identifying segments in the waveform of the intensity data that have an instantaneous intensity change rate that is larger than a predefined intensity change rate threshold and/or have a signal to noise ratio (SNR) that is lower than a second predefined SNR threshold and removing the identified segments from the waveform of the intensity data before performing the high frequency bandpass filtering.

15. The method of claim 12, wherein the method comprises using skeletal tracking to dynamically localize the at least one ROI for the images in the intensity data and/or the depth data, and optionally further comprises changing a size of the at least one ROI to reflect different skeletal postures of the subject determined from the skeletal tracking.

16. The method of claim 12, wherein the method further comprises using skeletal tracking to detect motion events for the subject for intensity and/or depth data, determining a severity of a motion during a detected motion event, apply motion compensation when the severity of the motion indicates small movements and applying motion rejection when the severity of the motion indicates large movements.

17. The method of claim 16, wherein the method further comprises performing motion compensation by: (a) resizing and/or repositioning the at least one ROI on a body of the subject based on a location and orientation of the at least one ROI in space as determined from the skeletal tracking; and/or (b) performing intensity renormalization based on the depth data.

18. The method of claim 11, wherein the method comprises defining the at least one ROI to include any combination of one or more cheek regions, a forehead region, an upper chest region, a lower chest region, an abdominal region, a back region, a back of the head and a whole face of the subject.

19. The method of claim 11, wherein the method further comprises using at least one additional pair of collocated cameras that has an additional field of view that is different than the field of the view of the first pair of collocated cameras for obtaining a second set of intensity data and depth data and the obtaining additional estimates of HR and RR from the second set of intensity data and depth data.

20. The method of claim 19, wherein the at least one additional pair of collocated cameras is positioned opposite the first camera unit, wherein the second set of intensity data and depth data generated by the at least one additional pair of collocated cameras is used as a reference to subtract a subject's body movement as measured by a difference in distance between the first pair of collocated cameras and the at least one additional pair of collocated cameras and allow separation of the subject's body movement from vital signs related to depth changes and being further optionally used to obtain movement compensated estimates of HR and/or RR from the second set of intensity data and depth data.

* * * * *